US012314437B2

(12) United States Patent
Dods et al.

(10) Patent No.: US 12,314,437 B2
(45) Date of Patent: May 27, 2025

(54) SECURE MESSAGING IN A MACHINE LEARNING BLOCKCHAIN NETWORK

(71) Applicant: LEDGERDOMAIN INC., Las Vegas, NV (US)

(72) Inventors: Victor Bovee Dods, Orinda, CA (US); Benjamin James Taylor, Las Vegas, NV (US); William Jack, Cambridge, MA (US); Leonid Alekseyev, San Francisco, CA (US)

(73) Assignee: LEDGERDOMAIN INC., Las Vegas, NV (US)

( * ) Notice: Subject to any disclaimer, the term of this patent is extended or adjusted under 35 U.S.C. 154(b) by 0 days.

(21) Appl. No.: 18/520,455

(22) Filed: Nov. 27, 2023

(65) Prior Publication Data

US 2024/0104243 A1 Mar. 28, 2024

Related U.S. Application Data

(63) Continuation of application No. 17/384,585, filed on Jul. 23, 2021, now Pat. No. 11,829,510, which is a
(Continued)

(51) Int. Cl.
*G06K 9/00* (2022.01)
*G06F 17/18* (2006.01)
(Continued)

(52) U.S. Cl.
CPC .......... *G06F 21/6245* (2013.01); *G06F 17/18* (2013.01); *G06F 18/22* (2023.01);
(Continued)

(58) Field of Classification Search
CPC ............... H04L 2209/38; H04L 9/3239; H04L 2209/56; H04L 9/3236; H04L 63/0807;
(Continued)

(56) References Cited

U.S. PATENT DOCUMENTS 7,170,391 B2   1/2007 Lane et al.
8,788,316 B1 * 7/2014 Karnik ................... G06F 21/10
                                                              705/7.35
(Continued)

FOREIGN PATENT DOCUMENTS

CN        110597902 A    12/2019
WO     2018206408 A1    11/2018
(Continued)

OTHER PUBLICATIONS

Abid et al., Block-Chain Security Advancement in Medical Sector for sharing Medical Records, 2019 International Conference on Innovative Computing (ICIC) (Year: 2019).
(Continued)

*Primary Examiner* — Alex Kok S Liew
(74) *Attorney, Agent, or Firm* — HAYNES BEFFEL & WOLFELD LLP; Andrew L. Dunlap; Paul A. Durdik

(57) ABSTRACT

Multi-layer ensembles of neural subnetworks are disclosed. Implementations can classify inputs indicating various anomalous sensed conditions into probabilistic anomalies using an anomaly subnetwork. Determined probabilistic anomalies are classified into remedial application triggers invoked to recommend or take actions to remediate, and/or report the anomaly. Implementations can select a report type to submit, or a report recipient, based upon the situation state, e.g., FDA: Field Alert Report (FAR), Biological Product Deviation Report (BPDR), Medwatch, voluntary reporting by healthcare professionals, consumers, and patients (Forms 3500, 3500A, 3500B, Reportable Food Registry, Vaccine Adverse Event Reporting System (VAERS), Investigative Drug/Gene Research Study Adverse Event Reports, Potential Tobacco Product Violations Reporting (Form 3779), USDA: *APHIS* Center for Veterinary Biologics Reports, Animal and Plant Health Inspection Service: Adverse Event Reporting, FSIS Electronic Consumer Com-
(Continued)

plaints, DEA Tips, Animal Drug Safety Reporting, Consumer Product Safety Commission Reports, State/local reports: Health Department, Board of Pharmacy.

21 Claims, 35 Drawing Sheets

Related U.S. Application Data continuation of application No. 17/063,605, filed on Oct. 5, 2020, now Pat. No. 11,081,219.

(60) Provisional application No. 62/961,594, filed on Jan. 15, 2020.

(51) Int. Cl.
| | |
|---|---|
| *G06F 18/22* | (2023.01) |
| *G06F 18/23* | (2023.01) |
| *G06F 21/62* | (2013.01) |
| *G06N 3/08* | (2023.01) |
| *G06N 20/00* | (2019.01) |
| *G16H 20/10* | (2018.01) |
| *H04L 9/06* | (2006.01) |
| *H04L 9/40* | (2022.01) |
| *H04L 9/00* | (2022.01) |

(52) U.S. Cl.
CPC .......... *G06F 18/23* (2023.01); *G06F 21/6227* (2013.01); *G06N 3/08* (2013.01); *G06N 20/00* (2019.01); *G16H 20/10* (2018.01); *H04L 9/0643* (2013.01); *H04L 63/0838* (2013.01); *H04L 63/0853* (2013.01); *H04L 63/108* (2013.01); *H04L 9/50* (2022.05)

(58) Field of Classification Search
CPC ... H04L 9/0637; H04L 9/3213; H04L 9/3247; H04L 9/3297; H04L 67/10; H04L 67/104; H04L 63/061; H04L 63/08; H04L 63/0815; H04L 67/12; H04L 9/0643; G06Q 2220/00; G06Q 20/065; G06Q 20/308; G06Q 20/384; G06Q 20/10; G06Q 20/3678; G06Q 20/3829; G06Q 20/36; G06Q 20/367; G06Q 40/00
See application file for complete search history.

(56) References Cited

U.S. PATENT DOCUMENTS

| | | |
|---|---|---|
| 9,870,508 B1 | 1/2018 | Hodgson et al. |
| 10,268,974 B2 | 4/2019 | Wiig et al. |
| 10,356,087 B1 | 7/2019 | Vetter et al. |
| 10,491,404 B1 | 11/2019 | Yamamoto |
| 10,491,578 B1 | 11/2019 | Hebert et al. |
| 10,496,802 B2 | 12/2019 | Weis |
| 10,509,684 B2 | 12/2019 | Florissi et al. |
| 10,516,525 B2 | 12/2019 | Bhattacharya et al. |
| 10,540,704 B2 | 1/2020 | Mazed et al. |
| 10,542,046 B2 | 1/2020 | Katragadda et al. |
| 10,990,693 B1 | 4/2021 | Newman |
| 11,468,046 B2 | 10/2022 | Conley et al. |
| 11,509,709 B1 | 11/2022 | Basak et al. |
| 11,736,290 B1 | 8/2023 | Dods et al. |
| 11,741,215 B1 | 8/2023 | Dods et al. |
| 11,741,216 B1 | 8/2023 | Dods et al. |
| 11,769,577 B1 | 9/2023 | Dods et al. |
| 11,829,510 B2 | 11/2023 | Dods et al. |
| 11,848,754 B1 | 12/2023 | Dods et al. |
| 2012/0130905 A1 | 5/2012 | Tsudik et al. |
| 2014/0006048 A1 | 1/2014 | Liberty |
| 2014/0025443 A1 | 1/2014 | Onischuk |
| 2014/0040153 A1 | 2/2014 | Singh et al. |
| 2014/0108043 A1 | 4/2014 | Ach et al. |
| 2015/0039700 A1 | 2/2015 | West et al. |
| 2015/0262171 A1 | 9/2015 | Langschaedel et al. |
| 2015/0269379 A1 | 9/2015 | Ramzan et al. |
| 2016/0125199 A1 | 5/2016 | Lee et al. |
| 2016/0155069 A1 | 6/2016 | Hoover et al. |
| 2016/0212146 A1 | 7/2016 | Wilson |
| 2017/0103167 A1 | 4/2017 | Shah |
| 2017/0116693 A1 | 4/2017 | Rae et al. |
| 2017/0221032 A1 | 8/2017 | Mazed |
| 2017/0286880 A1 | 10/2017 | Wiig et al. |
| 2017/0310653 A1* | 10/2017 | Zhang ................. H04L 63/0838 |
| 2017/0337588 A1 | 11/2017 | Chittilappilly et al. |
| 2018/0048461 A1 | 2/2018 | Jutla et al. |
| 2018/0114169 A1 | 4/2018 | Wiig et al. |
| 2018/0121634 A1 | 5/2018 | Hughes et al. |
| 2018/0139186 A1 | 5/2018 | Castagna |
| 2018/0204191 A1 | 7/2018 | Wilson et al. |
| 2018/0341648 A1 | 11/2018 | Kakavand et al. |
| 2019/0012249 A1 | 1/2019 | Mercuri et al. |
| 2019/0020661 A1* | 1/2019 | Zhang ................. H04L 63/0823 |
| 2019/0026450 A1* | 1/2019 | Egner ..................... G06F 21/44 |
| 2019/0051079 A1* | 2/2019 | Venkataraman ...... H04L 9/3239 |
| 2019/0052453 A1 | 2/2019 | de Ligt |
| 2019/0057386 A1 | 2/2019 | Fazeli et al. |
| 2019/0058599 A1 | 2/2019 | Takada Chino et al. |
| 2019/0068562 A1 | 2/2019 | Iyer et al. |
| 2019/0075102 A1 | 3/2019 | Kim et al. |
| 2019/0108898 A1 | 4/2019 | Gulati |
| 2019/0138905 A1 | 5/2019 | Akella et al. |
| 2019/0138971 A1 | 5/2019 | Uggirala et al. |
| 2019/0141119 A1 | 5/2019 | Bernat et al. |
| 2019/0171438 A1 | 6/2019 | Franchitti |
| 2019/0180276 A1 | 6/2019 | Lee et al. |
| 2019/0198932 A1* | 6/2019 | Newhouse .......... H01M 10/052 |
| 2019/0222570 A1 | 7/2019 | Krishan |
| 2019/0228174 A1 | 7/2019 | Withrow et al. |
| 2019/0251295 A1 | 8/2019 | Vieyra |
| 2019/0281066 A1 | 9/2019 | Simons |
| 2019/0325507 A1 | 10/2019 | Rowley et al. |
| 2019/0333116 A1 | 10/2019 | Bhardwaj et al. |
| 2019/0334716 A1 | 10/2019 | Kocsis et al. |
| 2019/0392162 A1 | 12/2019 | Stern et al. |
| 2020/0005133 A1 | 1/2020 | Zhang et al. |
| 2020/0013229 A1* | 1/2020 | Lee ......................... H04L 67/10 |
| 2020/0019288 A1 | 1/2020 | D'Amore et al. |
| 2020/0084483 A1 | 3/2020 | Brown et al. |
| 2020/0110821 A1 | 4/2020 | Chan et al. |
| 2020/0118060 A1 | 4/2020 | Mukherjee et al. |
| 2020/0137557 A1 | 4/2020 | Touati et al. |
| 2020/0153606 A1 | 5/2020 | Li et al. |
| 2020/0186358 A1 | 6/2020 | Capola et al. |
| 2020/0211694 A1 | 7/2020 | Nye et al. |
| 2020/0213218 A1 | 7/2020 | Demeilliez et al. |
| 2020/0219099 A1 | 7/2020 | Mohassel et al. |
| 2020/0252205 A1* | 8/2020 | Padmanabhan ... G06F 16/24564 |
| 2020/0258166 A1 | 8/2020 | Cross et al. |
| 2020/0265031 A1 | 8/2020 | Greven |
| 2020/0268260 A1 | 8/2020 | Tran |
| 2020/0294033 A1 | 9/2020 | Wilson et al. |
| 2020/0320207 A1 | 10/2020 | Beno et al. |
| 2020/0322169 A1 | 10/2020 | Michaud et al. |
| 2020/0374137 A1 | 11/2020 | Godfrey |
| 2020/0374145 A1 | 11/2020 | Kau et al. |
| 2020/0389499 A1 | 12/2020 | Koval et al. |
| 2020/0403809 A1 | 12/2020 | Chan et al. |
| 2021/0034779 A1 | 2/2021 | Signorini et al. |
| 2021/0125725 A1 | 4/2021 | Allen et al. |
| 2021/0126797 A1 | 4/2021 | Peng |
| 2021/0136068 A1 | 5/2021 | Smeets et al. |
| 2021/0150205 A1 | 5/2021 | Snyder et al. |
| 2021/0158309 A1 | 5/2021 | McGinlay et al. |
| 2021/0174914 A1 | 6/2021 | Cano et al. |
| 2021/0182539 A1 | 6/2021 | Rassool |
| 2021/0208960 A1 | 7/2021 | Dande et al. |
| 2021/0218720 A1 | 7/2021 | Oberhauser et al. |
| 2021/0234672 A1 | 7/2021 | Zeng et al. |
| 2021/0264520 A1 | 8/2021 | Cummings |
| 2021/0279731 A1 | 9/2021 | Agrawal et al. |

(56) References Cited

U.S. PATENT DOCUMENTS

| | | | |
|---|---|---|---|
| 2022/0051240 | A1 | 2/2022 | Shamai et al. |
| 2022/0051314 | A1 | 2/2022 | Enkhtaivan |
| 2022/0052988 | A1 | 2/2022 | Gadnis et al. |
| 2022/0083936 | A1 | 3/2022 | Balinsky et al. |
| 2022/0150077 | A1 | 5/2022 | Kim |
| 2022/0179378 | A1 | 6/2022 | Gourisetti et al. |
| 2022/0182368 | A1 | 6/2022 | Madisetti et al. |
| 2022/0405750 | A1 | 12/2022 | Fallah et al. |
| 2022/0407856 | A1 | 12/2022 | Jawed |
| 2022/0414237 | A1 | 12/2022 | Lally et al. |
| 2022/0417331 | A1 | 12/2022 | Devine et al. |
| 2023/0006845 | A1 | 1/2023 | Leedom, Jr. |

FOREIGN PATENT DOCUMENTS

| | | | |
|---|---|---|---|
| WO | 2019086553 | A1 | 5/2019 |
| WO | 2019090264 | A1 | 5/2019 |
| WO | 2019090268 | A1 | 5/2019 |
| WO | 2019207297 | A1 | 10/2019 |
| WO | 2020006121 | A1 | 1/2020 |
| WO | 2021127577 | A1 | 6/2021 |

OTHER PUBLICATIONS

Androulaki et. al., Hyperledger Fabric: A distributed operating system for permissioned blockchains, Proceedings for EuroSys 2018 Conference, revised Apr. 17, 2018, 15 pages. Retrieved on Oct. 2, 2021. Retrieved from the internet [URL: https://arxiv.org/abs/1801.10228 ].
Ashkar et. al., Evaluation of Decentralized Verifiable Credentials to Authenticate Authorized Trading Partners and Verify Drug Provenance, Blockchain for Healthcare Today, dated Mar. 11, 2021, 14 pages. Retrieved on Oct. 3, 2021. Retrieved from the internet [URL: https://blockchainhealthcaretoday.com/index.php/journal/article/view/168 ].
Bogdanov, Pseudorandom Functions: Three Decades Later, dated 2017, 72 pages. Retrieved on Oct. 6, 2021. Retrieved from the internet [URL: https://eprint.iacr.org/2017/652.pdf].
Bossert, I Was the Homeland Security Adviser to Trump. We're Being Hacked., The New York Times, dated Dec. 16, 2020, 3 pages. Retrieved on Oct. 3, 2021. Retrieved from the internet [URL: https://www.nytimes.com/2020/12/16/opinion/fireeye-solarwinds-russia-hack.html ].
Bourque, Ditching passwords and increasing e-commerce conversion rates by 54%, CIO, dated May 1, 2017, 4 pages. Retrieved on Oct. 2, 2021. Retrieved from the internet [URL: https://www.cio.com/article/3193206/ditching-passwords-and-increasing-ecommerce-conversion-rates-by-54.html ].
Brook, "What's the Cost of a Data Breach in 2019?", Data Insider—Digital Guardian, dated Dec. 1, 2020, 8 pages. Retrieved on Oct. 2, 2021. Retrieved from the internet [URL: https://digitalguardian.com/blog/whats-cost-data-breach-2019 ].
Callahan et al., Six Principles for Self-Sovereign Biometrics, Web of Trust Info., GitHub, dated Oct. 6, 2019,7 pages. Retrieved on Oct. 5, 2021. Retrieved from the internet [URL: https://github.com/WebOfTrustInfo/rwot6-santabarbara/blob/master/draft-documents/Biometrics.md].
Callahan, Council Post: Know Your Customer (KYC) Will Be a Great Thing When It Works, Forbes, dated Jul. 10, 2018, 8 pages. Retrieved on Oct. 1, 2021. Retrieved from [URL: https://www.forbes.com/sites/forbestechcouncil/2018/07/10/know-your-customer-kyc-will-be-a-great-thing-when-it-works/?sh=722a21178dbb ].
Chadwick et. al., Verifiable Credentials Data Model 1.0: Expressing verifiable information on the Web, World Wide Web Consortium (W3C), dated Nov. 19, 2019, 68 pages. Retrieved on Oct. 1, 2021. Retrieved from the internet [URL: https://www.w3.org/TR/vc-data-model/ ].
Chien et al., The Last Mile: DSCSA Solution Through Blockchain Technology: Drug Tracking, Tracing and Verification at the Last Mile of the Pharmaceutical Supply Chain with BRUINchain, Blockchain in Healthcare Today, dated Mar. 12, 2020, 28 pages. Retrieved on Oct. 2, 2021. Retrieved from the internet [URL: https://blockchainhealthcaretoday.com/index.php/journal/article/view/134 ].
COVID-19 Credentials Initiative, Hello World from the COVID-19 Credentials Initiative, dated Jun. 25, 2020, 3 pages. Retrieved on Oct. 3, 2021. Retrieved from the internet [URL: https://cci-2020.medium.com/hello-world-from-the-covid-19-credentials-initiative-6d45534c4b3a ].
DIF—Decentralized Identity Foundation, Homepage, dated 2021, 8 pages. Retrieved on Oct. 6, 2021. Retrieved from the internet [URL: https://identity.foundation/ ].
Dodds, Follow Your Nose, Linked Data Patterns, dated May 31, 2012, 2 pages. Retrieved on Oct. 3, 2021. Retrieved from the internet [URL: https://patterns.dataincubator.org/book/follow-your-nose.html ].
Drug Supply Chain Security Act (DSCSA), Food and Drug Administration (FDA), retrieved on Oct. 1, 2021, 3 pages. Retrieved from [URL: https://www.fda.gov/drugs/drug-supply-chain-integrity/drug-supply-chain-security-act-dscsa ].
DSCSA Pilot Project Program, Food and Drug Administration (FDA), updated May 22, 2019, 4 pages. Retrieved on Oct. 2, 2021. Retrieved from the internet [URL: https://www.fda.gov/drugs/drug-supply-chain-security-act-dscsa/dscsa-pilot-project-program ].
Entities, Spherity, 3 pages. Retrieved on Oct. 3, 2021. Retrieved from the internet [URL: https://docs.spherity.com/spherity-api/verifiable-credentials-api/entities ].
FDA's Technology Modernization Action Plan (TMAP), Food and Drug Administration (FDA), dated Sep. 18, 2019, 10 pages. Retrieved on Oct. 3, 2021. Retrieved from the internet [URL: https://www.fda.gov/media/130883/download].
Federal Trade Commission, Federal Law Requires All Businesses to Truncate Credit Card Information on Receipts, Federal Trade Commission (FTC), dated May 2007, 3 pages. Retrieved on Oct. 2, 2021. Retrieved from the internet [URL: https://www.ftc.gov/tips-advice/business-center/guidance/slip-showing-federal-law-requires-all-businesses-truncate ].
Freisleben, VRS Updates: Past, Present and Future, dated Dec. 12, 2018, Healthcare Distribution Alliance (HDA) 6 pages. Retrieved on Oct. 1, 2021. Retrieved from the internet [URL: https://www.hda.org/news/hda-blog/2018/12/07/14/44/2018-12-12-vrs-update-past-present-future ].
Gabay, Federal Controlled Substances Act: Ordering and Recordkeeping, Hospital Pharmacy, dated Dec. 9, 2013, 3 pages. Retrieved on Oct. 2, 2021. Retrieved from the internet [URL: https://www.ncbi.nlm.nih.gov/pmc/articles/PMC3875106/].
General Meeting Agenda—Healthcare SIG, Hyperledger Foundation, updated Feb. 17, 2021, 2 pages. Retrieved on Oct. 3, 2021. Retrieved from the internet [URL: https://wiki.hyperledger.org/display/HCSIG/2021.02.17+General+Meeting+Agenda ].
Google Protocol Buffers—Google's data interchange format, Github, dated 2008, 6 pages. Retrieved on Oct. 3, 2021. Retrieved from the internet [URL: https://github.com/protocolbuffers/protobuf ].
Grassi et al., NIST Special Publication 800-63C, Digital Identity Guidelines—Federation and Assertions, retrieved on Oct. 1, 2021, 48 pages. Retrieved from [ URL: https://pages.nist.gov/800-63-3/sp800-63c.html ].
Grassi et al., Digital Identity Guidelines, NIST Special Publication 800-63-3, dated Jun. 2017, 75 pages. Retrieved on Oct. 6, 2021. Retrieved from the internet [URL: https://doi.org/10.6028/NIST.SP.800-63-3.
Grassi et al., Digital Identity Guidelines: Authentication and Lifecycle Management, NIST Special Publication 800-63B, dated Jun. 2017, 79 pages. Retrieved on Oct. 6, 2021. Retrieved from the internet [URL: https://doi.org/10.6028/NIST.SP.800-63b ].
Grassi et al., Digital Identity Guidelines: Federation and Assertions, NIST Special Publication 800-63C, dated Jun. 2017, 49 pages. Retrieved on Oct. 6, 2021. Retrieved from the internet [URL: https://doi.org/10.6028/NIST.SP.800-63c ].
GS1 Healthcare U.S. Standard 1.1—Applying the GS1 Lightweight Messaging Standard for DSCSA Verification of Returned Product Identifiers, dated Mar. 31, 2020, 60 pages. Retrieved on Oct. 1, 2021. Retrieved from the Internet [URL: https://www.gs1us.org/

(56) References Cited

OTHER PUBLICATIONS

DesktopModules/Bring2mind/DMX/Download.aspx?Command=Core_Download&EntryId=1897&language=en-US&PortalId=0&TabId=134 ].

GS1 Healthcare U.S., Assessing Current Implementation of DSCSA Serialization Requirements, GS1 US, dated 2018, 6 pages. Retrieved on Oct. 2, 2021. Retrieved from the internet [URL: https://www.gs1us.org/DesktopModules/Bring2mind/DMX/Download.aspx?Command=Core_Download&EntryId=1210&language=en-US&PortalId=0&TabId=134 ].

GS1 Healthcare U.S., GS1 Lightweight Messaging Standard for Verification of Product Identifiers, dated Dec. 2018, 30 pages. Retrieved on Oct. 2, 2021. Retrieved from the internet [URL: https://www.gs1.org/docs/epc/GS1_Lightweight_Verification_Messaging_Standard.pdf ].

GS1 Healthcare U.S., Standard 1.2, Applying GS1 Standards for DSCSA and Traceability, dated Nov. 7, 2016, 126 pages. Retrieved on Oct. 2, 2021. Retrieved from the internet [URL: https://www.gs1us.org/DesktopModules/Bring2mind/DMX/Download.aspx?Command=Core_Download&EntryId=749&language=en-US&PortalId=0&TabId=134 ].

GS1 Standards Resources for DSCSA Implementation Support, GS1 US, dated Feb. 22, 2021, 7 pages. Retrieved on Oct. 3, 2021. Retrieved from the internet [URL: https://www.gs1us.org/industries/healthcare/standards-in-use/pharmaceutical/dscsa-resources ].

GS1 U.S., DSCSA Pilot Project readiness results, PDG FDA Pilot Program Round—Robin Webinar Series, dated Jun. 30, 2020, slides 16-29. Retrieved on Oct. 2, 2021. Retrieved from the internet [URL: : https://dscsagovernance.org/wp-content/uploads/2020/08/Attachment-A-Presentations.pdf ].

Hammi, M.T. et al., Apr. 2018. "BCTrust: A decentralized authentication blockchain-based mechanism". In 2018 IEEE wireless communications and networking conference (WCNC) (pp. 1-6). IEEE. (Year: 2018), in 6 pages.

Hardman, Verifiable Data Registry (Image), Wikipedia, dated Nov. 5, 2019, 1 page. Retrieved on Oct. 6, 2021. Retrieved from the internet [URL: https://en.wikipedia.org/wiki/Verifiable_credentials#/media/File:VC_triangle_of_Trust.svg ].

HDA Saleable Returns Pilot Study Identifies Two Recommendations to Meet 2019 DSCSA Requirements, Healthcare Distribution Alliance (HDA), dated Nov. 10, 2016, 5 pages. Retrieved on Oct. 3, 2021. Retrieved from the internet [URL: https://www.hda.org/news/2016-11-10-hda-pilot-results-revealed ].

Heath, SolarWinds hack was 'largest and most sophisticated attack' ever-Microsoft president, Financial Post, dated Feb. 14, 2021, 3 pages. Retrieved on Oct. 3, 2021. Retrieved from the internet [URL: https://financialpost.com/pmn/business-pmn/solarwinds-hack-was-largest-and-most-sophisticated-attack-ever-microsoft-president ].

Housley et. al., Trust Anchor Format, Internet Engineering Task Force (IETF), dated Jun. 2021, 14 pages. Retrieved on Oct. 3, 2021. Retrieved from the internet [URL: https://datatracker.ietf.org/doc/html/rfc5914 ].

How to share an OpenPGP public key easily in three steps, Mailfence, dated Jul. 11, 2017, 14 pages. Retrieved on Aug. 13, 2021. Retrieved from the internet [URL: https://blog.mailfence.com/openpgp-public-key/ ].

Hyperledger, Ursa, Github, updated 2021, 7 pages. Retrieved on Oct. 3, 2021. Retrieved from the internet [URL: https://github.com/hyperledger/ursa ].

Identity-concept.svg, Wikimedia Commons, 3 pages. Retrieved on Oct. 6, 2021. Retrieved from the internet [URL: https://commons.wikimedia.org/wiki/File:Identity-concept.svg ].

Jurgens, Industry-wide DSCSA Compliance Pilot Successfully Completed, Spherity, dated Dec. 17, 2020, 15 pages. Retrieved on Oct. 1, 2021. Retrieved from the internet [URL: https://medium.com/spherity/industry-wide-dscsa-compliance-pilot-successfully-completed-d7223a0f2c92 ].

Kaptjin et. al., X.509 DID method, WebOfTrustInfo, GitHub, dated Aug. 12, 2019, 6 pages. Retrieved on Oct. 5, 2021. Retrieved from the internet [URL: https://github.com/WebOfTrustInfo/rwot9-prague/blob/master/topics-and-advance-readings/X.509-DID-Method.md ].

Keen et. al., Forecasts Worldwide Information Security Spending to Exceed $124 Billion in 2019, Gartner, dated Aug. 15, 2018, 5 pages. Retrieved on Oct. 2, 2021. Retrieved from the internet [URL: https://www.gartner.com/en/newsroom/press-releases/2018-08-15-gartner-forecasts-worldwide-information-security-spending-to-exceed-124-billion-in-2019 ].

Krebs, at Least 30,000 U.S. Organizations Newly Hacked via Holes in Microsoft's Email, Krebson Security, dated Mar. 5, 2021, 6 pages. Retrieved on Oct. 3, 2021. Retrieved from the internet. [URL: https://krebsonsecurity.com/2021/03/at-least-30000-u-s-organizations-newly-hacked-via-holes-in-microsofts-email-software/ ].

Lodder et. al., Sovrin DID Method Specification, Sovrin Foundation, dated Aug. 20, 2021, 16 pages. Retrieved on Oct. 3, 2021. Retrieved from the internet [URL: https://sovrin-foundation.github.io/sovrin/spec/did-method-spec-template.html ].

Looker et. al., BBS+ Signatures 2020 Draft Community Group Report, W3C Community Group, dated Jun. 13, 2021, 31 pages. Retrieved on Oct. 3, 2021. Retrieved from the internet [URL: https://w3c-ccg.github.io/ldp-bbs2020/ ].

Lu, "How Much are Password Resets Costing Your Company?", Okta, dated Aug. 20, 2019, 2 pages. Retrieved on Oct. 2, 2021. Retrieved from the internet [URL: https://www.okta.com/blog/2019/08/how-much-are-password-resets-costing-your-company/ ].

Makaay et. al., Frameworks for Identity Systems, Open Identity Exchange (OIX), dated Jun. 2017, 18 pages. Retrieved on Oct. 5, 2021. Retrieved from the internet [URL: https://connectis.com/wp-content/uploads/2018/05/OIX-White-Paper_Trust-Frameworks-for-Identity-Systems_Final.pdf].

Matney, Apple's global active install base of iPhones surpassed 900 million this quarter, TechCrunch, dated Jan. 29, 2019, 2 pages. Retrieved on Oct. 2, 2021. Retrieved from the internet [URL: https://techcrunch.com/2019/01/29/apples-global-active-install-base-of-iphones-surpassed-900-million-this-quarter/].

Mitre, Broad Coalition of Health and Technology Industry Leaders Announce Vaccination Credential Initiative to Accelerate Digital Access to COVID-19 Vaccination Records, dated Jan. 14, 2021, 5 pages. Retrieved on Oct. 3, 2021. Retrieved from the internet [URL: https://www.businesswire.com/news/home/20210114005294/en/Broad-Coalition-of-Health-and-Technology-Industry-Leaders-Announce-Vaccination-Credential-Initiative-to-Accelerate-Digital-Access-to-COVID-19-Vaccination-Records ].

Newton, The battle inside Signal, The Verge, dated Jan. 25, 2021, 19 pages. Retrieved on Oct. 3, 2021. Retrieved from the internet. [URL: https://www.theverge.com/platform/amp/22249391/signal-app-abuse-messaging-employees-violence-misinformation ].

Object Management Group Issues Request for Information for Disposable Self-Sovereign Identity Standard, Object Management Group (OMG), dated Jan. 21, 2021, 3 pages. Retrieved on Oct. 3, 2021. Retrieved from the internet [URL: https://www.omg.org/news/releases/pr2021/01-21-21.htm ].

Otto et. al., Verifiable Credentials Use Cases, W3C Working Group, dated Sep. 24, 2019, 35 pages. Retrieved on Oct. 3, 2021. Retrieved from the internet [URL: https://www.w3.org/TR/vc-use-cases/ ].

Partnership for DSCSA Governance, PDG, 2021, 3 pages. Retrieved on Oct. 3, 2021. Retrieved from the internet [URL: https://dscsagovernance.org/ ].

Pharmacompass, Top 1000 Global Pharmaceutical Companies, LePro PharmaCompass OPC, dated Sep. 2020, 101 pages. Retrieved on Oct. 6, 2021. Retrieved from the internet [URL: https://www.pharmacompass.com/data-compilation/top-1000-global-pharmaceutical-companies ].

Ponemon, What's New in the 2019 Cost of a Data Breach Report, Security Intelligence, dated Jul. 23, 2019, 10 pages. Retrieved on Oct. 2, 2021. Retrieved from the internet [URL: https://securityintelligence.com/posts/whats-new-in-the-2019-cost-of-a-data-breach-report/ ].

Prabha, P. et al., Dec. 2020. Securing telecare medical information system with blockchain technology. In 2020 2nd International

(56) References Cited

OTHER PUBLICATIONS

Conference on Advances in Computing, Communication Control and Networking (ICACCCN) (pp. 846-851). IEEE. (Year: 2020), in 6 pages.
Rahman et al., Blockchain Based Mobile Edge Computing Framework for Secure Therapy Applications, 2018, IEEE Special Section on Mobile Multimedia for Healthcare, vol. 6, pp. 72469-72478 (Year: 2018).
Reed et. al., What are Decentralized Identifiers (DIDs)?, Evernym on Slideshare, dated Sep. 30, 2019, 29 pages. Retrieved on Oct. 3, 2021. Retrieved from the internet [URL: https://www.slideshare.net/Evernym/what-are-decentralized-identifiers-dids ].
Rose et. al., Zero Trust Architecture, NIST Special Publication 800-207, dated Aug. 2020, 59 pages. Retrieved on Oct. 6, 2021. Retrieved from the internet [URL: https://csrc.nist.gov/publications/detail/sp/800-207/final ].
Rossberg, WebAssembly Core Specification, W3C Working Group, W3C, dated Dec. 5, 2019, 164 pages. Retrieved on Oct. 5, 2021. Retrieved from the internet [URL: https://www.w3.org/TR/wasm-core-1/].
Searls, New Hope for Digital Identity, Linux Journal, dated Nov. 9, 2017, 7 pages. Retrieved on Oct. 4, 2021. Retrieved from the internet [URL: https://www.linuxjournal.com/content/new-hope-digital-identity ].
Shuaib et. al., Blockchains for Secure Digitized Medicine, Journal of Personalized Medicine, dated Jul. 13, 2019, 9(3): 35, 21 pages. Retrieved on Oct. 2, 2021. Retrieved from the internet [URL: https://www.mdpi.com/2075-4426/9/35 ].
Sovrin Governance Framework Working Group, Sovrin Governance Framework V2, Sovrin Foundation, dated Dec. 4, 2019, 20 pages. Retrieved on Oct. 5, 2021. Retrieved from the internet [URL: https://sovrin.org/wp-content/uploads/Sovrin-Governance-Framework-V2-Master-Document-V2.pdf ].
Sporny et. al., Verifiable Credentials Data Model 1.0, W3C Working Group. dated Nov. 19, 2019, 122 pages. Retrieved on Oct. 3, 2021. Retrieved from the internet [URL: https://www.w3.org/TR/vc-data-model/ ].
StClair et. al., Blockchain, Interoperability, and Self-Sovereign Identity: Trust Me, It's My Data, Blockchain in Healthcare Today, dated Jan. 6, 2020, 3 pages. Retrieved on Oct. 3, 2021. Retrieved from the internet [URL: https://blockchainhealthcaretoday.com/index.php/journal/article/view/122/144 ].
Steel, Passwords Are Still a Problem According to the 2019 Verizon Data Breach Investigations Report, LastPass Blog, dated May 21, 2019, 4 pages. Retrieved on Oct. 2, 2021. Retrieved from the internet [URL: https://blog.lastpass.com/2019/05/passwords-still-problem-according-2019-verizon-data-breach-investigations-report/ ].
Temoshok et. al., Developing Trust Frameworks to Support Identity Federations, National Institute of Standards and Technology (NIST), dated Jan. 2018, 34 pages. Retrieved on Oct. 4, 2021. Retrieved from the internet [URL: http://dx.doi.org/10.6028/NIST.IR.8149 ].
Thayer, "Why Does Mozilla Maintain Our Own Root Certificate Store?", Mozilla Security Blog, dated Feb. 14, 2019, 3 pages. Retrieved on Oct. 3, 2021. Retrieved from the internet [URL: https://blog.mozilla.org/security/2019/02/14/why-does-mozilla-maintain-our-own-root-certificate-store/ ].
The Commons project, Unlocking the full potential of technology and data for the common good, 2019-2021, 5 pages. Retrieved on Oct. 3, 2021. Retrieved from the internet [URL: https://thecommonsproject.org/commonpass ].
Tobin et al., The Inevitable Rise of Self-Sovereign Identity, Sovrin Foundation Whitepaper, updated Mar. 28, 2017, 24 pages. Retrieved on Oct. 3, 2021. Retrieved from the internet [URL: https://sovrin.org/wp-content/uploads/2018/03/The-Inevitable-Rise-of-Self-Sovereign-Identity.pdf ].
U.S. Department of Health and Human Services Food and Drug Administration, Verification Systems Under the Frug Supply Chain Security Act for Certain Prescription Drugs, Guidance for Industry, Draft Guidance, dated Oct. 2018, 14 pages. Retrieved on Oct. 2, 2021. Retrieved from the internet [URL: https://www.fda.gov/media/117950/download ].
U.S. Department of Health and Human Services Food and Drug Administration, Wholesale Distributor Verification Requirement for Saleable Returned Drug Product and Dispenser Verification Requirements When Investigating a Suspect or Illegitimate Product—Compliance Policies, Guidance for Industry, dated Oct. 2020, 10 pages. Retrieved on Oct. 2, 2021. Retrieved from the internet [URL: https://www.fda.gov/media/131005/download ].
U.S. Food and Drug Administration, Drug Supply Chain Security Act Law and Policies, U.S. Department of Health and Human Services Food and Drug Administration, updated Oct. 23, 2020, 6 pages. Retrieved on Oct. 1, 2021. Retrieved from the internet [URL: https://www.fda.gov/drugs/drug-supply-chain-security-act-dscsa/drug-supply-chain-security-act-law-and-policies].
Untitled code sample, W3C Working Group, W3C, dated 2018, 7 pages. Retrieved on Oct. 6, 2021. Retrieved from the internet [URL: https://www.w3.org/2018/credentials/v1 ].
Web Assembly, Mozilla Developer Network (MDN), dated 2021, 31 pages. Retrieved on Oct. 5, 2021. Retrieved from the internet [URL: https://developer.mozilla.org/en-US/docs/WebAssembly ].
What are SMART Health Cards?, SMART Health Cards Framework, 2021, 4 pages. Retrieved on Oct. 3, 2021. Retrieved from the internet [URL: https://smarthealth.cards/ ].
XATP Working Group, Framework for extended ATP Authentication, Enhanced Verification and Saleable Returns Documentation, LedgerDomain, dated Dec. 17, 2020, 25 pages. Retrieved on Oct. 1, 2021. Retrieved from the internet [URL: https://www.xatp.org/publications ].
Young, Verifiable Credentials Flavors Explained, COVID-19 Credentials Initiative, dated Feb. 2021, 21 pages. Retrieved on Oct. 3, 2021. Retrieved from the internet [URL: https://www.lfph.io/wp-content/uploads/2021/02/Verifiable-Credentials-Flavors-Explained.pdf ].
UCLA Health, "UCLA-LedgerDomain: DSCSA Solution through Blockchain Technology: Drug Tracking, Tracing and Verification at the Last Mile of the Pharmaceutical Supply Cain with BRUINchain", PDG FDA Pilot Program Round Robin, Jul. 2020, in 160 pages.
U.S. Department of Health and Human Services, Food and Drug Administration, Identifying Trading Partners Under the Drug Supply Chain Security Act, Guidance for Industry, dated Aug. 2017, 18 pages. Retrieved on Oct. 3, 2021. Retrieved from the internet [URL: https://www.fda.gov/files/drugs/published/Identifying-Trading-Partners-Under-the-Drug-Supply-Chain-Security-Act-Guidance-for-Industry.pdf ].

\* cited by examiner

LedgerDomain Version 0 Demo - Google Chrome

□ LedgerDomain Version ×

← → C (i) localhost:3000

Apps For quick access, place your bookmarks here on the bookmar bar. Import bookmarks now.

| FDA | Pfizer | Walgreens | Dr. Dods | Mr. Gumby |

MemberId: Pfizer - Role(s): Manufacturer, Warehouse
Invoke Actions:

| Create AssetType | | | AssetType |
|---|---|---|---|
| Create Assets | AssetType | Initial Owner MemberId | AssetId0,AssetId1,... |
| Transfer Assets | | New Owner MemberId | AssetType |
| Issue License | Holder MemberId | License Type | LicenseData |

Query Actions:

| Query Member | | | MemberId |
|---|---|---|---|
| Query AssetType | | | AssetType |
| Query License | Holder MemberId | License Type | LicenseData |
| Query Inventory | | | MemberId |
| Query Licenses | | | MemberId |

Pfizer Inventory | Re-Query

Id: IDbdb6b5bc | Id: IDc18feba1 | Id: IDcd57ad90
Type: Viagra | Type: Viagra | Type: Viagra
Owner: Pfizer | Owner: Pfizer | Owner: Pfizer Role - based clients Licenses | Re-Query

[{"LicenseType" : "Manufacturer","LicenseData" : "Viagra","IssuerMemberId" : "FDA","HolderMemberId" : "Pfizer"}]

Barcode Generator | Global Inventory

Id: ID1097187a | Id: IDbdb6b5bc | Id: IDc18feba1 | Id: IDcd57ad90 | Id: ID4cca1d55 | Id: ID20e14f13
Type: <unassigned> | Type: Viagra | Type: Viagra | Type: Viagra | Type: Viagra | Type: Viagra
Owner: <unassigned> | Owner: Pfizer | Owner: Pfizer | Owner: Pfizer | Owner: Walgreens | Owner: Mr. Gumby

FIG. 8I1

FIG. 8I2

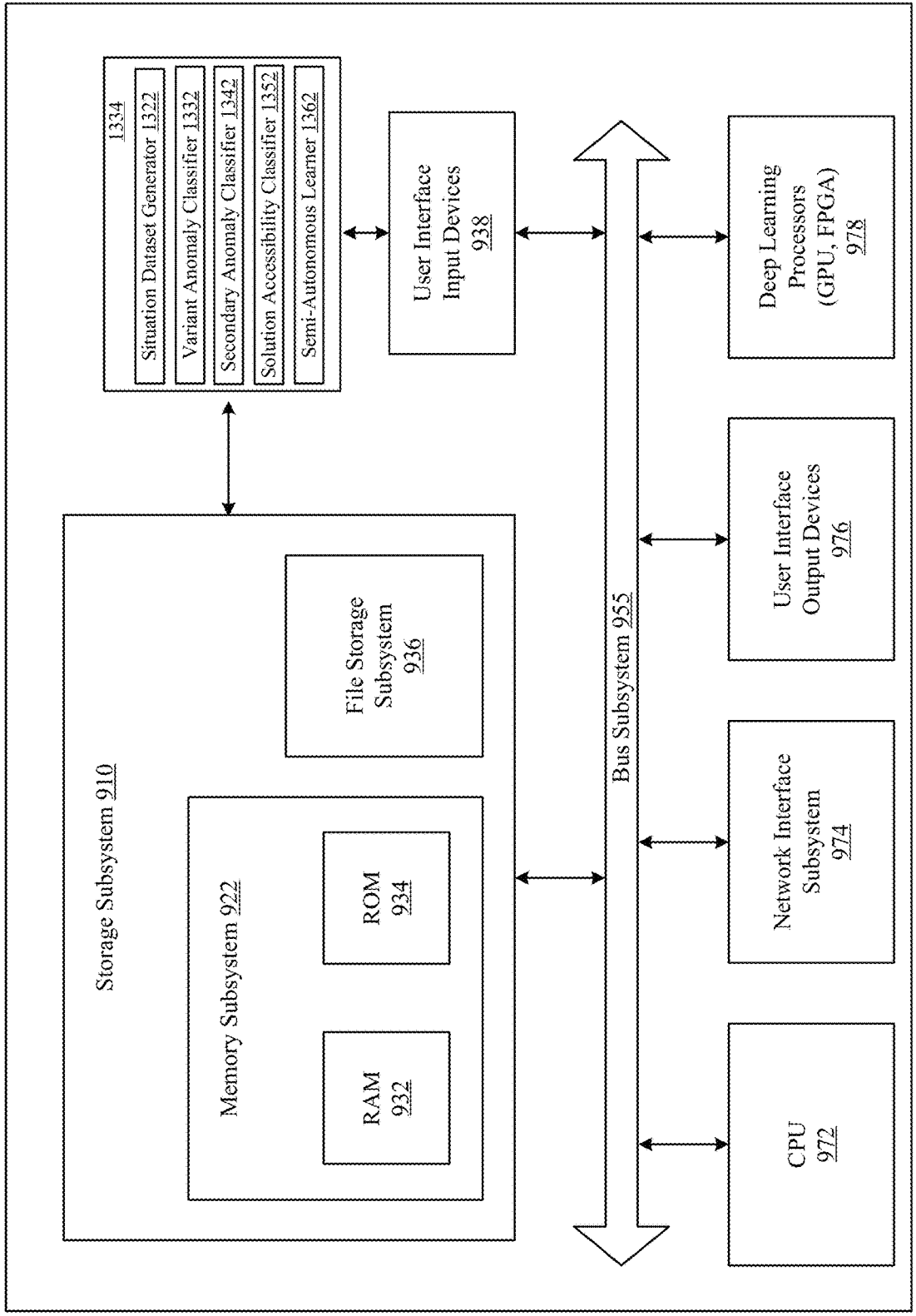
FIG. 9 – Computer System

Convolutional Neural Network

SECURE MESSAGING IN A MACHINE LEARNING BLOCKCHAIN NETWORK

RELATED APPLICATION

This application is a continuation of U.S. patent application Ser. No. 17/384,585, titled "SECURE MESSAGING IN A MACHINE LEARNING BLOCKCHAIN NETWORK", filed Jul. 23, 2021, which is a continuation of U.S. patent application Ser. No. 17/063,605, titled "SECURE MESSAGING IN A MACHINE LEARNING BLOCKCHAIN NETWORK", filed Oct. 5, 2020, which claims the benefit of U.S. Provisional Patent Application No. 62/961,594, titled "Supply Chain Tracking and Management Using Blockchain Technology", filed Jan. 15, 2020, which are incorporated herein by reference in their entirety for all purposes.

INCORPORATIONS

The following materials are incorporated herein by reference in their entirety for all purposes:
  U.S. Non-Provisional patent application Ser. No. 16/740,348, titled "Neural Network Classifiers for Block Chain Data Structures", filed Jan. 10, 2020;
  U.S. Non-Provisional patent application Ser. No. 16/740,350, titled "Establishing a Trained Machine Learning Classifier in a Blockchain Network", filed Jan. 10, 2020;
  The FDA Product-Specific Guidance database, fda.gov/drugs/guidances-drugs/product-specific-guidances-generic-drug-development;
  Andy Greenberg, "SECURITY SOFTWARE HAS A SERIOUS SUPPLY-CHAIN SECURITY PROBLEM", Wired (Sep. 18, 2017); and
  Andy Greenberg, "SUPPLY CHAIN HACKERS SNUCK MALWARE INTO VIDEOGAMES", Wired (Apr. 23, 2019).

FIELD OF THE TECHNOLOGY DISCLOSED

The technology disclosed relates to block chain centric systems of computers and digital data processing systems and corresponding data processing methods and products implementing an interoperability service enabling secure interoperability between a blockchain application and non-credentialed entities. In particular, the technology disclosed relates to using security software technology to implement interoperability between a secure blockchain application and non-credentialed personal devices, enabling a non-credentialed person to act on behalf of the blockchain system.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

Increased regulation brings with it increased safety. But the increase in safety comes with a cost—greater reporting and administrative burden. Research by the Mercatus Center at George Mason University indicates that the accumulation of rules over the past several decades has slowed economic growth, amounting to an estimated $4 trillion loss in US GDP in 2012 (had regulations stayed at 1980 levels).

As online systems are pressed into service to meet the needs driven by increased regulation, conventional technologies fail to address the complexities posed by distributed collaboratively acting systems, such as for example the need for security and authentication of collaborative systems acting in other parts of the world. For example, in a classic scenario, a malevolent attacker could send an authentic-looking request to another system actor, which diverts to the attacker's own website, could then issue an authentic-looking one-time verification code via SMS, and then ask the victim questions about whatever the attacker would like.

Diagnosis, analysis, and compliance historically require one human to have centralized access to all of other parties' data. This represents a huge threat surface. In fact, according to a study by IBM, human error is the main cause of 95% of cyber security breaches. Further, compliance requires accurate input of information. Diagnosis requires voluminous amounts of data about complex topics, which are beyond the reaches of today's database servers. Thus not all actors that provide information to automated systems should be trusted with access to the data.

What is really needed are improvements in security of transactional based systems that allow interoperability between entities trusted with access to data and non-credentialed entities.

BRIEF DESCRIPTION OF THE DRAWINGS

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which:

FIGS. 8A, 8B, 8C, 8D, 8E, 8F, 8G, 8H, 811 and 812 depict screenshots displayed by a typical client device in conjunction with an example use case 800.

FIG. 9 illustrates one implementation of a computer system 900 that can be used to implement the technology disclosed.

DETAILED DESCRIPTION OF SPECIFIC IMPLEMENTATIONS

Motivation

Figure 1A:
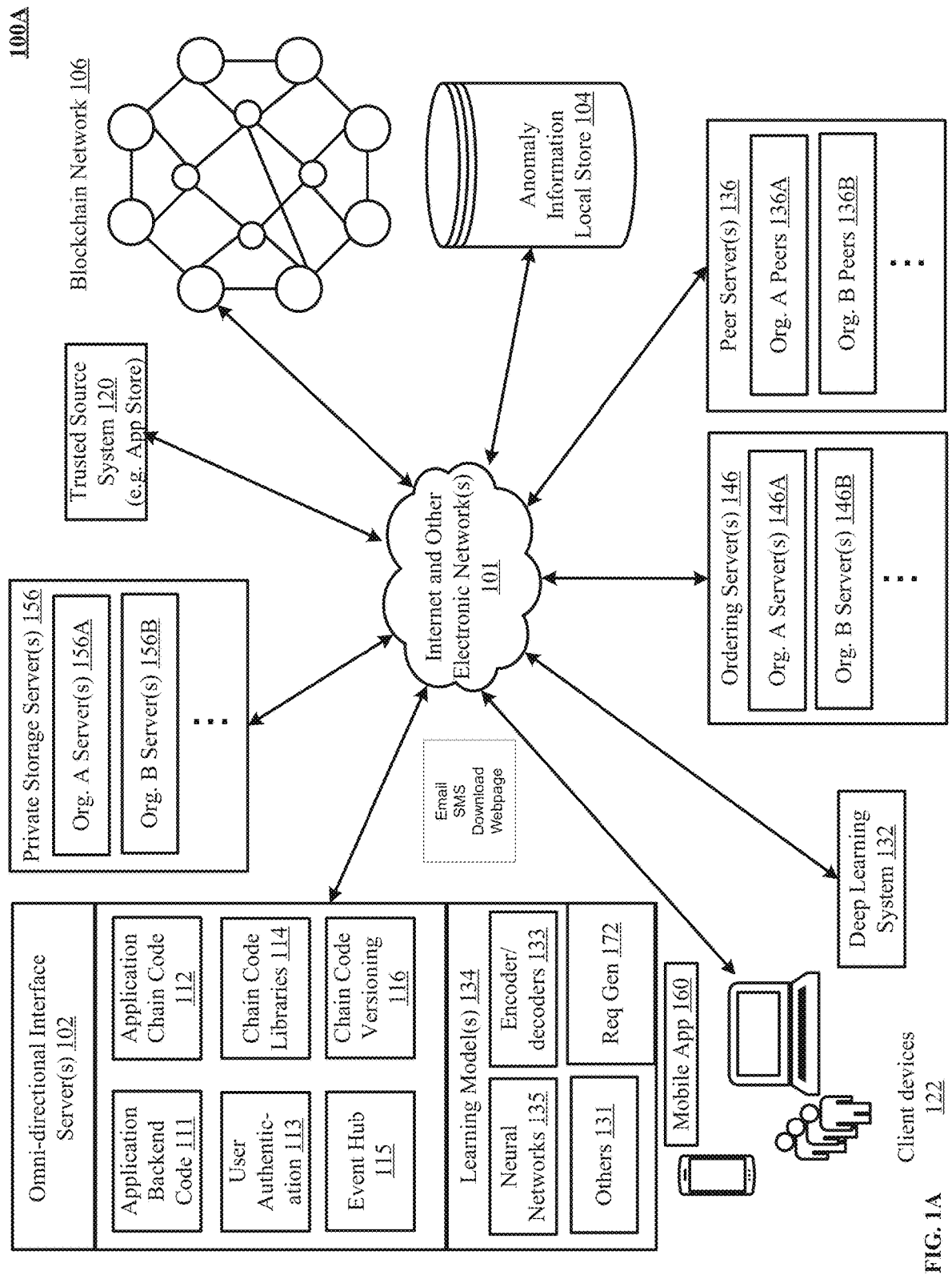
FIG. 1A shows an architectural level schematic of a system 100A that implements technology for establishing trusted relationship(s) between requester(s) and recipient(s) in a blockchain network of trusted actors.

Disclosed are system and method implemented interoperability service enabling secure interoperability between a blockchain application and non-credentialed entities. Interoperability between a secure blockchain implementation and non-credentialed entities is in contrast with entities that have credentials within the blockchain application and those that do not. Implementations can enable blockchain-validated reporting, tracking, and responding in near-real-time to anomalies such as out-of-spec asset reports in critically important supply scenarios without sacrificing security. The disclosed technology is applicable in drug and food shipments and other types of high value secure supply chains.

INTRODUCTION

The technology disclosed relates to secure blockchain-based systems and methods used for accessing, creating and maintaining block chain validated documents, and more particularly to permissioning actors not credentialed to access block chain by systems and methods using block chain to validate documents in high security, high data integrity applications to provide information to the block chain. Information about exceptions and anomalies can be gathered from actors, human and automaton, that can be either trusted or non-trusted with access to the block chain, stored on the blockchain once validated, and reported to regulatory bodies by multiple actors in a trusted block chain centric network. Some applications relate to pharmaceuticals, artificial heart valves and other compositions, systems and apparatus for medical uses and other high security, high data integrity applications.

Conducting secure, high integrity data operations includes implementations capable of two way authentication between a blockchain application and a human user of a device—for example when a blockchain application sends a request As used herein an Oraculous request can include requests by a block chain application for information pertaining to a current transaction to be preserved in the block chain to an application on a human user's device (e.g. to a known email address or known cell phone number) and the human responds manually by entering appropriate inputs into the application on the device. For example, the blockchain application server sends a request to an authorized Department of Motor Vehicles (DMV) official asking "Did Bob D. Person had a valid driver's license on date YYYY/MM/DD?" and the human user enters data in response.

Conducting secure, high integrity data operations includes implementations capable of two way authentication between a blockchain application and a machine—for example when a blockchain application sends a request to a machine (e.g. to a known endpoint URL using an existing credential authorizing use of that endpoint) and the machine recipient responds automatically. For example, the blockchain application server sends a request to an authorized DMV-run server which can be queried to effectively answer the question "Did Bob D. Person have a valid driver's license on date YYYY/MM/DD?" In one implementation, a determination is made whether the intended recipient is a machine based automaton or a human being viewing the message using his/her device and thereupon decides how to handle sending the request based upon the decision. Automated requests so constructed enable block chain enabled systems to generate queries and gather information for incorporating into the block chain, even from non-credentialed sources, along with pushing block level representations of at least some gathered information into a blockchain network as described in a chain code or a smart contract. The terms chain code and smart contract will be used interchangeably herein.

System Overview

Figure 1B:
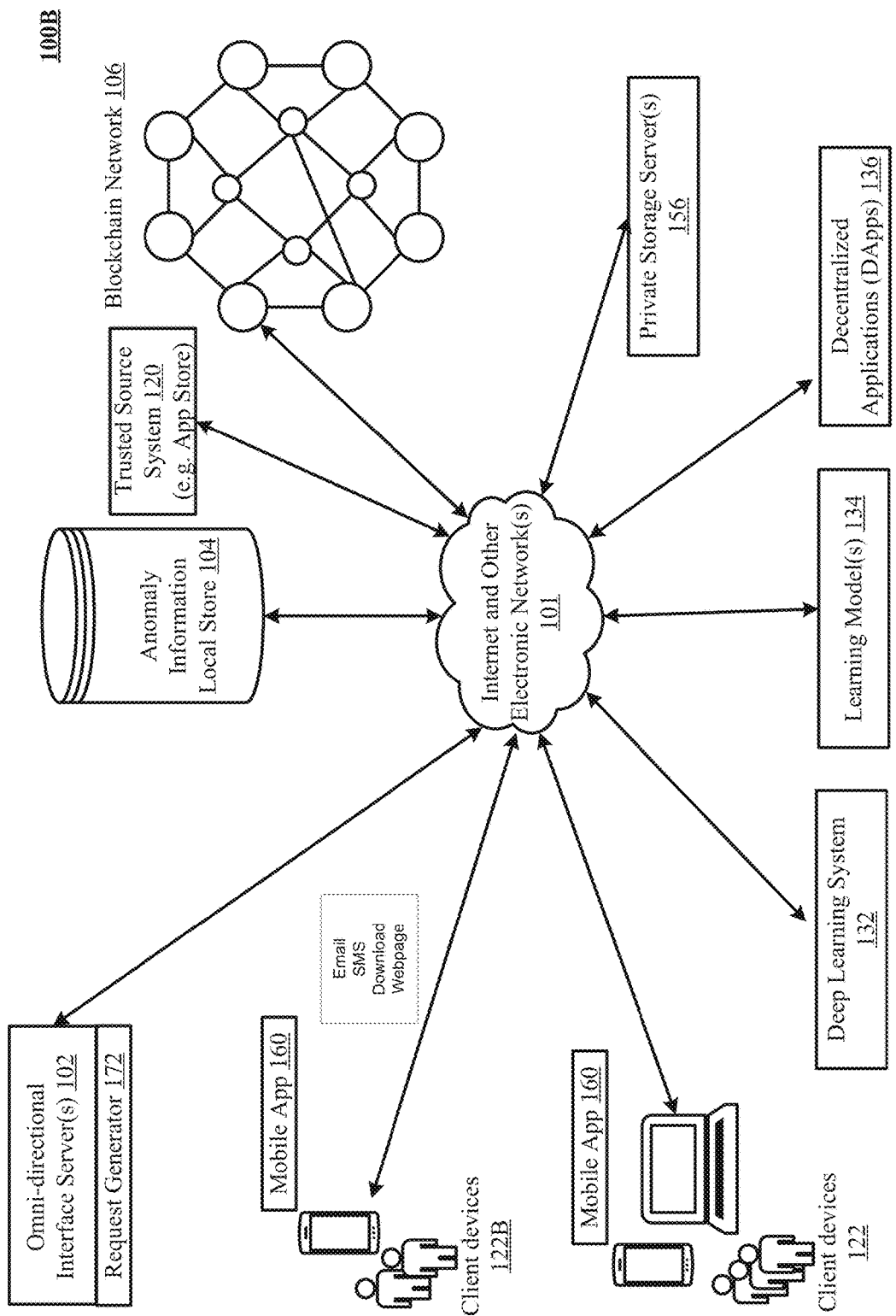
FIG. 1B shows an architectural level schematic of a system 100B that implements technology for establishing trusted relationship(s) between requester(s) and recipient(s) in a blockchain network that is publicly accessible in accordance with another implementation.
Figure 1C:
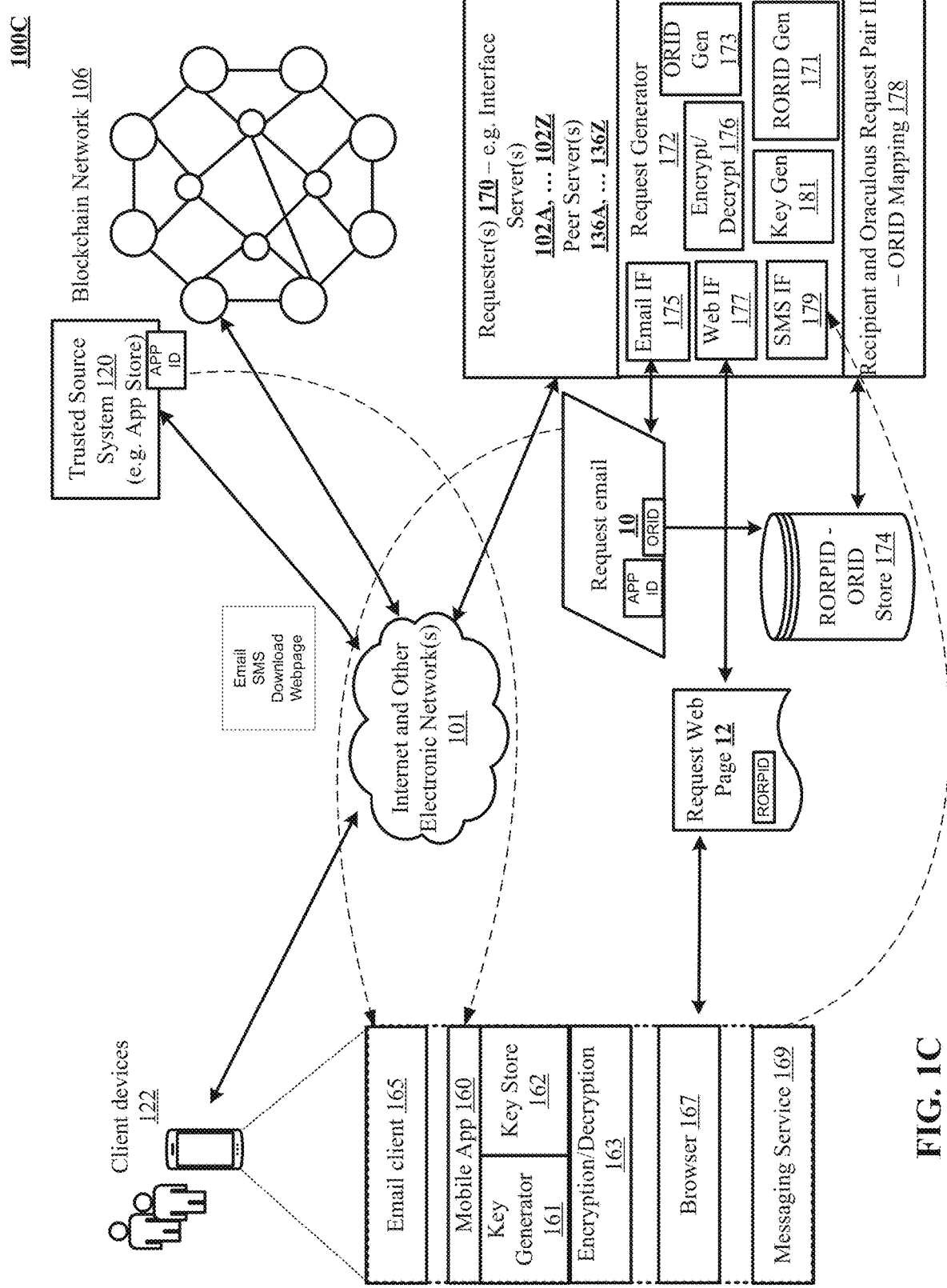
FIG. 1C shows an architectural level schematic of a system 100C that implements technology for establishing trusted relationship(s) between requester(s) and recipient(s) in the blockchain networks of FIGS. 1A and 1B.

The technology disclosed describes system and method implementations of data origin authentication and data requestor authentication for preserving confidentiality and data integrity in block chain centric systems. Implementations establish trusted and semi-trusted relationships (e.g., less than access granted to members having full authority to push or modify data to or on the block chain) with information providers. Implementations further establish trusted and semi-trusted relationships with information requestors. Information gathered from trusted and semi-trusted sources can be pushed as block level representations to the block chain by trusted members having access authority to the block chain thereby creating a blockchain network as described in a smart contract. FIGS. 1A, 1B, and 1C show an architectural level schematic of a system in accordance with an implementation. Because FIGS. 1A, 1B, and 1C are architectural diagrams, certain details are intentionally omitted to improve the clarity of the description.

The discussion of FIGS. 1A, 1B, and 1C will be organized as follows. First, the elements of the figure will be described, followed by their interconnections. Then, the use of the elements in the system will be described in greater detail.

FIG. 1A shows an architectural level schematic of a system 100A that implements technology for establishing trusted relationship(s) between requester(s) and recipient(s) in a blockchain network of trusted actors. The system 100A includes omni-directional interface server(s) 102, anomaly information local store 104, private storage server(s) 156 accessing private collections data stored for each organization, deep learning system 132 can be used to train one or more neural networks or other learning model(s) 134, peer server(s) 136 that also include chain code (or smart contracts) implementing decentralized applications (DApps), ordering server(s) 146, and other servers and other trusted entities 170, not shown by FIG. 1A for clarity sake, that comprise a blockchain network 106, communicatively coupled to one another as well as client devices 122 of non-credentialed users and other entities, by Internet and/or other electronic communications network(s) 101. Pathways for establishing communications between trusted entities 170, such as omni-directional interface server(s) 102, etc. and non-credentialed entities, such as users of client devices 122, are described in further detail herein below with reference to FIG. 1C.

The interconnection of the elements of system 100A will now be described. Network(s) 101 couples the interface server(s) 102, the anomaly information local store 104, with the other servers and other entities that comprise a blockchain network 106, the client devices 122, private storage server(s) 156 accessing private collections data stored for each organization, the deep learning system 132, the learning model(s) 134, peer server(s) 136 that also include chain code (or smart contracts) implementing the DApps, and the ordering server(s) 146, that can be in communication with each other (indicated by solid double-arrowed lines). The actual communication path can be point-to-point over public and/or private networks comprising network(s) 101. The communications can occur over a variety of networks, e.g., private networks, VPN, MPLS circuit, or Internet, and can use appropriate application programming interfaces (APIs) and data interchange formats, e.g., Representational State Transfer (REST), JavaScript Object Notation (JSON), Extensible Markup Language (XML), Simple Object Access Protocol (SOAP), Java Message Service (JMS), and/or Java Platform Module System. At least some of the communications can be encrypted. The communication is generally over a network such as the LAN (local area network), WAN (wide area network), telephone network (Public Switched Telephone Network (PSTN), Session Initiation Protocol (SIP), wireless network, point-to-point network, star network, token ring network, hub network, Internet, inclusive of the mobile Internet, via protocols such as EDGE, 3G, 4G LTE, Wi-Fi, and WiMAX. Additionally, a variety of authorization and authentication techniques, such as username/password, Open Authorization (OAuth), Kerberos, SecureID, digital certificates and more, can be used to secure the communications. The engines or system components of FIGS. 1A, 1B, and 1C such as deep learning system 132, private storage server(s) 156, ordering server(s) 146, peer server(s) 136, the interface server(s) 102, and other trusted entities comprising blockchain network 106 as well as mobile applications 160 of client devices 122 can be implemented by software running on varying types of computing devices. Example server devices are a workstation, a server, a computing cluster, a blade server, and a server farm. Example client devices include a smart phone, smart tablet, laptop computer, wearable smart headset and/or goggles such as GOOGLEGLASS™ and AR/VR headsets such as Oculus GO™ HTC VIVE™, Sony Playstation™ VR and the like.

Interface server(s) 102, associated by a set of trust relationships with peer server(s) 136, and other servers and other entities, comprise the blockchain network 106, that acts as a distributed database or an immutable ledger which maintains records of all electronic transactions conducted by participants such as interface server(s) 102 and peer server(s) 136 in a peer-to-peer network. A blockchain is maintained by a network of nodes (e.g., interface server(s) 102, peer server(s) 136, etc.) where every node executes and records electronic transactions to a particular chain. The blockchain structure is replicated among the nodes in the network. Because blockchain network 106 implements a peer-to-peer network, it does not require a central authority or trusted intermediaries to authenticate or to settle the electronic transactions or control the underlying infrastructure. Examples of popular blockchain platforms include Hyperledger Fabric™, and Hyperledger Corda™, Ethereum™, Eris™, Multichain™, and Bitcoin™. Blockchain network 106 includes a distributed data structure (i.e., a "ledger" or "blockchain ledger") comprising a chain of blocks. Servers implementing nodes of blockchain network 106 can host chain code or "smart contracts". Chain code is a piece of code that resides on blockchain and is identified by a unique address. A chain code includes a set of executable functions and state variables. The function code is executed when transactions are sent to the functions. The transactions include input parameters which are required by the functions in the chain code. Upon the execution of a function, the state variables in the chain code change depending on the logic implemented in the function. Chain code can be written in various high-level languages (such as Golang™ or Solidity™ or Python™). Language-specific compilers for chain code (such as Golang™ or Solidity™ or Serpent™ compilers) are used to compile the chain code into bytecode. Once compiled, the chain code is uploaded to peer server(s) 136 of the blockchain network 106 which assign a unique address to each chain code. In permissioned blockchain systems, such as Hyperledger Fabric™, a node in the network can read electronic transactions for which it has permission. (In other blockchain systems, such as Ethereum™ all transactions are accessible to all nodes.)

The electronic transactions in the blockchain ledger are time-stamped and bundled into blocks where each block is identified by its cryptographic hash. The blocks form a linear sequence where each block references the hash of the previous or parent block, forming a chain of blocks called the blockchain. Each block maintains records of all the transactions on the network received since the creation of its previous block. Instead of storing the information on all the transactions within the block itself, a special data structure called a Merkle tree is used to store the transactions and only the hash of the root of the Merkle tree is stored in the block. Blockchain is an immutable and durable data structure which maintains a record of the transactions that are tamper-resistant. Once a transaction is recorded in a block, it cannot be altered or deleted as long as a majority of the computational power of the network is not controlled by peers who collude to alter the blockchain.

Interface server(s) 102 can leverage blockchain platforms to enable device-to-device and data consumer-to-device electronic transactions. Interface server(s) 102 are preferably configured using application backend code 111 as proxies that have their own blockchain accounts for communicating with peer server(s) 136 in the blockchain network 106 and associated chain code (or smart contracts). The application chain code 112 can store information on the device identities and usage patterns of client devices 122. Chain code versioning 116 keeps chain code of chain code libraries 114 deployed on Interface server(s) 102 compatible with chain code deployed on associated peer server(s) 136, enabling one of the interface server(s) 102 of "Organization A" to send transactions to the associated chain codes deployed on "Organization A" peer server(s) 136A and receive transactions from the peers of Organization A on the blockchain network 106. Application backend code 111 enables this by running a blockchain client on the interface server(s) 102 that uses a controller service to connect the interface server(s) 102 with peer server(s) 136A of Organization A and peer servers 136B of Organization B, as well as any others that interface server(s) 102 are configured to be in a trusted entity with. An example of a blockchain client is Hyperledger Fabric™. (In alternative implementations, an EthJsonRpc Python™ client for Ethereum™ that uses JSON-based remote procedure calls (RPCs) to implement client-specific methods and provides a high-level interface to create smart contracts on Ethereum™ and to call contract functions.)

New blocks are created and added to the blockchain by participants (e.g., interface server(s) 102, peer server(s) 136). In a permissioned blockchain platform, such as Hyperledger Fabric™, access to the blockchain network 106 is restricted only to a set of pre-defined participants. Participants may elect to permit new blocks to be created and added to the chain by any one of them without a consensus (called "No-op") or to be added by meeting an agreement protocol, such as Practical Byzantine Fault Tolerance (PBFT). For example, two or more parties can agree on a key in such a way that both influence the outcome. This precludes undesired third parties from forcing a key choice on the agreeing parties.

FIG. 1B shows an architectural level schematic of a system 100B that implements technology for establishing trusted relationship(s) between requester(s) and recipient(s) in a blockchain network that is publicly accessible in accordance with another implementation. A public or private without permissions blockchain platform, such as Ethereum™, can be suited for implementing the disclosed technology also. The process of adding blocks to the blockchain in a public or private without permissions blockchain platform is called mining. As shown in FIG. 1B, a plurality of distributed applications 136B hosted on server(s) that are decentralized in nature, with no single entity or organization controlling the infrastructure on which the blocks are stored. FIG. 4B is a block diagram 400B with an example distributed application(s) 136B that can be used to host smart contracts that implement nodes in the blockchain network that perform the mining operations are called miners. New transactions are broadcast to all the nodes on the network. Each miner node creates its own block by collecting the new transactions and then finds a proof-of-work (PoW) for its block by performing complex cryptographic computations. The miners validate the transactions and reach a consensus on the block that should be added next to the blockchain. The newly mined block, called the winning block, is then broadcast to the entire network. The winning block is the one that contains a PoW of a given difficulty.

While each miner on the blockchain network 106 can create its own block, only the block which has a PoW of a given difficulty is accepted to be added to the blockchain. The consensus mechanism ensures that all the nodes agree on the same block to contain the canonical transactions. Blockchain offers enhanced security as compared to centralized systems as every transaction is verified by multiple miners. The integrity of the transaction data recorded in the blocks is protected through strong cryptography. In addition to the transaction data, each block contains a cryptographic hash of itself and the hash of the previous block. Any attempts to modify a transaction would result in a change in the hash and would require all the subsequent blocks to be recomputed. This would be extremely difficult to achieve as long as the majority of miners do not cooperate to attack the network.

With renewed reference to FIG. 1A, in implementations, data too sensitive to risk being stored directly on the blocks of the blockchain network 106 can be stored locally in local store(s) 104. For example, medical privacy laws such as health insurance portability and accountability act (HIPAA), general data protection regulation (GDPR), and others, legal, regulatory or private, place restrictions on the usage and keeping of data. In such cases, information can be stored locally by participants in the blockchain network 106 in local store(s) 104. Addressing information can be pushed by the custodian of the locally stored data, typically in encrypted or other non-human readable form to provide protection from tampering by a single actor and provides for data confidentiality with encryption at the block level.

When client devices 122 wish to avail the services of the interface server(s)102, these devices execute application software implementing web applications, mobile applications 160, event subscriber (user, automation, business applications), automated applications and the like to authenticate with user authentication code 113. Once authenticated using the processing described hereinbelow with reference to FIGS. 2A and 3A, the authenticated device is enabled to conduct data transactions via the chain code 112 associated with the interface server(s) 102, including responding to Oraculous requests to provide information generated by request generator 172. The interface server 102, will obtain services on behalf of the authenticated device, effectively blocking direct linking between user device and nodes in the block chain. For example, one of the client devices 122 accesses the system using an application deployed on a workstation or mobile devices and driven by the interface server(s) 102 accessed over network 101. The mobile application, when backed by the interface server(s) 102, reads barcodes on questionable package and gathers user information enabling the interface server(s) 102 to obtain using neural networks implementing learning models 134 diagnostic information and applications that can trigger remedial action, such as completing a discrepancy report. One implementation can enable photos of barcodes to be taken by a third party, optical character recognition of the human-readable label, and XML or other machine files with the same information. One implementation provides pill recognition using image recognition driven CNN classifiers of learning models 134 trained using ground truth training sets drawn from publicly available and/or other image recognition frameworks. One implementation provides client devices 122 at the reporting party with a series of learning model 134 selected modal screens, enabling client devices 122 to accurately and rapidly notify regulators and counter-parties ("trading partners") of problems.

Ordering server(s) 146 are used by interface server(s) 102 to request transactions with the peer server(s) 136 to retrieve or store information, such as anomaly reports, to the block chain ledger. In this manner the identities of the peer server(s) 136 are anonymized and known to the ordering server(s) 146 in the tamper-proof blockchain network 106.

Private storage server(s) 156 access private collections data stored for each organization, which may comprise information of various drug databases (e.g., the FDA Product-Specific Guidance database, which enables searching and clustering by active ingredient(s)) and communications including machine reading of emails on recalls. Interface server(s) 102 is cooperatively coupled with private storage server(s) 156 that can comprise multiple sources of data stored by individual organizations that are members of the blockchain network 106, thereby minimizing the need to change notification protocols that can be related to machine-readable data and image recognition (e.g. images of pills).

Learning model(s) 134 in conjunction with event hub 115 enable interface server(s) 102 to apply machine learning techniques (cluster identification, free form input learning) to observational global state of the block level events in the block chain, input of responses to follow-up questions obtained from user responses and actions, to identify anomalies, and decide when to gather additional information and/or filing a report to another entity in the blockchain network 106. Learning model(s) 134 implement unsupervised and transitioning to semi-supervised machine learning techniques, thereby enabling (re-)training and refinement to occur.

In one implementation, learning model(s) 134 implement multi-layer ensembles of neural subnetworks includes a first anomaly subnetwork, and a second solution accessibility subnetwork. The learning model(s) 134 are further configured to classify inputs indicating various anomalous sensed conditions into probabilistic anomalies using a first anomaly subnetwork. Determined probabilistic anomalies may be classified into remedial application triggers. Remedial application triggers are invoked to recommend or take actions to remediate, and/or report the anomaly. One implementation the learning model(s) 134 can select a report type to submit based upon the situation state. One implementation can select a report recipient based upon the situation state. For example within the drug and healthcare reporting field, learning model(s) 134 can address reporting among both professionals and consumers: FDA: Field Alert Report (FAR), FDA: Biological Product Deviation Report (BPDR), FDA: Form 3500 (Medwatch, voluntary reporting by healthcare professionals, consumers, and patients), FDA: Form 3500A (Medwatch, mandatory reporting by IND reporters, manufacturers, distributors, importers, and user facilities personnel), FDA: Form 3500B (Medwatch, voluntary reporting by consumers), FDA: Reportable Food Registry, FDA: Vaccine Adverse Event Reporting System (VAERS), FDA: Investigative Drug/Gene Research Study Adverse Event Reports, FDA: Potential Tobacco Product Violations Reporting (Form FDA 3779), USDA *APHIS* Center for Veterinary Biologics Reports, USDA Animal and Plant Health Inspection Service: Adverse Event Reporting, USDA FSIS Electronic Consumer Complaints, DEA Tips, Animal Drug Safety Reporting, Consumer Product Safety Commission Reports, State/local reports: Health Department, Board of Pharmacy, and others.

The deep learning system 132 trains some of the learning model(s) 134 implementing neural networks in semi-supervised modalities to recognize anomalies and trigger remedial actions. In one implementation, neural networks are trained on one or more training servers (e.g., 1302 of FIG. 13C) using training datasets (e.g., 1312 of FIG. 13C) and deployed on one or more production servers (e.g., 1304 of FIG. 13C). For additional description of deep learning system 132 and learning model(s) 134, the skilled person can have reference to commonly owned, copending U.S. Non-Provisional patent application Ser. No. 16/740,348, titled "Neural Network Classifiers for Block Chain Data Structures", filed Jan. 10, 2020, the entirety of which is incorporated herein by reference for all purposes.

FIG. 1C shows an architectural level schematic of a system 100C that implements technology for establishing trusted relationship(s) between requester(s) and recipient(s) in the blockchain networks of FIGS. 1A and 1B. The components and subcomponents of the entities making up the implementation depicted in FIG. 1C will be described in relation to one another. Then, operation of these entities will be described below with further reference to FIGS. 2A and 3A. The system 100C includes requesters 170, which can comprise omni-directional interface server(s) 102, peer server(s) 136 that also include chain code (or smart contracts) implementing decentralized applications (DApps), ordering server(s) 146, private storage server(s) 156 accessing private collections data stored for each organization, as well as other servers and other entities that comprise a blockchain network 106, any of which can make requests of client devices 122, that do not have access to the blockchain network 106 using the two-way multiple modality cross-authentication technology implementing user authentication 113 and described herein below with reference to FIGS. 2A and 3A. deep learning system 132 can be used to train one or more neural networks or other learning model(s) 134, and Internet and/or other electronic communications network(s) 101.

Requester 170 includes a request generator 172. Request generator 172 includes program logic that creates a request to a non-credentialed recipient soliciting information. In an implementation the request is structured to include a means of authenticating the source of the request, the requester 170 to the recipient of the request.

Request Modalities

In an example embodiment illustrated by FIG. 1C, request generator 172 of a typical requester generates a request 10 as an email using email IF 175. Implementations can, however, generate requests in a variety of modalities, including mixtures of modalities, such as without limitation: (i) email sent to an email address; (ii) push notification sent to a phone number (note that push notifications are not 100% reliable, i.e. a push notification may silently fail to be delivered); (iii) automated phone call made to phone number, employing either additional infrastructure or the use of third-party services; (iv) combinations of (i)-(iii); (v) others.

Two-Way Authentication

In one implementation, request email 10 includes a link (APP ID) identifying a mobile application stored with a trusted source 120, such as an app store provided by a trusted third party (e.g., Apple App Store™, Google Play Store™, etc.) that the recipient device 122 can download and install as mobile application 160; and (ii) a randomized unique identifier (ORID) generated by ORID generator 173 and associated by request generator 172 with request 10 for information that identifies the request 10 to the mobile application 160 once installed. Noteworthy, because the recipient device 122 retrieves his copy of the mobile application 160 from a trusted source 120, i.e., the app store, the mobile application is authentic, and the sender of the request is authentic. Noteworthy is that the mobile application 160 presence in the trusted source 120 is what is providing the authentication to the recipient; in other words, an attacker would not be able to put a fake "look-a-like" in the trusted source 120 (e.g., app store). Using the mobile application 160, the user of device 122 can view links to requests that the mobile application has received, and can open a received request link including a random ID (ORID) generated by ORID generator 173 and associated by request generator 172 with request 10 for information.

An SMS IF 179 in conjunction with messaging service 169 of device 122 enables request generator 172 to obtain a second factor authorization of the device 122 once the mobile application 160 is installed by the user of the device 122. While illustrated by an example using SMS in FIG. 1C, implementations can employ any of a variety of different types of two-factor authorizations having different security levels and requirements for advance setup. The choice of which one to use will depend on app specific and use-case-specific considerations. Types of two-factor authorizations that could be used: (i) one-time code sent to email address—no credentials does not require recipient to possess credentials; (ii) one-time code sent to phone number via push notification—does not require recipient to possess credentials; (iii) one-time code sent encrypted to email address—a public encryption key of the recipient must be known in advance, though this could be specified alongside the recipient email address; (iv) time-based code with shared secret (e.g. Google Authenticator™)—requires recipient to set up the shared secret in advance. Once this second verification processing is complete, the request recipient device 122 has authenticated to the requester 170, and therefore the two-way authentication is complete.

Encryption/decryption 163, key generator 161 and key store 162 of mobile application 160 installed on device 122 and corresponding encryption/decryption 176, key generator 181 and key store 182 of request generator 172 enable corresponding pairs of public and private key pair to be generated by each of the mobile application 160 and the requester 170 and the public keys exchanged. These are the credentials that will be used between these two entities for two-way authentication. In one implementation, the keys are exchanged using Email. In another implementation, keys are exchanged using direct communications between application and server. Once exchanged, keys can be used to pass encrypted traffic between requester and application.

It is noteworthy that in an implementation, when a recipient has already performed actions of installing the mobile application and mutually authenticating application 160 and requester 170, then a notification can be sent directly to the mobile application 160, bypassing the need for switching between email 10 and mobile application 160.

Oracle Request Processing

Once authenticated, the mobile application 160 opens the embedded link in the request 10 in the mobile device's web browser 167. The link includes an auth-token (RORPID) that is unique to that request and that authentication. The RORID generator 171 of the request generator 172 creates the RORPID. The RORPID is embedded into the request link of a request web page 12 and sent to the mobile application 160 by web IF 177. The mobile application 160 can open the link accompanying the RORPID in the browser 169 of the device 122, enabling the recipient to enter the requested information into appropriate fields in the request web page 12. When complete, the information entered is forwarded to the web IF 177 of the request generator 172 of requester 170. The requester 170 commits some information from the request to the blockchain 106.

A recipient and request pair ID-ORID mapping 178 enables multiple requests to be sent to multiple recipients, wherein each is a unique entity in the blockchain ecosystem. The link sent to each recipient should be different, each one containing a unique identifier which can be tied uniquely to that recipient and can be mapped uniquely to that request. This way, the identity of the recipient who is responding is known. When combined with uniqueness of the ORID described above, this criterion provides for a random, unique "Recipient and Oraculous Request Pair ID" (call this ROR-PID for brevity). Implementing a randomness criterion ensures that the ORID itself does not expose information about the underlying components of the system, as is the case with the ORID. In particular, the RORPID should not be a function of the ORID, as this would expose such information.

A RORPID-ORID store 174 persistent storage is accessible to the requester(s) 170 and stores in persistent storage a variety of data for preserving the integrity of the requests, recipients and other information. For example, a mapping from RORPID to ORID (i.e. the mapping from a recipient and request pair to its corresponding request) can be maintained in the RORPID-ORID store 174 persistent storage. The mapping from RORPID to recipient identity—a recipient identity is a record which defines the recipient's medium of request, two factor authentication, and any other relevant context—can be maintained in the RORPID-ORID store 174 persistent storage. The mapping from ORID to the set of corresponding RORPIDs (i.e. the mapping from an request to the set of its recipient and request pairs) can be maintained in the RORPID-ORID store 174 persistent storage. The RORPID-ORID store 174 persistent storage can also store other relevant data regarding each request tracked, such as without limitation: (i) issue timestamp; (ii) expiration timestamp; (iii) other necessary use-case-specific context for the request; (iv) other relevant data regarding each recipient of a request, e.g., (i) any request-specific context that is specific to this recipient.

Removing Authentications

In an implementation, authentication of the user's mobile application is terminated by command of the server when information needed by the server is gathered and the trusted conversation is completed. In some implementations, the authentication of the user's mobile application is terminated based upon expiry of a time limit to respond. In some implementations, the authentication of the user's mobile application is terminated based upon expiry of a time limit defining a maximal length that authentications can persist. In some implementations, a user of an installed application and re-authenticate with the trusted server. In some implementations, the trusted server resends the request for information to the non-credentialed device as an authorized recipient upon expiry of a time limit to respond.

Failed Authentications

Some implementations will limit the number of attempts for performing two-factor authentication. For example, some implementations may place a limit on the number of failed attempts to authenticate in response to a request. This limit can be made preferably per RORPID (i.e. per recipient, per request), so that if the limit is 10 attempts, a rogue wave of 10 legitimate recipients all getting the authentication wrong once, but in good faith, does not trigger the limitation. Implementations can include a variety of actions to be taken should the limit be exceeded or authentication otherwise fails, such as for example any or combination(s) of: (i) log the triggering offense; (ii) invalidate that request; (iii) ban the IP address of the offender for a period of time, e.g., 10 or greater minutes; (iv) flag the offending recipient as potentially compromised; (v) notify some security admin that some unusual activity is occurring; (vi) if the request pertains to some business arrangement, initiate human contact with the business to see whether something has gone wrong, and potentially to change the email address/cell phone number used as the recipient.

Invalidating an Existing Request

In one implementation, a request can be canceled or revoked by the application server 102. For example, a user initiating cancelling a request is first authenticated and checked for appropriate authority to cancel the request (e.g., user has full credentials on the app server and is authorized to make such an invalidation). Such an invalidation should (unless explicitly blocked by app-specific or use-case-specific configuration) send a notification to the recipients' devices 122 of the invalidated request. In an example scenario, if the request solicited information for: "can you verify the date that XYZ occurred?" but there was some error in the request itself, such as XYZ not having occurred, or XYZ is not the correct fact that occurred, and the issuer of the request wanted to "retract" the request before any recipient responded to it.

In a yet further implementation, a mechanism is provided on the "landing page" of a live request—this would be the landing page that a recipient would see when responding—that to ask that that request be invalidated. For example, the recipient pre-empting an error condition by asking for invalidation. An example of this scenario could be if the request solicited, "what is the car insurance policy number for the car with this license plate number?", an invalidation request could be issued with reason "you have the wrong license plate number, so the question itself is moot.").

Expired Requests

In one implementation, any attempt to open an expired verification request is captured by the request generator 172 and an error handling sequence of actions can be initiated. For example, one error sequence would present a page saying something to the effect of "this verification request has expired—sending a fresh request to the appropriate recipients." Other error handing sequences can include:

Having presented a system overview, the discussion now turns to establishing a learning model to recognize reportable anomalies and trigger remedial actions.

Other implementations may include a non-transitory computer readable storage medium storing instructions executable by a processor to perform actions of the system described above. Yet another implementation may include a method performing actions of the system described above.

Having described permissioned blockchain ecosystem, the discussion now turns to two-way authentication implementations.

Cross Authentication Processes

Figure 2A:
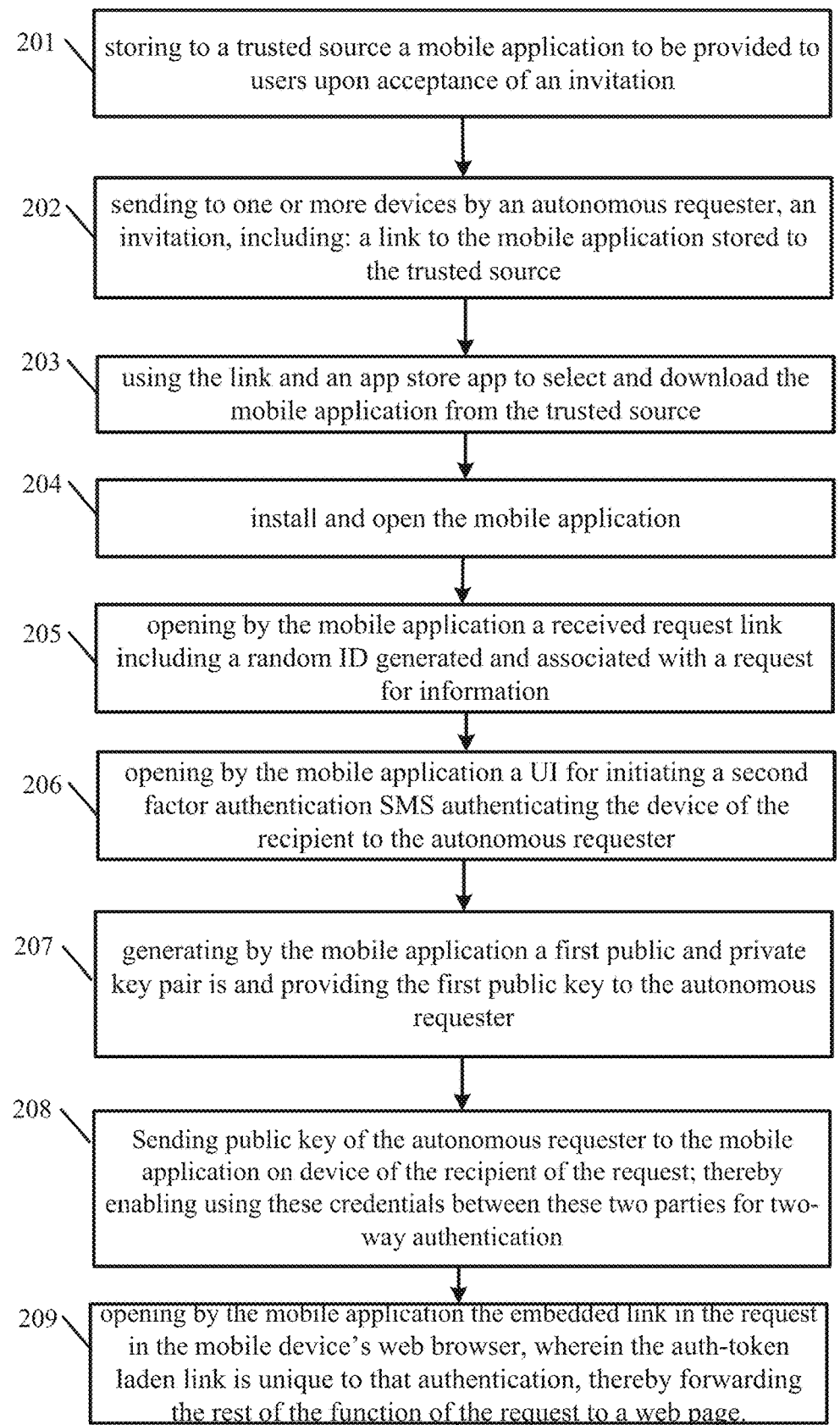
FIG. 2A is a flowchart illustrating a method for establishing trusted relationship(s) between requester(s) and recipient(s) in a blockchain network implementing event detection, tracking and management for rule-based compliance, according to various embodiments.
Figure 3:
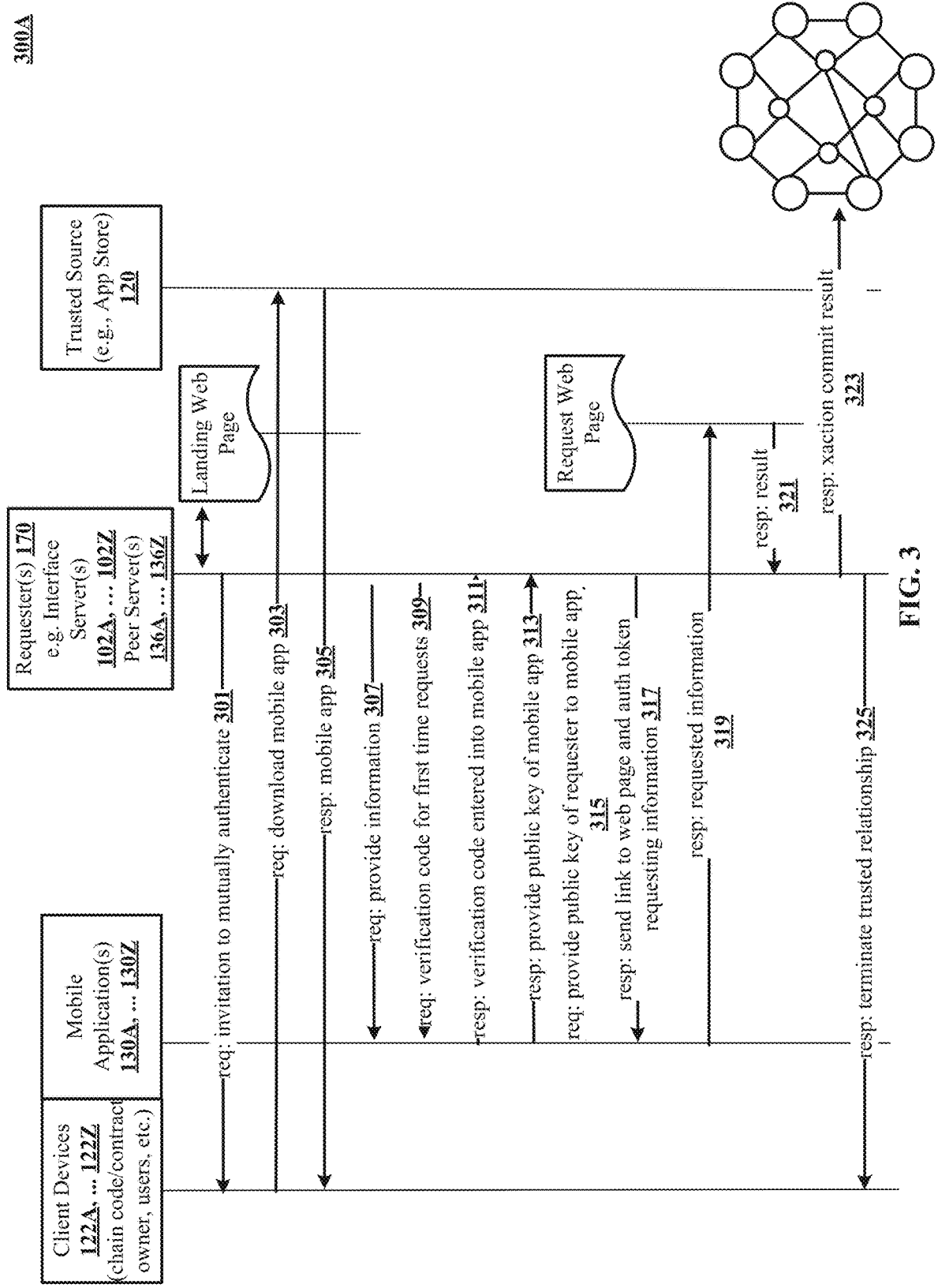
FIG. 3 is a flow diagram 300A depicting flows for establishing trusted relationship(s) between requester(s) and recipient(s) in the technology of FIG. 1C.

Trusted communications in the blockchain ecosystem 100A, 100B of FIGS. 1A and 1B can be based upon a two-way authentication process, an example of which will be described with reference to FIG. 2A, a flowchart illustrating a method for establishing trusted relationship(s) between requester(s) and recipient(s) in a blockchain network implementing event detection, tracking and management according to various embodiments, and FIG. 3, a flow diagram 300A depicting flows for establishing trusted relationship(s) between requester(s) and recipient(s) in the technology of FIG. 1C.

Accordingly, in the flowchart 200A, at block 201, a mobile application 160 is stored to a trusted source 120 (e.g., an app store) to be provided to users upon acceptance of an invitation.

In an two-way authentication process block 202 of flowchart 200A and flow 301 of flow diagram 300A, an autonomous requester 170 (e.g., 102A, . . . 102Z, 136A, . . . 136Z of FIG. 1A, FIG. 1B) sends a request 10 to a client device(s) 122 (belonging to a human recipient(s)). Email is chosen as the vehicle for sending this request, however other channels of Networks 101, e.g., SMS, HTTPS, etc. are also available. As also shown by FIG. 1C, the request 10 includes: (i) a link to the mobile application provided in the trusted source system 120 (e.g., app store); and (ii) a link including a random ID (ORID) generated by ORID generator 173 and associated by request generator 172 with request 10 for information.

In block 203 and flow 303, device 122 uses the link and an app store app to select and download the mobile application from the trusted source. Accordingly, because the recipient retrieves his copy of the mobile application 160 from a trusted source 120, i.e., the app store, the mobile application is authentic, and the sender of the request is authentic. Noteworthy is that the mobile application 160 presence in the trusted source 120 is what is providing the authentication to the recipient; in other words, an attacker would not be able to put a fake "look-a-like" in the trusted source 120 (e.g., app store).

In block 204 and flow 305 the user installs and opens the mobile application 160 to the device 122.

In block 205 and flow 307, the mobile application opens a received request link including a random ID (ORID) generated by ORID generator 173 and associated by request generator 172 with request 10 for information.

In block 206, and flow 309, the mobile application opens a UI for initiating a second factor authentication (e.g., SMS, telephone call/message, software application, webpage, push notification, email, other side channel or combinations thereof) authenticating the device of the recipient to the autonomous requester 170. The mobile application 160 implements, by presenting a UT to the recipient of the request, a second factor authentication of the recipient to the autonomous requester 170. In an example implementation, when the mobile application 160 is downloaded and run for the first time, opening a request link from a particular requester 170 (some implementations include multiple servers, controlled by different organizations, each sending requests), the mobile application can present the UI for the second factor of authentication, such as e.g. a one-time verification code sent by SMS or telephone call or email. In flow 311, the verification code entered by the user is sent by the mobile application 160 to the requester 170 for authentication. Once this second verification processing is complete, the request recipient has authenticated to the requester 170, and therefore the two-way authentication is complete. The mobile application user can authenticate themselves to the trusted server using any of a variety of techniques such as entry of a passphrase, or certification credential (license information, professional identifier, PIN or other unique code, passphrase, or other credential uniquely identifying the user). Some implementations include checking against a whitelist/blacklist. Some implementations will include prompting for and saving biometric information of the user. In some applications, biometric application is stored by the user on the user's device, and the application request authentication of the user via an operating system facility provided by the mobile device, thereby safeguarding the user's privacy. In some applications, if the user's phone is lost or stolen, authentication is invalidated.

In block 207, public and private key pair is generated by the mobile application and the public key is provided to the requester 170.

In block 208, the public key of the requester 170 is received by the mobile application on behalf of the recipient of the request. These are the credentials that will be used between these two entities for two-way authentication. In some implementations, the keys are used to pass encrypted traffic between requester and application. In some implementations, the keys are used to authenticate the user and server to one another.

In block 209 and flow 317, the mobile application 160 opens the embedded link in the request in the mobile device's web browser 167. The link includes an auth-token (RORPID) that is unique to that request and that authentication. In flow 319, the recipient can enter the requested information into appropriate fields in the request web page 12. When complete, the information is forwarded in flow 321 to the web IF 177 of the request generator 172 of requester 170. In flow 323, the requester 170 commits some information from the request to the blockchain 106.

It is noteworthy that in an implementation, when a recipient has already performed actions of blocks 202-208 installing the mobile application and mutually authenticating application and requester, then a notification can be sent directly to the mobile application 160, bypassing the need for switching between email 10 and mobile application 160. One mobile application 160 implementation can present UI for viewing all mutually authenticated requesters, all pending requests, closed requests, etc. Accordingly, implementations of the described technology enable the mobile application 160 to provide portal functionality to the permissioned blockchain ecosystem for the recipient not otherwise authorized to access the blockchain 106 directly.

Having described two-way authentication and messaging operations in a permissioned blockchain ecosystem, the discussion now turns to smart contract implementations.

Use Cases: Finding Like Events

Figure 2B:
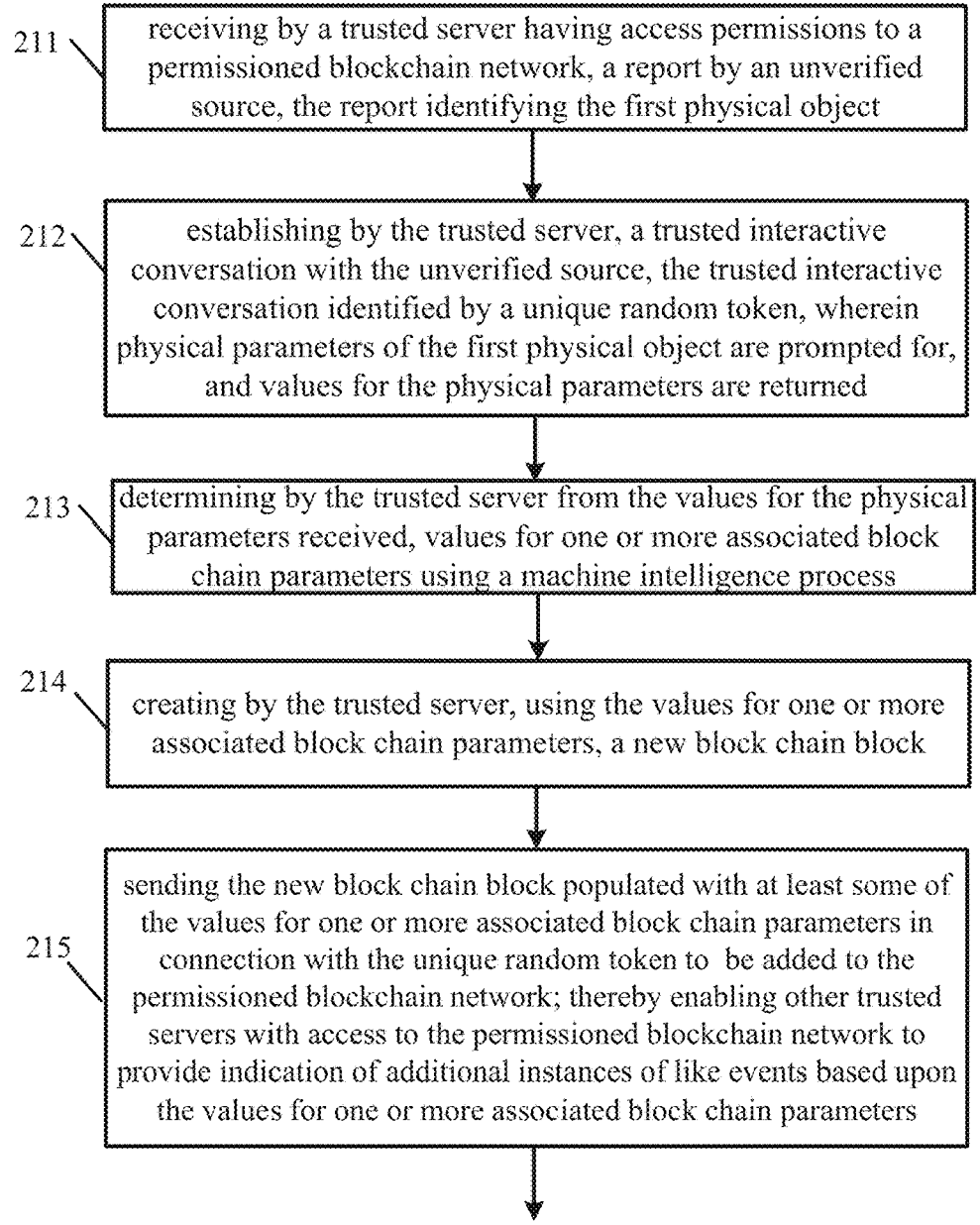
FIG. 2B is a flowchart illustrating a method for finding additional instances of like events from a reported first event involving a first physical object in a blockchain network implementing event detection, tracking and management for rule-based compliance leveraging establishing trusted relationship(s) between requester(s) and recipient(s), according to various embodiments.

Features and functionality of trusted communications in the blockchain ecosystem 100A, 100B of FIGS. 1A, 1B and 1C implementing a two-way authentication process, can be further understood using an example use case that will be described with reference to FIG. 2B, a flowchart illustrating a method for finding additional instances of like events from a reported first event involving a first physical object in a blockchain network implementing event detection, tracking and management for rule-based compliance leveraging establishing trusted relationship(s) between requester(s) and recipient(s), according to various embodiments.

Accordingly, in the flowchart 200B, at block 211, a trusted server having access permissions to a permissioned blockchain network, receives a report by an unverified source, the report identifying the first physical object.

In a block 212, the trusted server establishes a trusted interactive conversation with the unverified source, the trusted interactive conversation identified by a unique random token, wherein physical parameters of the first physical object are prompted for, and values for the physical parameters are returned.

In a block 213, the trusted server determines from the values for the physical parameters received, values for one or more associated block chain parameters using a machine intelligence process.

In a block 214, the trusted server, using the values for one or more associated block chain parameters, creates a new block chain block.

In a block 215, the trusted server sends the new block chain block populated with at least some of the values for one or more associated block chain parameters in connection with the unique random token to be added to the permissioned blockchain network; thereby enabling other trusted servers with access to the permissioned blockchain network to provide indication of additional instances of like events based upon the values for one or more associated block chain parameters.

Figure 2C:
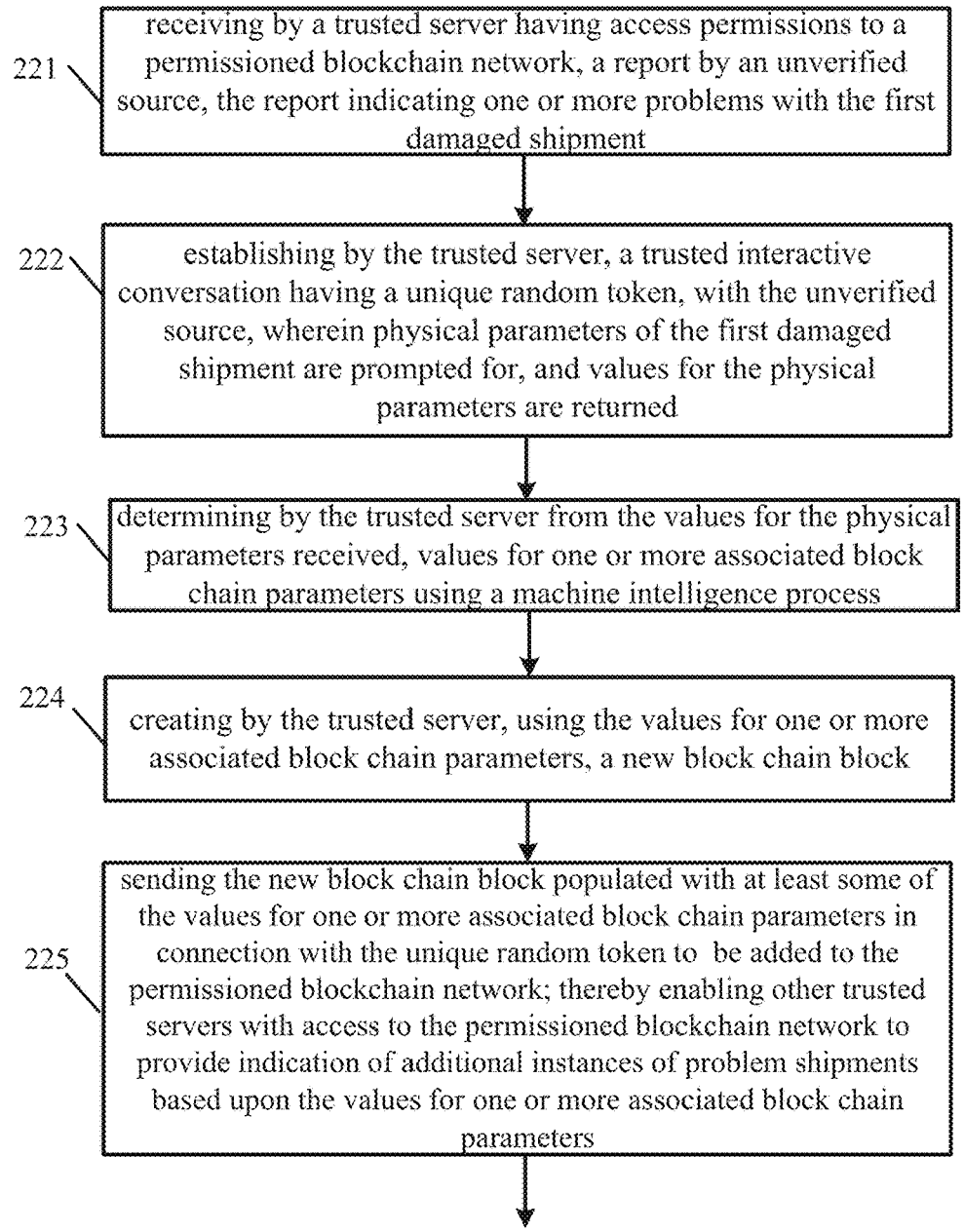
FIG. 2C is a flowchart illustrating a method for finding additional instances of problem shipments from a problem report of a first damaged shipment in a blockchain network implementing event detection, tracking and management for rule-based compliance leveraging establishing trusted relationship(s) between requester(s) and recipient(s), according to various embodiments.

In a further example use case, the features and functionality of trusted communications in the blockchain ecosystem 100A, 100B of FIGS. 1A, 1B and 1C implementing a two-way authentication process, can be further understood with reference to FIG. 2C, a flowchart illustrating a method for finding additional instances of problem shipments from a problem report of a first damaged shipment in a blockchain network implementing event detection, tracking and management for rule-based compliance leveraging establishing trusted relationship(s) between requester(s) and recipient(s), according to various embodiments.

Accordingly, in the flowchart 200C, at block 221, a trusted server having access permissions to a permissioned blockchain network, receives a report by an unverified source, the report indicating one or more problems with the first damaged shipment.

In a block 222, the trusted server establishes a trusted interactive conversation with the unverified source, the trusted interactive conversation identified by a unique random token, wherein physical parameters of the first damaged shipment are prompted for, and values for the physical parameters are returned.

In a block 223, the trusted server determines from the values for the physical parameters received, values for one or more associated block chain parameters using a machine intelligence process.

In a block 224, the trusted server, using the values for one or more associated block chain parameters, creates a new block chain block.

In a block 225, the trusted server sends the new block chain block populated with at least some of the values for one or more associated block chain parameters in connection with the unique random token to be added to the permissioned blockchain network; thereby enabling other trusted servers with access to the permissioned blockchain network to provide indication of additional instances of problem shipments based upon the values for one or more associated block chain parameters.

Figure 2D:
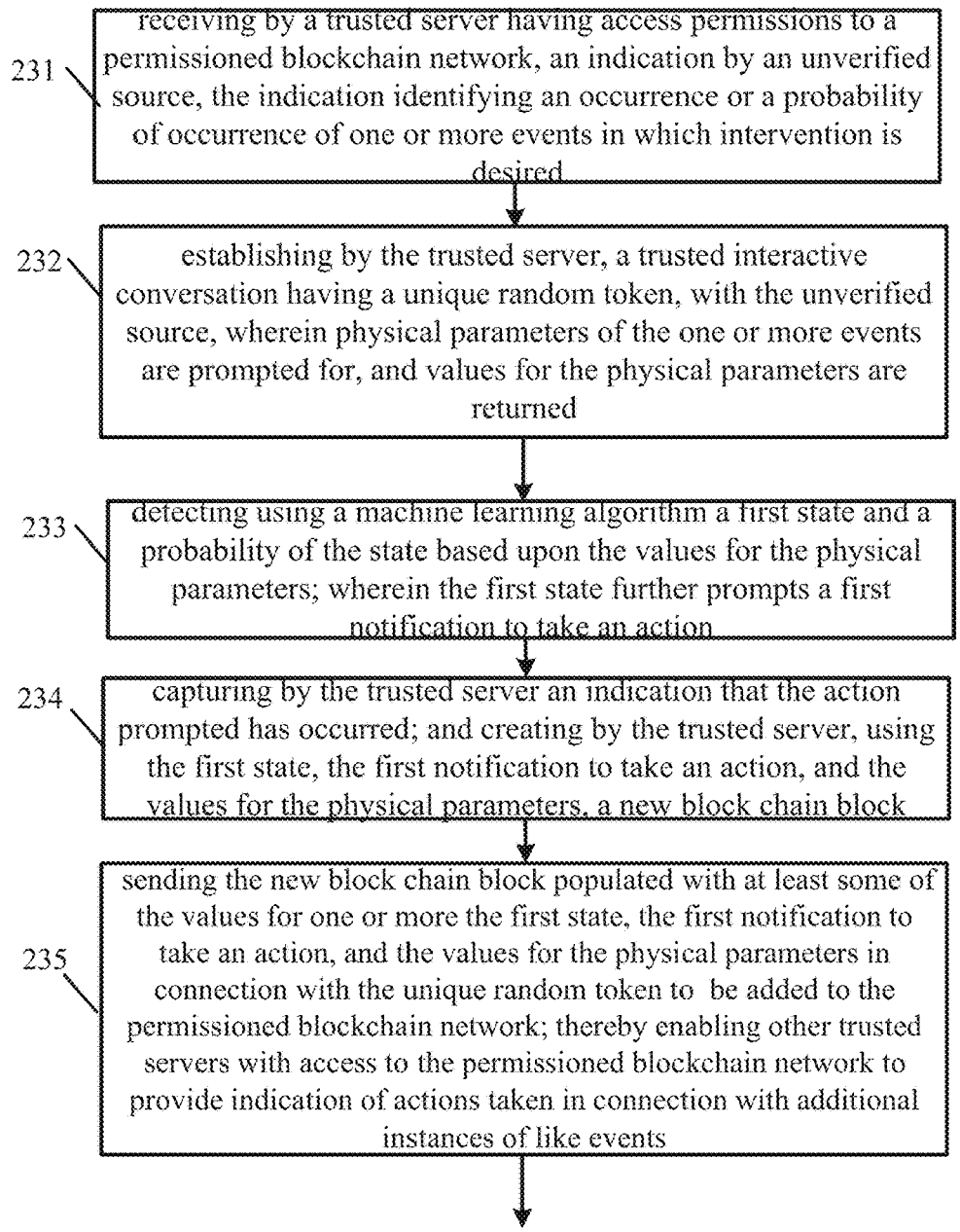
FIG. 2D, a flowchart illustrating a method for initiating commanded actions responsive to reported events in which intervention is desired in a blockchain network implementing event detection, tracking and management for rule-based compliance leveraging establishing trusted relationship(s) between requester(s) and recipient(s), according to various embodiments.

In another example use case, the features and functionality of trusted communications in the blockchain ecosystem 100A, 100B of FIGS. 1A, 1B and 1C implementing a two-way authentication process, can be further understood with reference to FIG. 2D, a flowchart illustrating a method for initiating commanded actions responsive to reported events in which intervention is desired in a blockchain network implementing event detection, tracking and management for rule-based compliance leveraging establishing trusted relationship(s) between requester(s) and recipient(s), according to various embodiments.

Accordingly, in the flowchart 200D, at block 231, a trusted server having access permissions to a permissioned blockchain network, receives a report by an unverified source, the report indicating one or more problems with the first damaged shipment.

In a block 232, the trusted server establishes a trusted interactive conversation with the unverified source, the trusted interactive conversation identified by a unique random token, wherein physical parameters of the first damaged shipment are prompted for, and values for the physical parameters are returned.

In a block 233, the trusted server determines from the values for the physical parameters received, values for one or more associated block chain parameters using a machine intelligence process.

In a block 234, the trusted server, using the values for one or more associated block chain parameters, creates a new block chain block.

In a block 235, the trusted server sends the new block chain block populated with at least some of the values for one or more associated block chain parameters in connection with the unique random token to be added to the permissioned blockchain network; thereby enabling other trusted servers with access to the permissioned blockchain network to provide indication of additional instances of problem shipments based upon the values for one or more associated block chain parameters.

Blockchain-Based Chain Code/Smart Contract

Figure 4A:
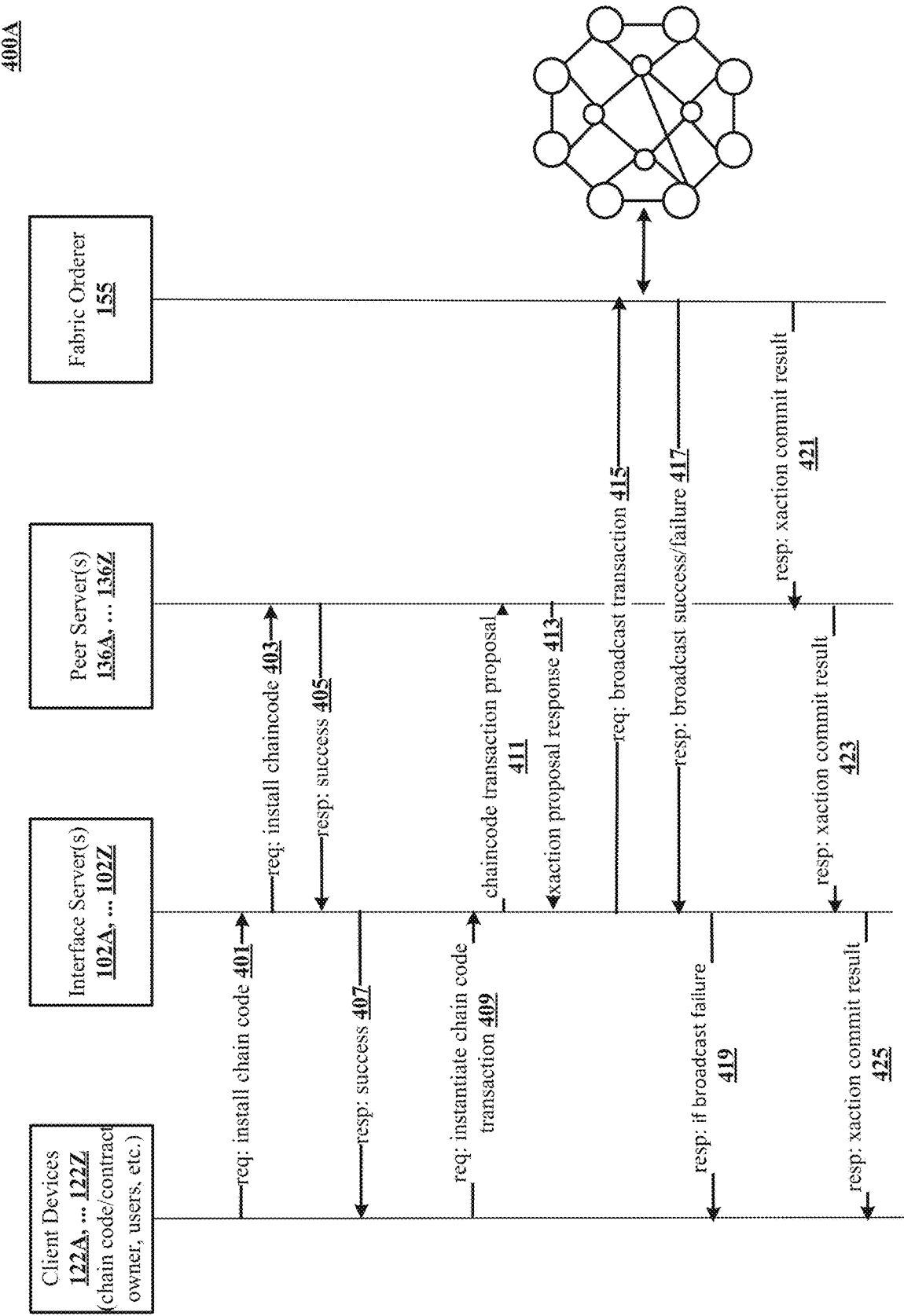
FIG. 4A is a flow diagram 400A depicting an example permissioned blockchain transactions that can be used to implement the technology disclosed.
Figure 4B:
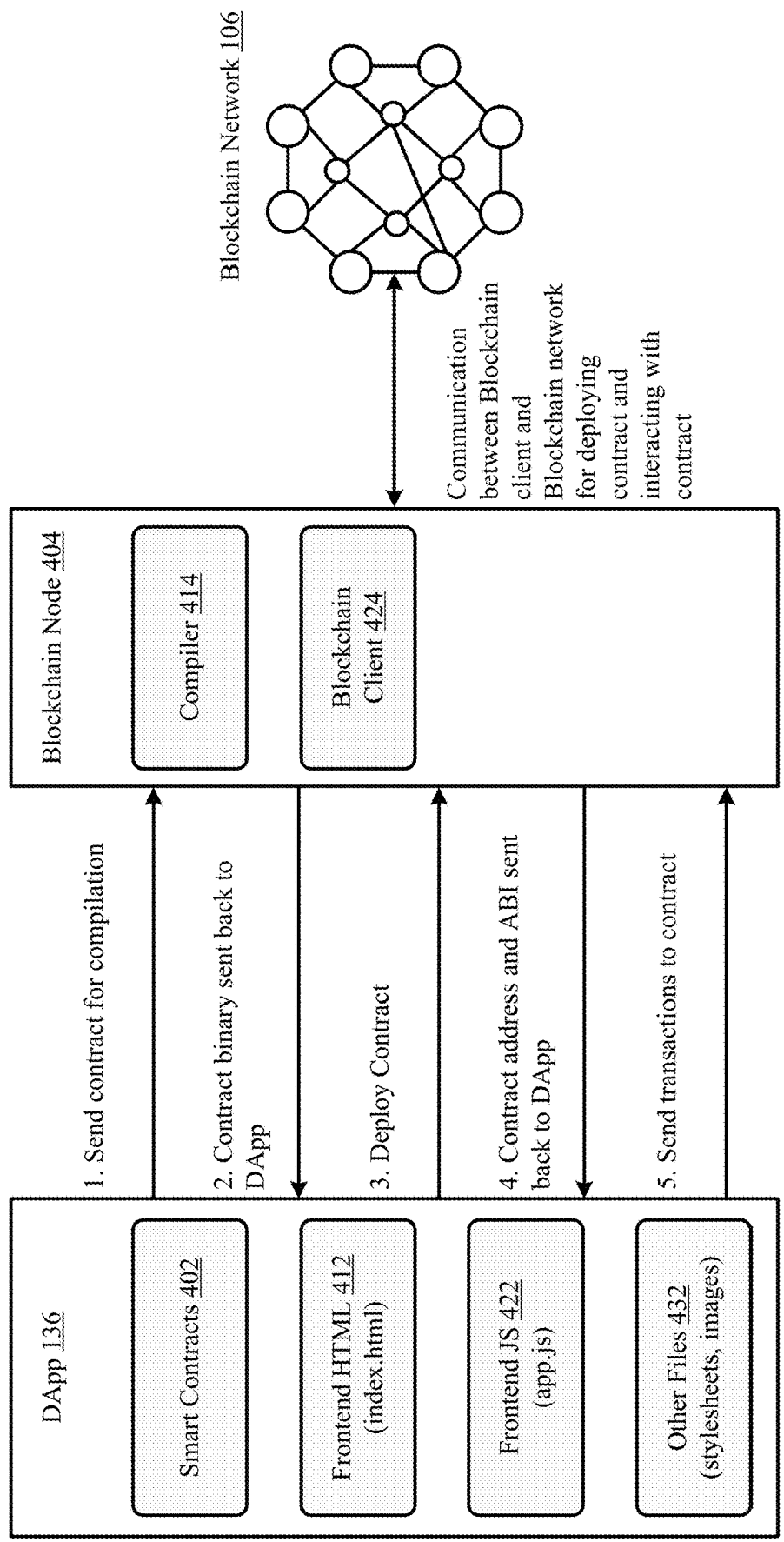
FIG. 4B is a flow diagram 400B depicting an example publicly accessible blockchain transactions that can be used to implement the technology disclosed.

FIG. 4A is a flow diagram 400A depicting an example permissioned blockchain transactions that can be used to implement the technology disclosed. In permissioned blockchain implementations, chain code can be installed onto peer server(s) 136 by interface server(s) 102 using a multiple-phase process.

In an install chain code process (flows 401-407) the source code is uploaded to the peer server(s) 136. There is no effect on the blockchain ledger here. This process is typically initiated via a peer administrator, an automaton identity which has admin privileges on the peer, including privileges to install chain code (i.e., upload source code of the chain code). In a flow 401, a request from the peer admin to install a chain code is received by an interface server(s) 102. Then, in a flow 403, the interface server(s) 102 makes a request to install chain code on the peer server(s) 136. The peer server(s) 136 perform the requested chain code install and reply in a flow 405 with a response indicating the operation was successful (or a failure). In a flow 407, the particular one of the interface server(s) 102 passes the response to the peer administrator that made the install request.

In an instantiate chain code process (flows 409-425) causes the chain code installed previously to be compiled and executed, typically placed in a ready state waiting for transaction requests. This takes the form of a formal transaction conducted upon the blockchain ledger; and it is subject to the same flow and rules. This process is typically initiated via a channel administrator, an automaton identity which has admin privileges on the channel (here, "channel" is another term for the blockchain), including privileges to instantiate chain code (instantiate or upgrade what chain code is running on the channel). In a flow 409, a request from the channel admin to instantiate a chain code is received by an interface server(s) 102. Then, in a flow 411, the interface server(s) 102 makes a chain code transaction proposal to instantiate chain code installed on the peer server(s) 136. The peer server(s) 136 perform instantiating the requested chain code and reply in a flow 413 with a response indicating the operation was successful (or a failure). The interface server(s) 102 makes a request to broadcast the instantiate chain code transaction in a flow 415, which is received by fabric orderer 155. The fabric orderer 155, which executes on a server other than the interface server(s) 102, orders the transaction and adds it to the blockchain ledger and replies in a flow 417 with a response indicating whether the operation was successful (or a failure). In a flow 419, if the broadcast failed, the particular one of the interface server(s) 102 passes the response to the channel administrator that made the install request. In a flow 421, the fabric orderer 155 sends a transaction commit result response to the peer server(s) 136. Peer server(s) 136 then send a transaction commit result response in flow 423 to the particular one of the interface server(s) 102 that initiated the instantiate chain code transaction in flow 411. The particular one of the interface server(s) 102 in flow 425 sends a response transaction commit result indicating the operation was successful (or a failure) to the channel administrator to indicate the outcome of the requested adding the transaction to the blockchain ledger.

In a blockchain access process, such as when a user at client device 122 wants to issue an electronic transaction that affects the blockchain ledger, the structure of this workflow is identical to that of the instantiate chain code process workflow described above with reference to flows 409-425 (since instantiate is just a particular kind of transaction).

FIG. 4B is a flow diagram 400B depicting an example publicly accessible blockchain transactions that can be used to implement the technology disclosed. DApp 136 is used to store the anomaly reports in the tamper-proof blockchain network 106. DApp 136 is decentralized in nature, with no single entity or organization controlling the infrastructure on which the applications are deployed. In the context of Ethereum™, DApp 136 is backed by smart contracts 402 which are deployed on the Ethereum™ blockchain platform that is maintained by the Ethereum™ nodes or peers worldwide. Even though DApp 136 is deployed on a central server which is either a full Ethereum™ node or a can communicate with an Ethereum™ node, the server only serves the DApp's web interface. The DApp logic is controlled by the associated smart contracts 402 which are deployed on the blockchain network 106. DApp 136 provides a friendly interface to smart contracts 402 where the client devices 122 can submit transactions to the contracts from a web interface based on frontend HTML 412, frontend JavaScript (JS) 422, and other files 432 like stylesheets and images. A DApp's web interface forwards the transactions to the blockchain platform and displays the transaction receipts or state information in the smart contracts 402 in the web interface. DApp 136 can use a decentralized messaging protocol such as Whisper™ for communication and decentralized storage platforms such as Swarm™ for static storage.

In example 400B, DApp 136 sends a smart contract to the blockchain node 404 for compilation. Blockchain node 404 comprises a compiler 414 and a blockchain client 424. Compiler 414 can compile smart contracts written in various high-level languages such as Solidity™, Serpent™, and Lisp™. Blockchain client 424 communicates with the blockchain network 106 and performs tasks such as creating accounts and contracts, sending transactions to contracts, and others. Examples of blockchain client devices 424 include geth (written in Go™) and pyethapp (written in Python™).

In response, the blockchain node 404 sends the contract binary to DApp 136. This allows DApp 136 to deploy the contract on the blockchain node 404. Once the contract is deployed, the blockchain node 404 sends a contract address and an application binary interface (ABI) to DApp 136. ABI provides an interface to the state variables and functions defined in the deployed contract. After this, DApp 136 sends transactions to the deployed contract.

Figure 5:
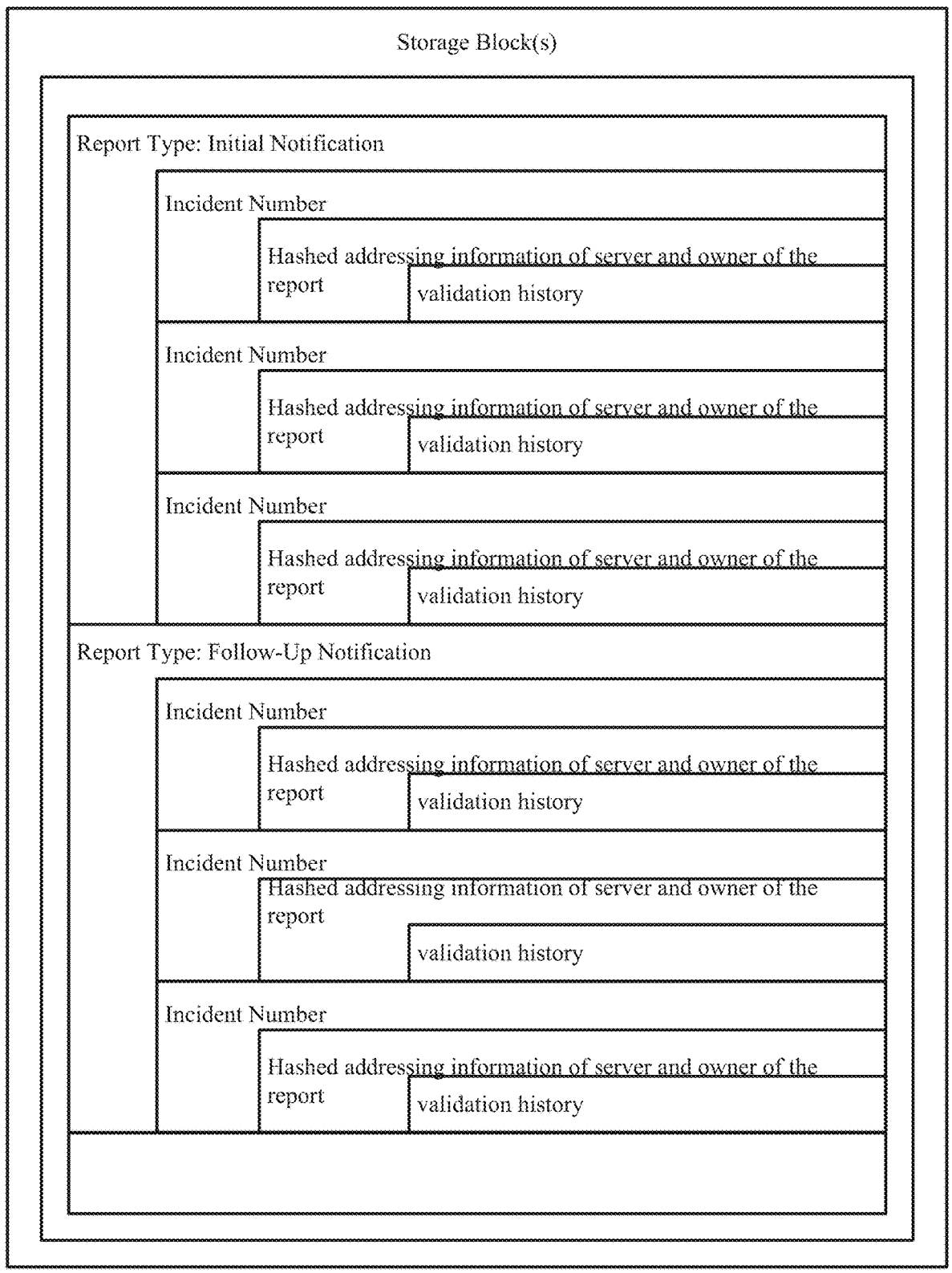
FIG. 5 illustrates an example storage block of a blockchain network that implements the technology disclosed.

FIG. 5 illustrates an example storage block 500 of a blockchain network 106 that implements the technology disclosed. Storage block(s) 500 identifies two related versions of an FDA 3911 report: version 1 is the initial notification and version 2 is the follow-up notification. For each version, the storage block(s) 500 identifies an incident number assigned to the anomaly. In implementations, data too sensitive to risk being stored directly on the blocks of the blockchain network 106 can be stored by Private storage server(s) 156 that access private collections data stored for each organization, which may comprise information of various drug databases (e.g., the FDA Product-Specific Guidance database, which enables searching and clustering by active ingredient(s)) and communications including machine reading of emails on recalls. Interface server(s) 102 is cooperatively coupled with, and permissively enabled to access the private collections stored by private storage server(s) 156 that can comprise multiple sources of data stored by individual organizations that are members of the blockchain network 106, thereby minimizing the need to change notification protocols that can be related to machine-readable data and image recognition (e.g. images of pills).

For example, medical privacy laws such as health insurance portability and accountability act (HIPAA), general data protection regulation (GDPR), and others, legal, regulatory or private, place restrictions on the usage and keeping of data. In such cases, information can be stored locally by participants in the blockchain network 106 in private storage server(s) 156. Addressing information can be pushed by the custodian of the locally stored data, typically in encrypted or other non-human readable form to provide protection from tampering by a single actor and provides for data confidentiality with encryption at the block level.

The storage block(s) 500 can also include hashed addressing information for private storage server(s) 156 that control copies of the potentially private information of other fields of the FDA 3911 form, such as a date of initial notification, name of the product, primary ingredients, etc. that are too sensitive to be included in bock(s) 500; thereby enabling the interface server(s) 102 to obtain this information when permitted and safeguarding this information from public release.

For example, data useful in regulatory compliance reporting stored by private storage server(s) 156 and pointed on by storage block(s) 500, can include without limitation: A type of report (e.g., initial notification, follow-up notification, or request for termination), an incident number (provided by FDA) for follow-up and request for termination, a date of initial notification to FDA (MM/DD/YYYY), a date company determined product was illegitimate (MM/DD/YYYY), a name of product as it appears on the label, primary ingredients, drug use (human, other), a drug description (e.g., finished prescription drug, vaccine, plasma derivative (e.g., coagulation factors, immunoglobulins, albumin), allergenic (e.g., standardized and non-standardized), or multiple), a strength of drug (e.g., 500 mg. 1 g/10 mL), a dosage form (e.g., tablet, capsule, aerosol, oral liquid, sublingual, injectable, topical, suppository, other, or multiple), a quantity of drug (Number and Unit), an NDC (Nat'l Drug Code) number, a serial number, lot number(s), expiration date(s), (for notification) a description of event/issue, (for request for termination of notification) description of why notification is no longer necessary, other reports submitted to the FDA (e.g., FAR—Field Alert Report, BPDR—Biological Product Deviation Report, Medwatch 3500, Medwatch 3500A, none, other), company name and address, company category, manufacturer, wholesale distributer, dispenser (Pharmacy), repackager, Unique Facility Number (D-U-N-S), and contact information.

Output(s) of classifier(s) once trained on a training dataset can also be stored by private storage server(s) 156 and pointed on by storage block(s) 500, can include without limitation: a classification of notification (e.g., counterfeit, diverted, stolen, intentional adulteration, unfit for distribution, fraudulent transaction, others) for a particular situation state.

Figure 6A:
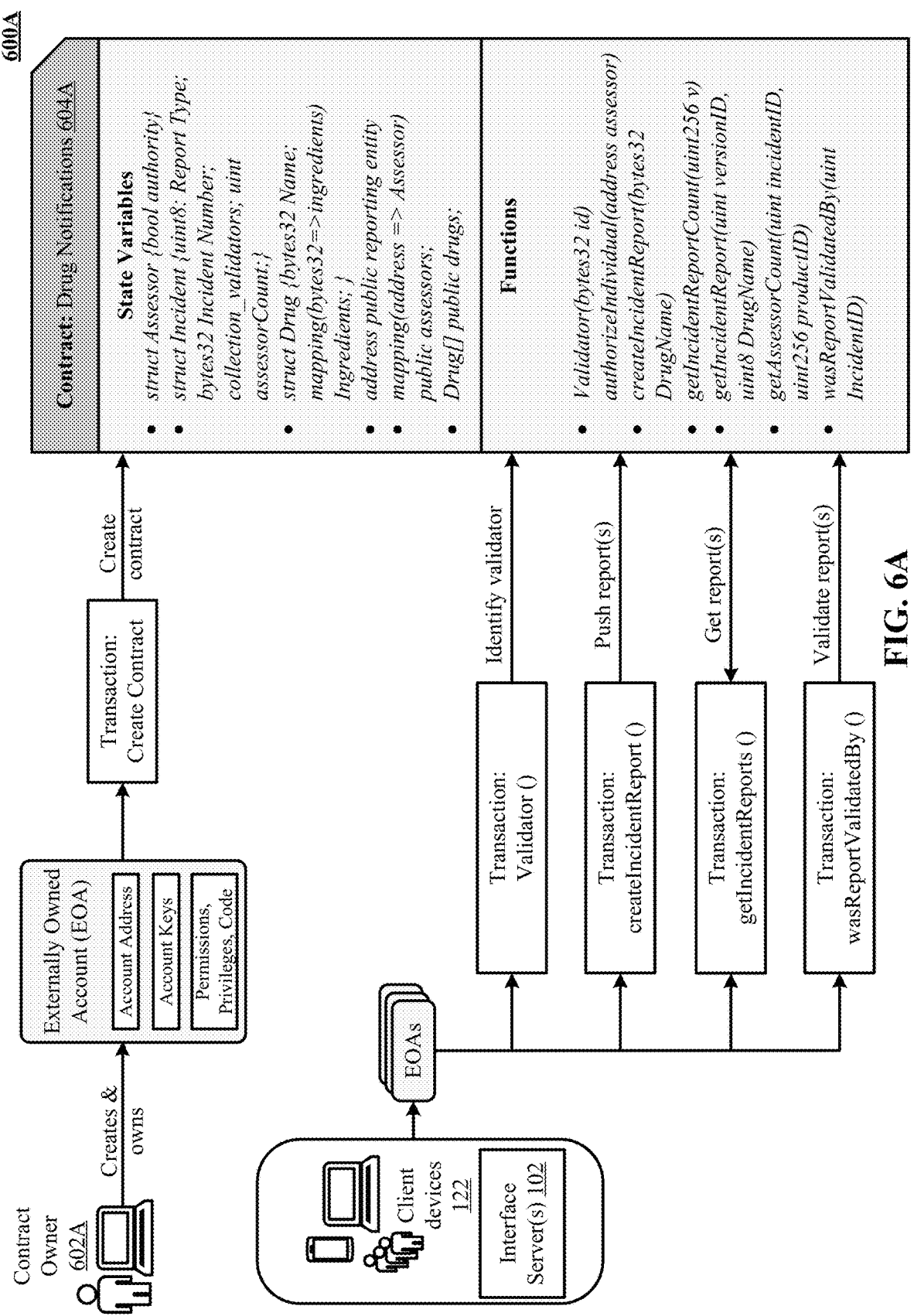
FIG. 6A illustrates an example workflow 600 in which a smart contract 604A implements the technology disclosed.

FIG. 6A illustrates an example workflow 600A in which a smart contract 604A implements the technology disclosed. Workflow 600A illustrates a contract owner 602A creates the smart contract 604A called "Drug Notifications" (e.g., "contract Validator") via an externally owned account (EOA). EOA has a public-private key pair associated with it. The account address (e.g., "address public chairperson") is derived from the public key. When a new EOA is created, a JSON key file is created which has the public and private keys associated with the account. The private key is encrypted with the password which is provided while creating the account. For sending transactions to other accounts, the private key and the account password are required. The contract account is controlled by the associated contract code which is stored with the account. The contract code execution is triggered by transactions sent by the EOA. In some implementations, smart contract 604A can be created by interface servers(s) 102.

Transactions are the electronic messages sent by EOAs to other EOAs or contract accounts. Each transaction includes the address of the recipient, transaction data payload, and a transaction value. When a transaction is sent to an EOA, the transaction value is transferred to the recipient. When a transaction is sent to a contract account, the transaction data payload is used to provide input to the contract function to be executed.

Smart contract 604A is used to store and validate the drug notification reports. Smart contract 604A includes state variables (e.g., "struct Incident", "struct Drug", "Drug[ ] public drugs") that can store and identify different versions of a reporting file. In addition, smart contract 604A also includes state variables (e.g., "struct Assessor", "struct Incident") that can store and identify data origin validation of given version by one or more validators.

Smart contract 604A also includes functions (e.g., "createIncidentReport") that can be used by client devices 122 and interface server(s) 102 to send the FDA forms 3911 to the smart contract 604A and in turn to the blockchain network 106. In implementations, a single function can be used to send FDA forms 3911 for the entire reporting file or separate functions can be used for individual reporting instances of the reporting file. Similarly, smart contract 604A includes functions (e.g., "getIncidentReports") that can be used by client devices 122 and interface server(s) 102 to get the FDA 3911 reports stored on the blockchain network 106. Smart contract 604A also includes functions (e.g., "wasReportValidatedBy") that allow client devices 122 and interface server(s) 102 to validate a report stored on the blockchain network 106. Smart contract 604A also includes functions (e.g., "Validator") that allow client devices 122 and interface server(s) 102 to identify themselves by sending their account addresses to the smart contract 604A.

Figure 6B:
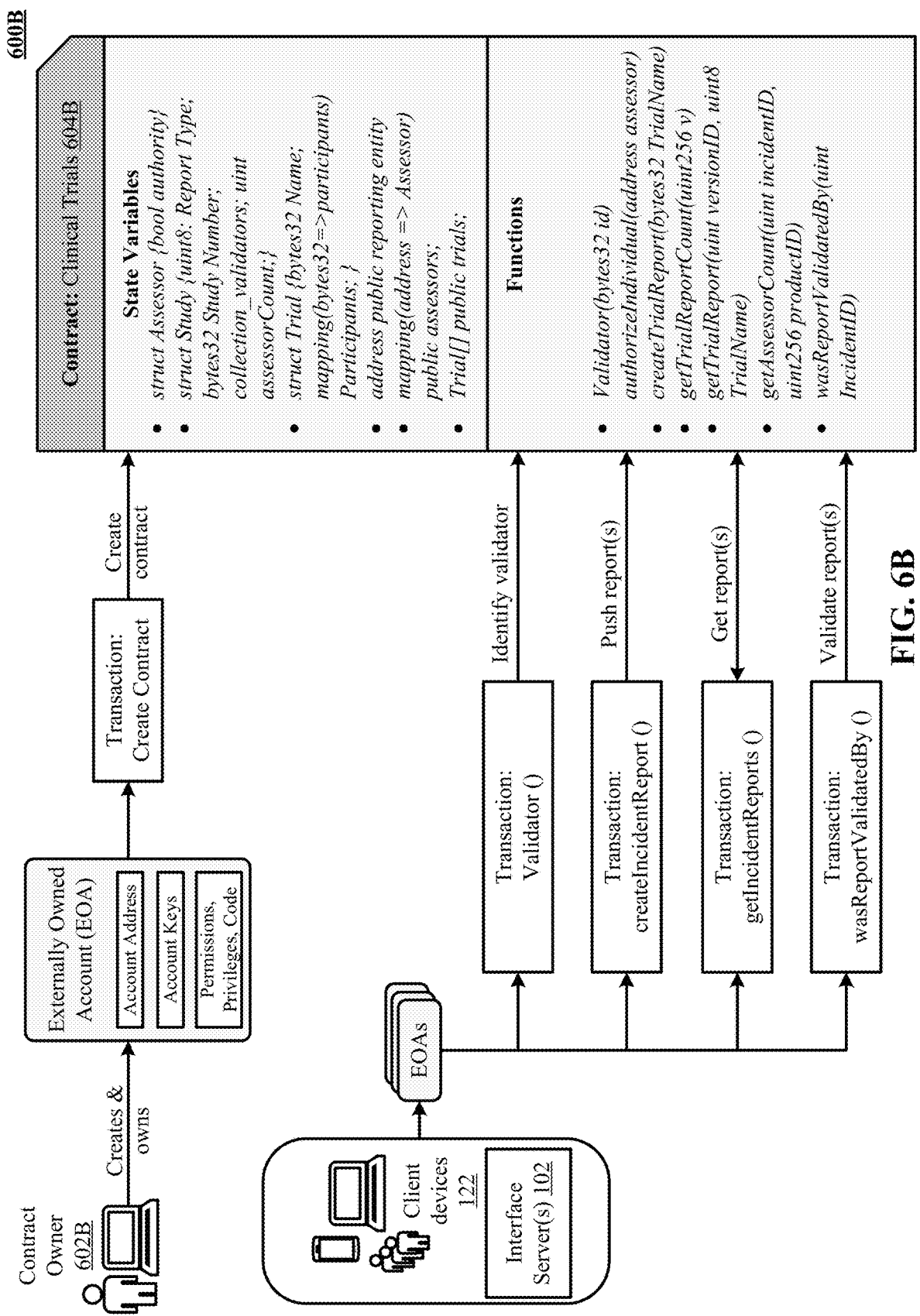
FIG. 6B illustrates an example workflow 600 in which a smart contract 604B implements the technology disclosed.

FIG. 6B illustrates another example workflow 600B in which a smart contract 604B implements the technology disclosed. Workflow 600B illustrates a contract owner 602B creates the smart contract 604B called "Clinical Trials" (e.g., "contract Validator") via an externally owned account (EOA). EOA has a public-private key pair associated with it. The account address (e.g., "address public chairperson") is derived from the public key. When a new EOA is created, a JSON key file is created which has the public and private keys associated with the account. The private key is encrypted with the password which is provided while creating the account. For sending transactions to other accounts, the private key and the account password are required. The contract account is controlled by the associated contract code which is stored with the account. The contract code execution is triggered by transactions sent by the EOA. In some implementations, smart contract 604B can be created by interface server(s) 102.

Transactions are the electronic messages sent by EOAs to other EOAs or contract accounts. Each transaction includes the address of the recipient, transaction data payload, and a transaction value. When a transaction is sent to an EOA, the transaction value is transferred to the recipient. When a transaction is sent to a contract account, the transaction data payload is used to provide input to the contract function to be executed.

Smart contract 604B is used to store and validate the clinical trial reports. Smart contract 604B includes state variables (e.g., "struct Study", "struct Trial", "Trial[ ] public trials") that can store and identify different versions of a reporting file. In addition, smart contract 604B also includes state variables (e.g., "struct Assessor", "struct Study") that can store and identify data origin validation of given version by one or more validators.

Smart contract 604B also includes functions (e.g., "createTrialReport") that can be used by client devices 122 and interface server(s) 102 to send clinical trial reports to the smart contract 604B and in turn to the blockchain network 106. In implementations, a single function can be used to send clinical trial reports for the entire study recording file or separate functions can be used for individual reporting instances of the study recording file. Similarly, smart contract 604B includes functions (e.g., "getTrialReports") that can be used by client devices 122 and interface server(s) 102 to get the clinical trial reports stored on the blockchain network 106. Smart contract 604A also includes functions (e.g., "wasReportValidatedBy") that allow client devices 122 and interface server(s) 102 to validate a report stored on the blockchain network 106. Smart contract 604A also includes functions (e.g., "Validator") that allow client devices 122 and interface server(s) 102 to identify themselves by sending their account addresses to the smart contract 604B.

As time-stamped immutable data structures, blockchains have found utility in cryptocurrency. Unlike a relational database, blockchain network 106 enables implementations to protect data from tampering by a single actor, and/or to provide data confidentiality with encryption at the block level. For additional information on the user of blockchains, reference may be had to U.S. application Ser. No. 15-345,031, entitled Extended Blockchains for Event Tracking and Management, filed Nov. 7, 2016, and U.S. application Ser. No. 15-454,492, entitled Extended Blockchains for Event Tracking and Management, filed Aug. 29, 2016, which applications are incorporated herein in their entirety by reference for all purposes.

Having described smart contract-based implementation of the technology disclosed, the discussion now turns to the interface server(s).

Interface Servers

In one implementation, the interface server(s) 102 are provisioned as clients to the blockchain system 106, provisioned as production server(s) 304, enabling their function to be safe from prying eyes. The challenge for permissioned blockchains within regulated communities is to create a robust community that meets regulatory obligations in near-real-time without simultaneously creating a single point of failure or back-door. Once a single point of failure is created, the blockchain for all intents and purposes becomes a centralized database, whether the architecture is decentralized. Implementation specifics differ; depending on the nature of a particular installation's user and regulatory requirements, the interface server(s) 102 can be configured in different configurations, outlined below.

In an implementation, configurations are based on the relationships between users (e.g. omniscient regulator, board of governors, or root of trust) and the degree of access required for the interface server(s) 102 to be effective (omniscient agent, constrained community-wide agent, or constrained and transparent task-specific agent). The interface server(s) 102 are restricted to only log into the block chain system as a user. Privacy can be enhanced by restricting the interface server(s) database access on the level of a traditional database administrator. As an automaton user, the interface server(s) require no human-readable interface (UX/UI); rather can create notifications to relevant client devices 122 and conducts block-level transactions with blockchain network 106.

In one alternative example, if an interface server implementation only requires publicly accessible data to perform a function (as in the case of Form 3911 outlined below), the core of the interface server(s) logic can be implemented as smart contracts within the blockchain system 106. Such smart contracts, by definition, are auditable by every community member, and provide fine-grained control over what data is ultimately shared with what parties. This control can be ensured through leveraging a combination of data privacy features unique to permissioned blockchains. For instance, building on Hyperledger Fabric, the interface server logic would be implemented as separate chain code, responsible for flagging anomalous transactions or alerting on suspicious correlations. It would be straightforward for an interested party to verify that this chain code cannot be used by any party to query data at-will, and that the notifications are output only to relevant community members. Further control can be exercised by deploying the chain code on separate channels, which allows restricting information sharing between subsets of system participants.

In another alternative example, if an interface server implementation additionally procures private data that does not exist on the blockchain (e.g. from a particular organizations' private storage server(s) 156, then the private source being accessed by the interface server(s) 102 would need to be trusted by all other participants on the blockchain. Though interface server(s) 102 wouldn't necessarily have access to all of an organization's private data, it would be granted access to the requisite set of data needed to function. This could take the form of viewing private collection files to which a given organization granted it access (given rules such as "send interface server all user-submitted images of suspected faulty pill bottles"), or by having more global access to private collections.

As mentioned previously, the first approach would be suitable in the case of the FDA DSCSA. Form FDA 3911 submissions are used by the system users to generate exception reports for suspicious drugs. Each of the fields from the 3911 could be held on the blockchain as a separate variable. Interface server(s) flag any identical entries in any fields (e.g. two matches may be adequate for a notification involving a controlled substance, perhaps three for a less dangerous medicine) for further escalation in a smart manner. For example, if a Walgreens dispenser in Chicago says that Oxycontin lot #5667777 looks wrong and CVS in Woonsocket reports a problem with the same lot, the escalation by the interface server(s) 102 might trigger them sending a fresh notification to the manufacturer and FDA, indicating that this lot has multiple reporters reporting a problem. Under the current Form 3911 system, the manufacturer and FDA would receive two different notifications from two different reporters and have to collate them manually offline.

In an implementation, the interface server(s) 102 accesses smart contracts that can invoke follow-up notifications to the reporting entity or entities. The submitting or reporting entity might be asked to take a picture of the goods in question, or confirm their whereabouts, or ask to describe symptoms. They might also be asked to quarantine suspicious materials, or mail them to the CDC, or hold for pickup by the DEA.

With a notification from participating interface server(s), the FDA can then post a Medwatch notification or call the manufacturer and ask for clarification. Alternatively, a manufacturer might proactively ask for quarantine. For especially sensitive products such as fentanyl, the system could quarantine all transactions for that lot for 24 hours while humans at the manufacturer and FDA discuss their options.

This implementation is part of a broader initiative to develop a system of blockchain-validated reporting, resolution and root cause analysis. The implementations illustrated by FIGS. 7A, 7B implement tracking and responding in near-real-time to out-of-spec asset reports in critically important supply scenarios and managing access to clinical trial information, respectively.

Having described smart contract-based implementation of the technology disclosed, the discussion now turns to some example use cases.

Example Use Case

Figure 7A:
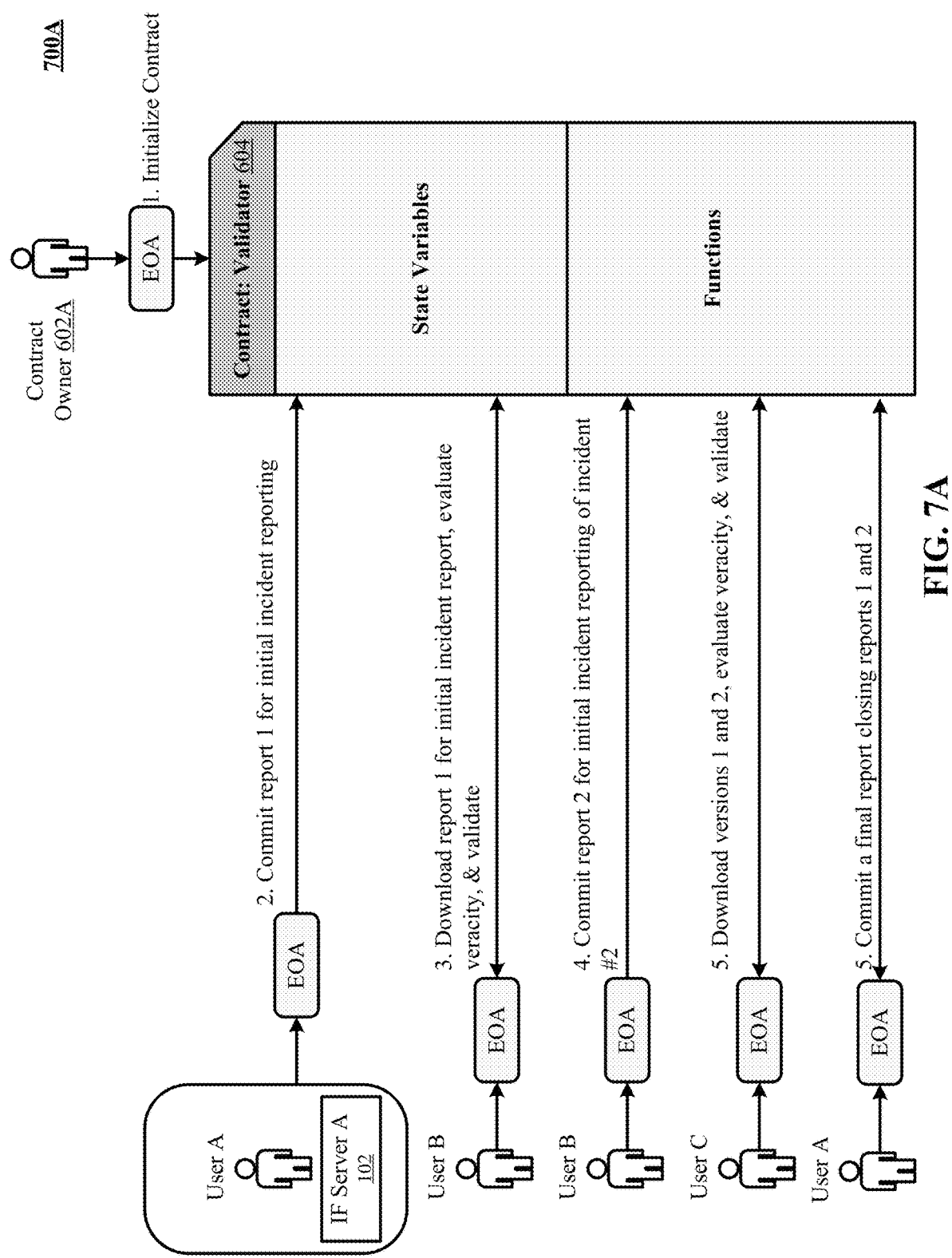
FIGS. 7A, 7B depict example use cases 700A, 700B.

FIG. 7A depicts an example use case 700A in which the smart contract 604A of FIG. 6A is used to securely authenticate an incident reporting file from initial collection through resolution. The technology disclosed provides a way to securely authenticate an incident reporting file from initial collection through post-resolution. Consider that a first actor affiliated with a regulatory enforcement agency for example, uses a client device 122 to create a smart contract 604A on the blockchain network 106 with a policy goal of ensuring data integrity and creating a provenance trail of evidentiary data collection of an incident event. If a seal is broken on a pill bottle, for example, a dispenser (pharmacy) is required to categorize and report the problem via an FDA form 3911 within 24 hours. The initial incident report can be prepared and submitted by one of client devices 122, authorized to submit such reports on behalf of the dispenser (or warehouse encountering a damaged shipment, etc.) using their device to invoke the interface server 102. In the case of the FDA DSCSA, FDA form 3911 submissions are used by the system users to generate exception reports for suspicious drugs. Each of the fields from the 3911 can be held on the blockchain as a separate variable. Interface server 102 flags any identical entries in any fields (e.g. two matches may be adequate for a notification involving a controlled substance, perhaps three for a less dangerous medicine) for further escalation.

To persist and authenticate the origin of the report, a first custodian (e.g., user A) using the guided screens driven by deep neural network(s) 1334 can collect and input information into the application required to prepare FDA form 3911 and upload the report to smart contract 604A. These inputs can be stored on the blockchain network 106 as a report of the incident along with the credentials of user A.

Accordingly, when another user B, such as a pharmacy in a neighboring county, receives a local copy of the report from the regulatory enforcement agency, to ensure that the original information has not been tampered with, user B can generate for the local copy of the report and compare it with those stored on the blockchain network 106 as report 1. This may require the regulatory enforcement agency giving user B access to smart contract, in addition to the report (which can be provided separately). For example, if a Walgreens dispenser in Chicago reports that Oxycontin lot #5667777 looks wrong, a CVS in Woonsocket (user B) compares their local copy and the blockchain version. User B can determine the veracity of the local copy. If local copy is unaltered, user B can validate report 1 and store the validation on the blockchain network 106 appended to report 1 so that other users can see that report 1 has been validated by another user.

It is often the case that exceptions affecting one shipment will also affect other shipments in the lot. User B examines their stock for similar discrepancies. User B upon investigation discovers a problem with the same lot, user B can generate a report for any exceptions that they find in their stock and commit the report to the blockchain network 106 as a second report. Detecting identical problems causes interface server 102 of user B to escalate the problem, triggering a notification to the manufacturer and FDA, indicating that this lot has multiple reporters reporting a problem.

This may motivate another user C, such as a manufacturer, to compare the report 1 and report 2, verify the chain of custody all the way back to the point of origin, and validate that report 2 is related to the same problem as report 1. In implementations, prior versions of a current version can be stored. This way, a provenance trail of the chain of custody can be stored and presented using smart contract 604A.

One implementation includes a mobile application that executes as a client on one or more client device(s) 122, displaying panels as triggered by the interface server(s) 102 when backed by a blockchain network 106, captures barcodes on questionable package and video, audio or other sensed information. A representative usage scenario of a mobile application is next described with reference to FIGS. 8A-8H.

Figure 8A:
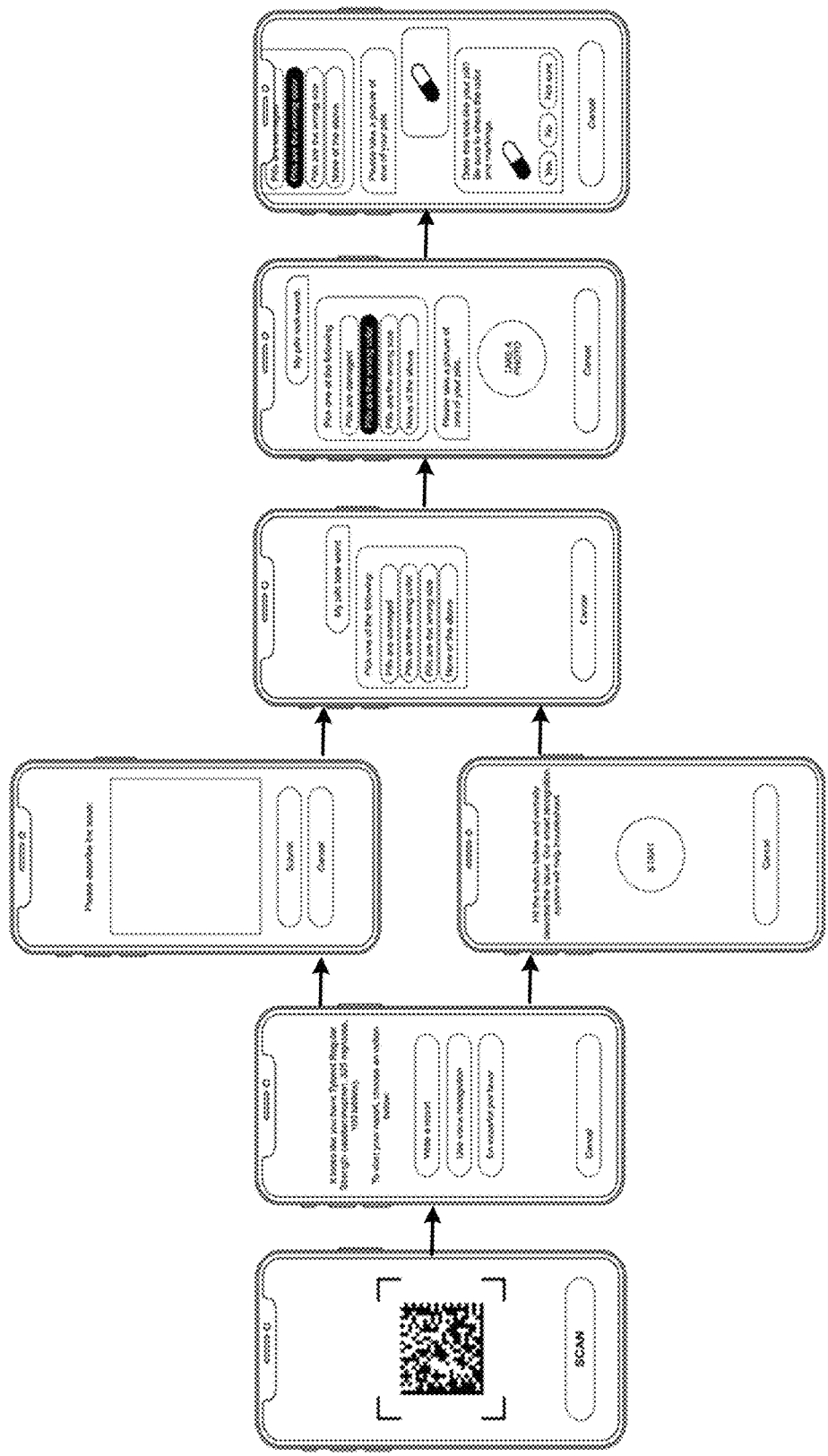
Figure 8B:
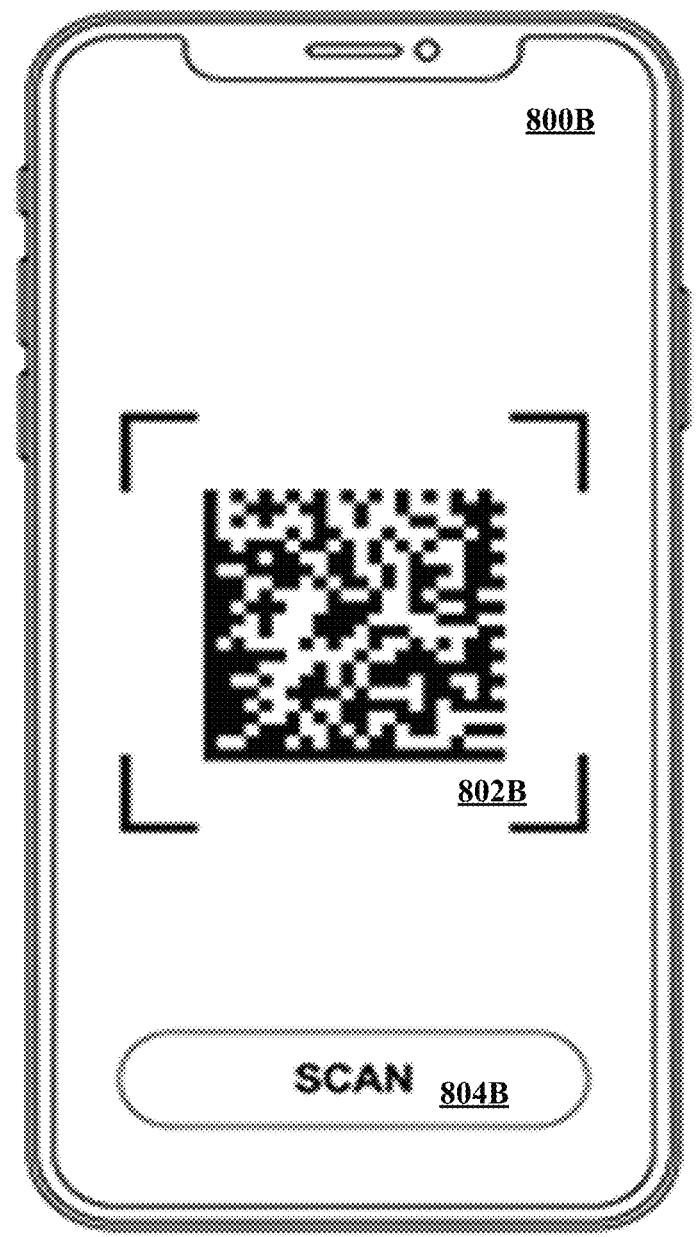

FIGS. 8A-8H depict an example use case 800. In FIG. 8A, an example 800A depicts a series of prompts displayed to a user in a representative usage scenario. In FIG. 8B, an example screen 800B is shown. Screen 800B displays a QR code 802B that the client device 122 has displayed along with a scan prompt 804B, enabling the user to capture the QR code by depressing the prompt 804B. Client device 122 captures the QR Code and sends the QR code to the interface server(s) 102 via network(s) 101. The interface server(s) 102 will retrieve information from private storage server(s) 156 and sends this information to the client device 122 via the network(s) 101.

Figure 8C:
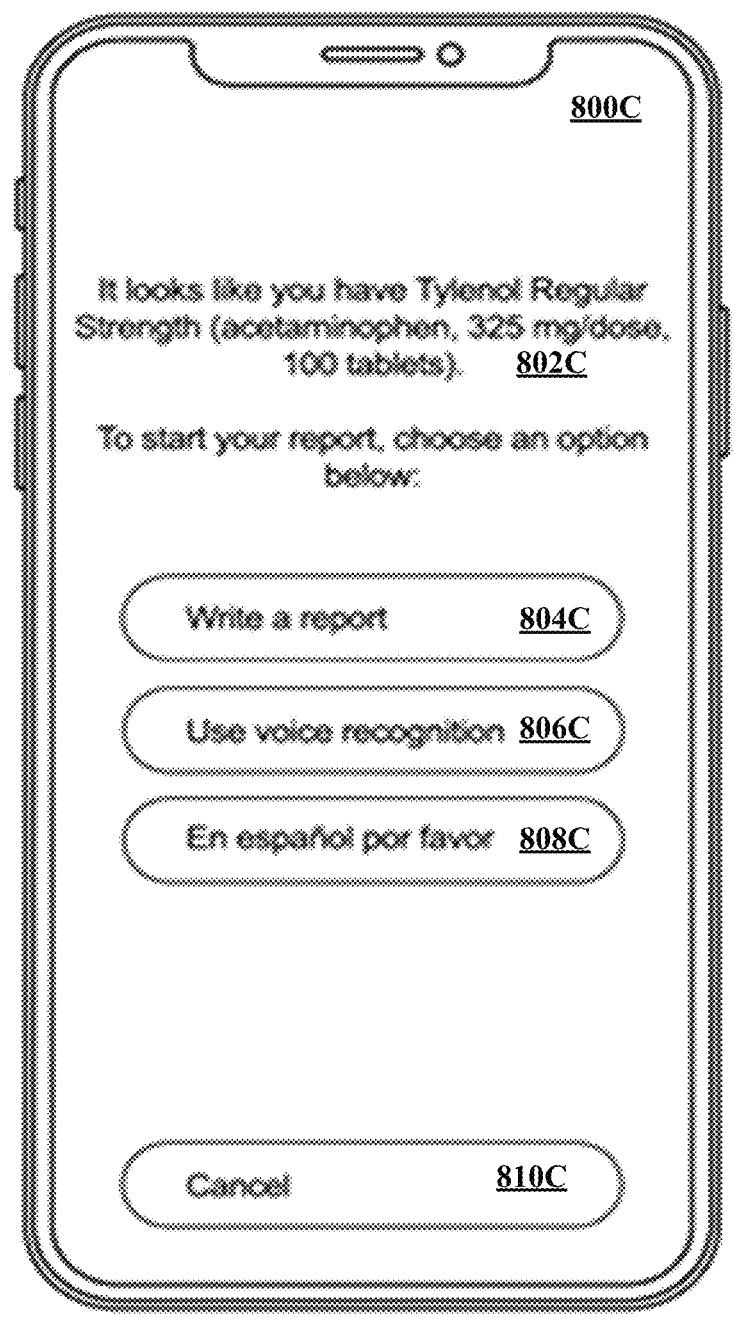

In FIG. 8C, screen 800C displays the information 802C sent to client devices 122. Screen 800C also displays a plurality of prompts to solicit from the user an input triggering a course of action, including a write report prompt 804C, a use voice recognition prompt 806C, a prompt 808C to change user languages and a cancel prompt 810C. Not all prompts will be displayed in every implementation. Further, some implementations will include other additional prompts facilitating different actions.

Figure 8D:
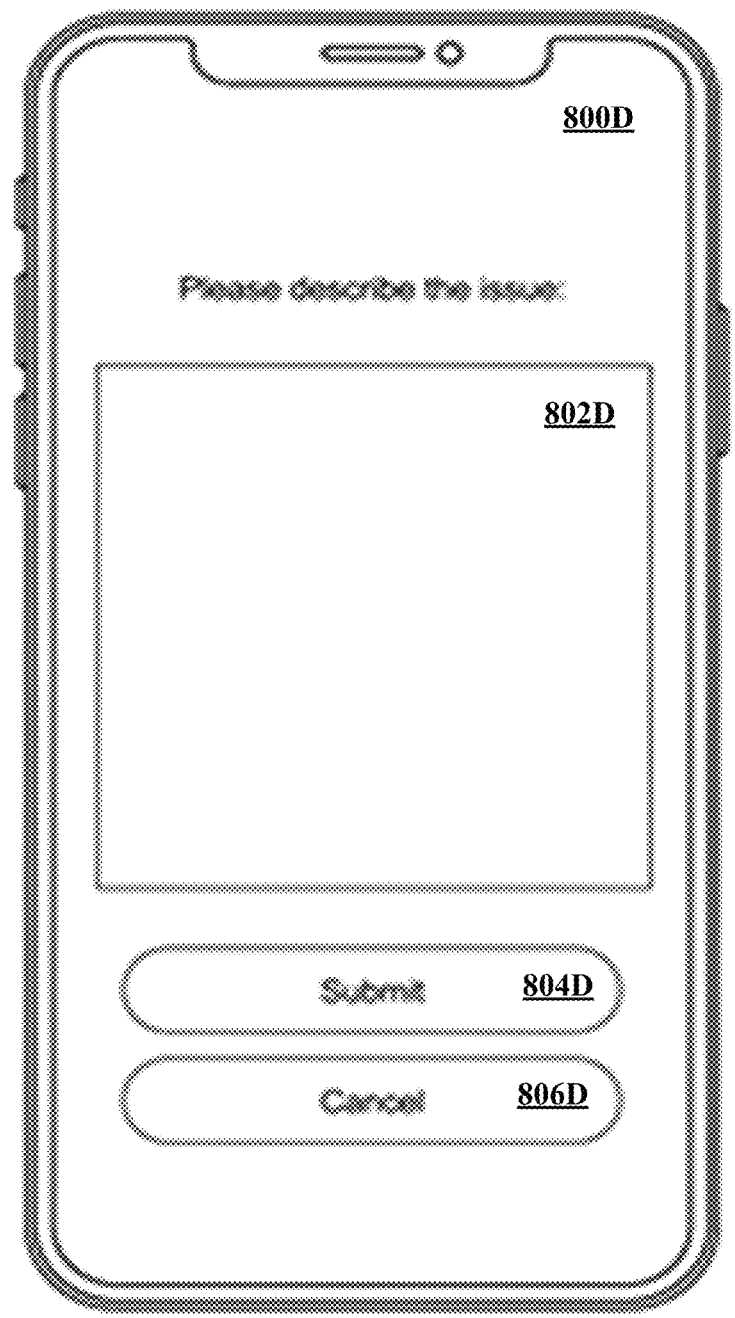
Figure 8E:
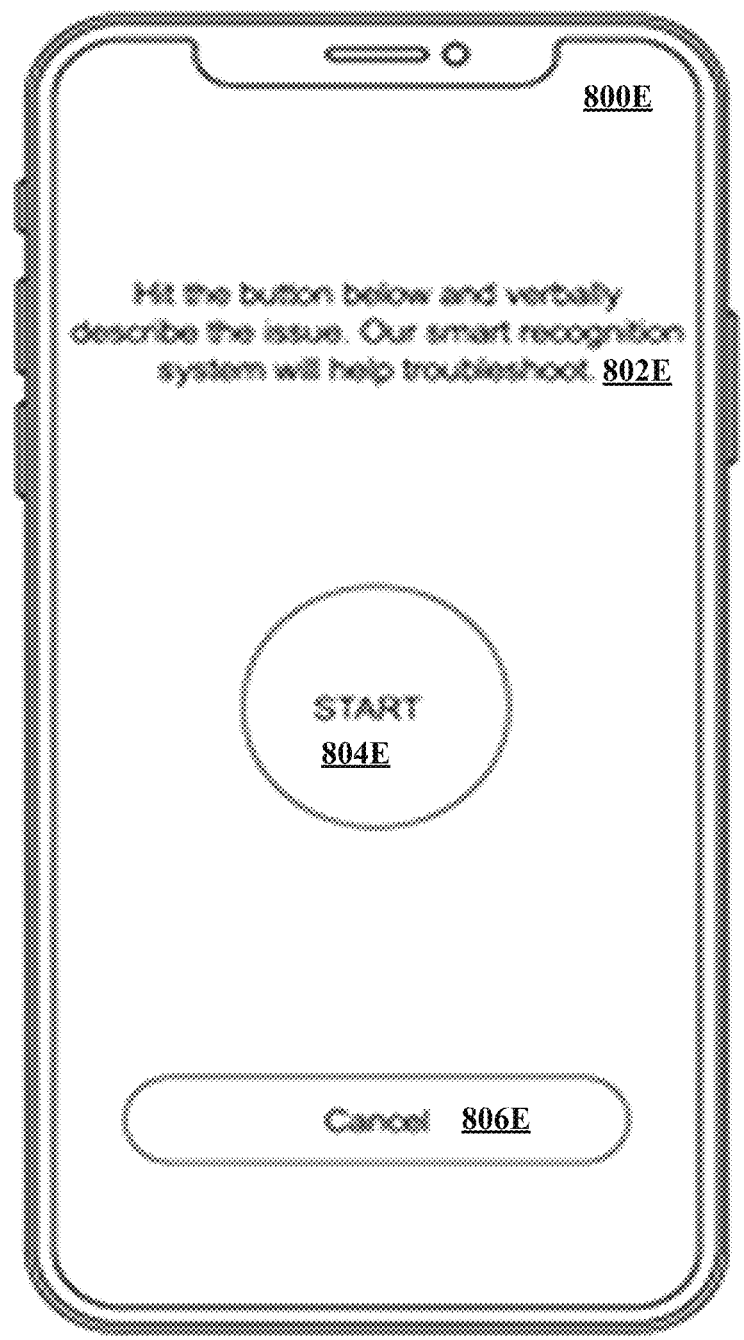

Now with reference to FIG. 8D, screen 800D is displayed by client device 122. Interface server(s) 102 has triggered client device 122 to display an input area 802D prompting the user to enter a description of an issue or problem. Screen 800D further includes a submit prompt 804D and a cancel prompt 806D. When a user enters their problem description into the input area 802D and selects the submit prompt 804D, client device 122 sends the information to the interface server(s) 102. The interface server(s) 102 analyzes the input text into vector representations and inputs these into one or more of the learning models (s) 134. Learning model(s) 134, such as a deep neural network(s) 1334 provide an output result based upon statistically learned results. The interface server(s) 102 using the result triggers an application to implement a course of action selected by the learning model(s) 134 as having a greater than threshold probability to remediate the problem encountered. The course of action can include one or more of prompting the client device 122 for additional details, or inputs such as capturing a photograph, voice input, etc., directions to the user such as how to dispose of or return a bad lot, and/or formulate a report to a regulatory agency. One example of one type of follow up prompting triggered by interface server(s) 102 is illustrated by FIG. 8E, depicting a screen 800E including a voice input prompt 802E that prompts the user to press a prompt 804E and describe the issue. A cancel prompt 806E is also provided.

Figure 8F:
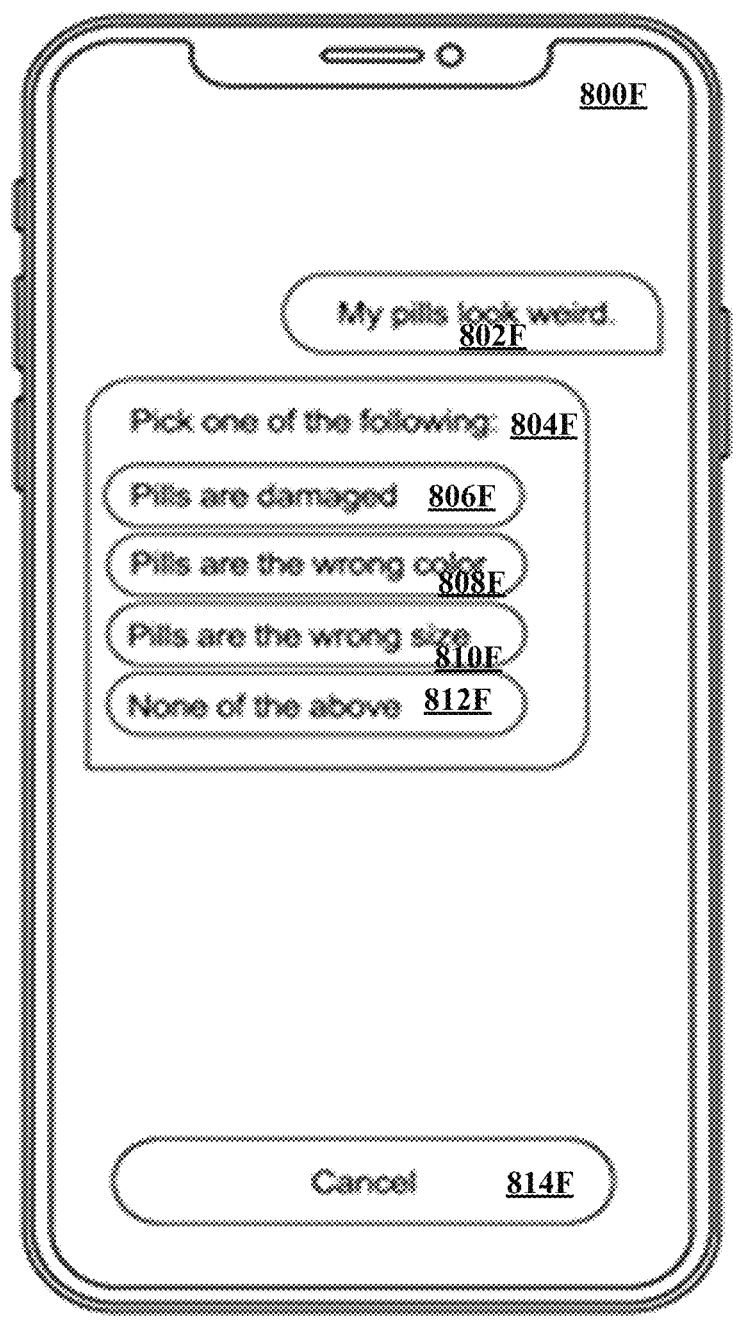

FIG. 8F depicts screen 800F illustrating an example of another type of follow-up prompting triggered based upon output of learning model(s) 134. In the scenario illustrated by FIG. 8F, the user has entered a nebulous input "my pills look weird" in input box 802F. Client device 122 passed this nebulous input to the interface server(s) 102, which analyzed the nebulous input and submitted it as input to one or more of the learning model(s) 134. Learning model(s) 134, such as a deep neural network(s) 1334 provide an output result based upon statistically learned results provided as output a set 804F of follow-up prompts. Follow up prompt 804F prompts the user to "pick one of the following" from a set of potential inputs. The set of potential inputs selected by the learning model(s) 134 as having a greater than threshold probability to remediate the problem encountered include "pills are damaged" 806F, "pills are the wrong color" 808F, "pills are the wrong size" 810F and "none of the above" 812F. Also displayed is an option for the user to cancel 814F.

Figure 8G:
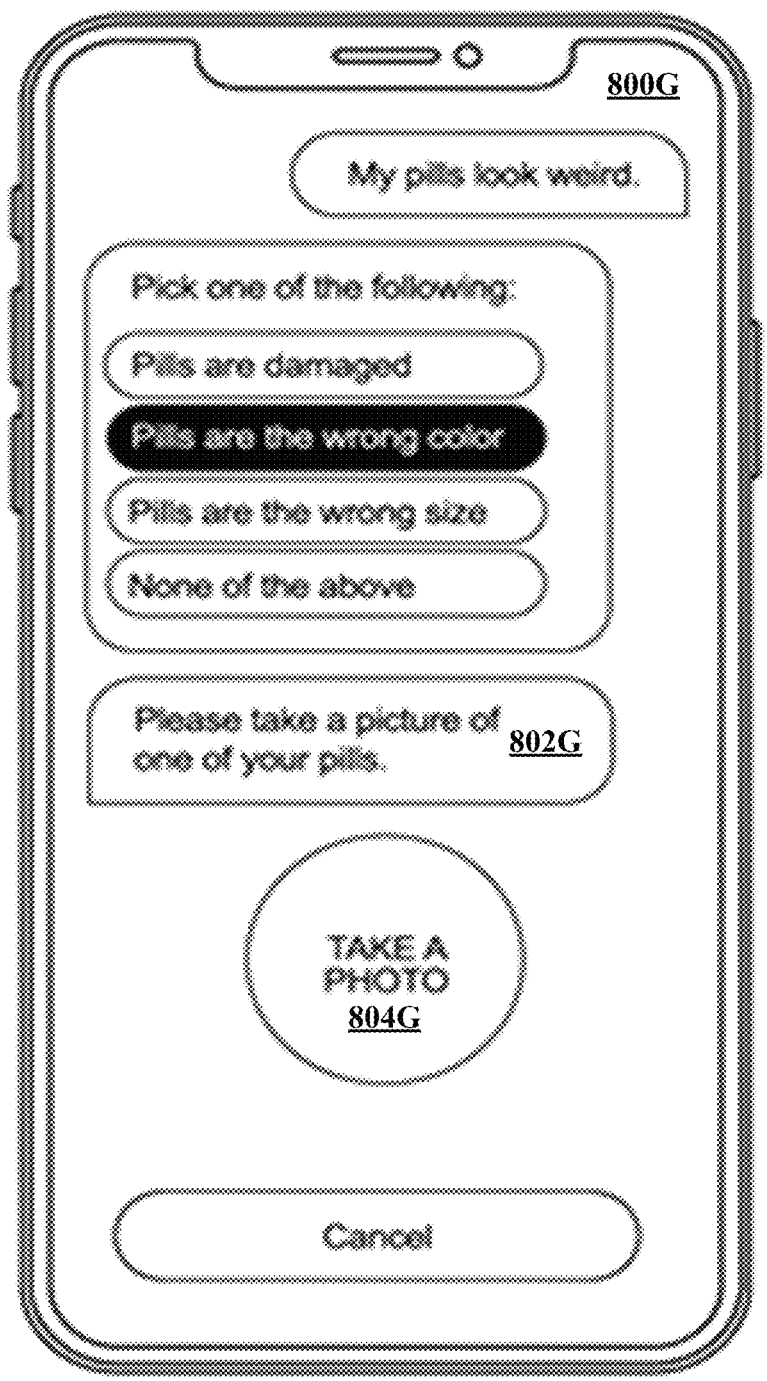
Figure 8H:
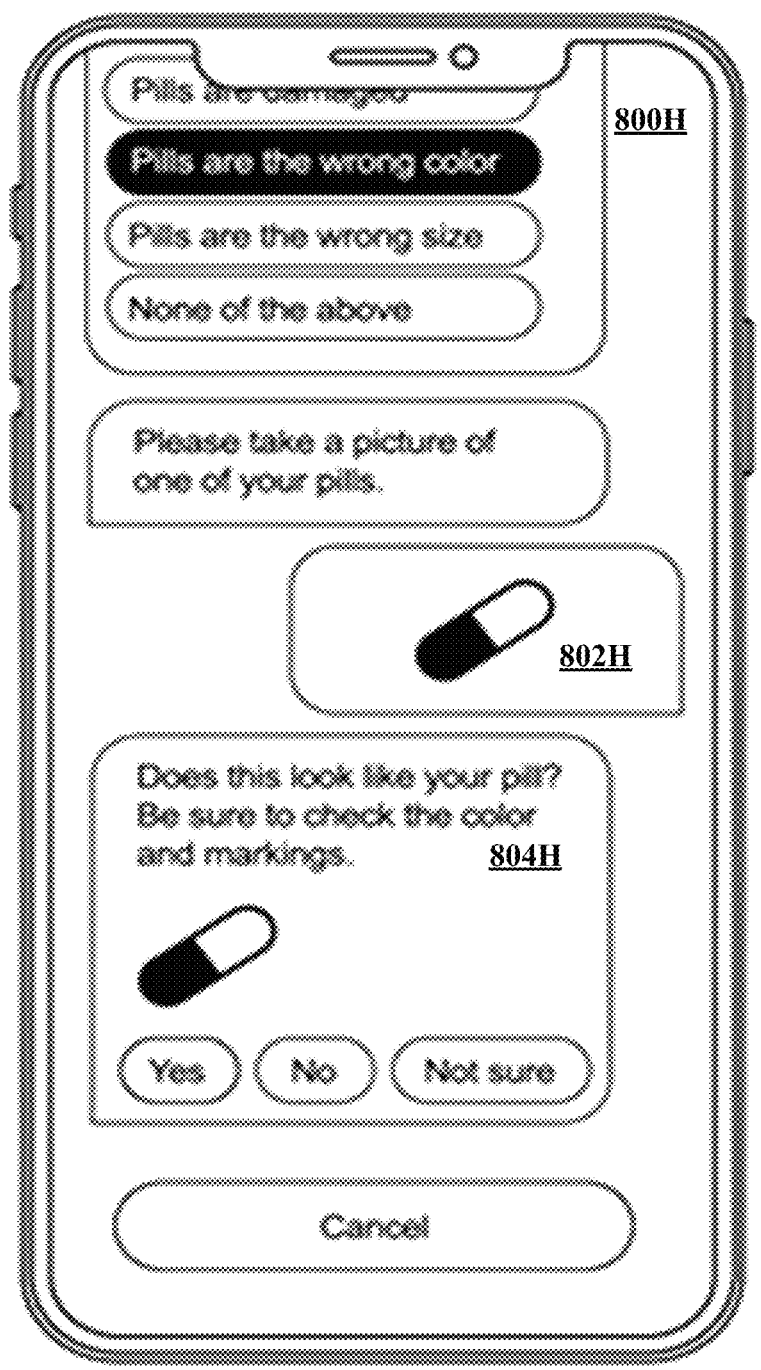

Now with reference to FIG. 8G, continuing with the scenario described with reference to FIG. 8F, the user has selected option "pills are the wrong color" 808F. The interface server(s) 102 respond with a further follow-up prompt 802G that urges the user to use the camera of client device 122 to take a picture of one of your pills and provides a camera trigger prompt 804G. Alternatively, or in addition, follow up screen 800H of FIG. 8H can be triggered. Screen 800H includes a picture 802H of the product corresponding to the QR code input in screen 800B, which the interface server(s) 102 have retrieved from private storage server(s) 156. Screen 800H further includes a follow up prompt 804H that asks the user specifically about the picture 802H and the product that the user of client device 122 is working with. The user's response will be sent to the interface server(s) 102 and again submitted to the learning model(s) 134 to trigger a remedial action if appropriate.

FIGS. 8I1 and 8I2 illustrate a system console screen 800I in an implementation. Screen 800I depicts a plurality of chain code known to the blockchain network 106. Processes executing with administrative privileges can install and/or instantiate these chain codes in various peer server(s) 136 using the process flows described herein above with reference to FIG. 4A.

Figure 7B:
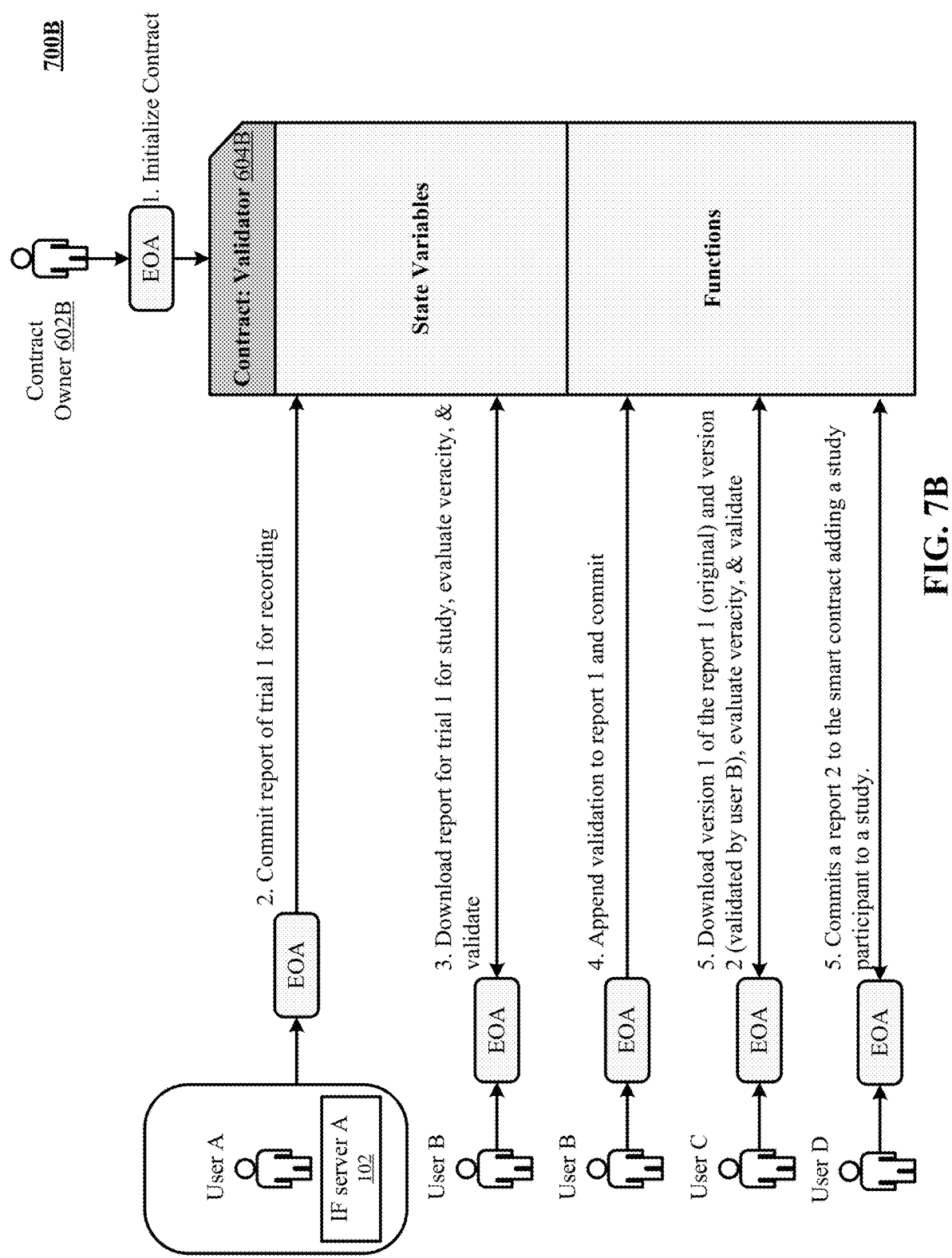

FIG. 7B depicts an example use case 700B in which the smart contract 604B of FIG. 6B is used to securely authenticate a clinical study recording file from initiating the study to collection of trial data throughout the study to completion. The technology disclosed provides a way to securely authenticate a clinical study recording file from initiation through post-completion. Consider that a first actor, contract owner 602B uses a client device 122 to create smart contract 604B on the blockchain network 106. The first actor can be affiliated with a clinical lab, hospital, research institution, or governmental or non-governmental agency with a policy goal of ensuring data integrity and creating a provenance trail of evidentiary data collection of trials conducted in furtherance of the clinical study. Subsequently, an initial trial report can be prepared and submitted using one of client devices 122, that has been authorized to submit such reports on behalf of the clinic (or research lab, hospital, etc.) using their device to invoke an instance of interface server 102. Trial report submissions are used by the system users A, B, C, etc. to generate records for trials being conducted in furtherance of the study. Each of the fields from the study record can be held on the blockchain as a separate variable. Interface server(s) 102 flags any identical entries in any fields (e.g. two matches may be adequate for trial IDs in recordings of trials, perhaps three for variables in which some duplicity is expected).

To persist and authenticate the origin of the record, a first custodian (e.g., user A) using the guided screens driven by learning model(s) 134 can collect and input information into the application required to prepare and upload the record of a particular trial to smart contract 604B corresponding to a particular study. These inputs can be stored on the blockchain network 106 as a report of the trial along with the credentials of user A.

When another user B, such as a scientist conducting a clinical trial, receives a local copy of the report from user A of trial 1, to ensure that the original information has not been tampered with, user B can generate an encrypted version for the local copy of the report and compare it with those stored on the blockchain network 106 as report of trial 1. An interface server(s) 102 invokes contract validator 604B to determine whether user B has been granted permission to view the report 1 including patient related data portions. Permission may have been given by the research lab, governmental agency or non-governmental agency that acts as contract owner 602B of the study. This can require the contract owner 602B giving user B access to smart contract 604B, in addition to the report (which can be provided separately). For example, if report 1 includes patient related data, the interface server(s) 102 compares the role of user B with the access permissions required to view the report 1, by determining whether the request is made by a participant in a clinical trial or a scientist conducting a clinical trial. Interface server(s) 102 then permits access to the participant of a subset of the clinical trial information suitable for the participant, otherwise permitting access to the scientist of a different subset of the clinical trial information suitable for the scientist. User B, being a scientist in this case, encrypts their local copy and compares it to the blockchain version, enabling user B can determine the veracity of the local copy. If local copy is unaltered, user B can validate report 1 and store the validation on the blockchain network 106 appended to report 1 so that other users can see that report 1 has been validated by another user. On the other hand, if user B were a study participant, rather than a scientist, interface server(s) 102 would permit user B access only to portions of the block-level data in the report 1 suitable to a participant in the trial.

Another user C, such as a scientist in a different facility that is also conducting trials, might download report 1 and compare the original version of report 1 with the version of report 1 with validation appended to it by user B, verifying the chain of custody all the way back to the point of origin, and validating that report 1 version 2 is related to the same trial as report 1, original version. In implementations, prior versions of a current version can be stored. This way, a provenance trail of the chain of custody can be stored and presented using smart contract 604B.

Another scientist, user D, requests to add a patient to a trial in the study using their client device 122 locates a block on the chain in which some patient data of the request relates. The interface server(s) 102 using smart contract 604B determines whether the request is authorized under a smart contract governing the use of the clinical trial blockchain; and adds the patient to the clinical trial whenever the request is authorized.

Computer System

FIG. 9 illustrates one implementation of a computer system 900 that can be used to implement the technology disclosed. Computer system 900 includes at least one central processing unit (CPU) 972 that communicates with a number of peripheral devices via bus subsystem 955. These peripheral devices can include a storage subsystem 910 including, for example, memory devices and a file storage subsystem 936, user interface input devices 938, user interface output devices 976, and a network interface subsystem 974. The input and output devices allow user interaction with computer system 900. Network interface subsystem 974 provides an interface to outside networks, including an interface to corresponding interface devices in other computer systems. The analyzer and deep learning system can be communicably linked to the storage subsystem 910 and the user interface input devices 938.

User interface input devices 938 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 900.

User interface output devices 976 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 900 to the user or to another machine or computer system.

Storage subsystem 910 stores programming and data constructs that provide the functionality of some or all of the modules and methods described herein. These software modules are generally executed by deep learning processors 978.

Deep learning processors 978 can be graphics processing units (GPUs) or field-programmable gate arrays (FPGAs). Deep learning processors 978 can be hosted by a deep learning cloud platform such as Google Cloud Platform™, Xilinx™, and Cirrascale™. Examples of deep learning processors 978 include Google's Tensor Processing Unit (TPU)™, rackmount solutions like GX4 RACKMOUNT Series™, GX2 Rackmount Series™, NVIDIA DGX-1™ Microsoft' Stratix V FPGA™, Graphcore's Intelligent Processor Unit (IPU)™, Qualcomm's Zeroth Platform™ with Snapdragon Processors™, NVIDIA's Volta™, NVIDIA's DRIVE PX™ NVIDIA's JET SON TX1/TX2 MODULE™, Intel's Nirvana™, Movidius VPU™, Fujitsu DPI™, ARM's DynamicIQ™, IBM TrueNorth™, and others.

Memory subsystem 922 used in the storage subsystem 910 can include a number of memories including a main random access memory (RAM) 932 for storage of instructions and data during program execution and a read only memory (ROM) 934 in which fixed instructions are stored. A file storage subsystem 936 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 936 in the storage subsystem 910, or in other machines accessible by the processor.

Bus subsystem 955 provides a mechanism for letting the various components and subsystems of computer system 900 communicate with each other as intended. Although bus subsystem 955 is shown schematically as a single bus, alternative implementations of the bus subsystem can use multiple busses.

Computer system 900 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 900 depicted in FIG. 9 is intended only as a specific example for purposes of illustrating the preferred embodiments of the present invention. Many other configurations of computer system 900 are possible having more or less components than the computer system depicted in FIG. 9.

Convolutional Neural Networks

A convolutional neural network is a special type of neural network. The fundamental difference between a densely connected layer and a convolution layer is this: Dense layers learn global patterns in their input feature space, whereas convolution layers learn local patters: in the case of images, patterns found in small 2D windows of the inputs. This key characteristic gives convolutional neural networks two interesting properties: (1) the patterns they learn are translation invariant and (2) they can learn spatial hierarchies of patterns.

Regarding the first, after learning a certain pattern in the lower-right corner of a picture, a convolution layer can recognize it anywhere: for example, in the upper-left corner. A densely connected network would learn the pattern anew if it appeared at a new location. This makes convolutional neural networks data efficient because they need fewer training samples to learn representations they have generalization power.

Regarding the second, a first convolution layer can learn small local patterns such as edges, a second convolution layer will learn larger patterns made of the features of the first layers, and so on. This allows convolutional neural networks to efficiently learn increasingly complex and abstract visual concepts.

A convolutional neural network learns highly non-linear mappings by interconnecting layers of artificial neurons arranged in many different layers with activation functions that make the layers dependent. It includes one or more convolutional layers, interspersed with one or more sub-sampling layers and non-linear layers, which are typically followed by one or more fully connected layers. Each element of the convolutional neural network receives inputs from a set of features in the previous layer. The convolutional neural network learns concurrently because the neurons in the same feature map have identical weights. These local shared weights reduce the complexity of the network such that when multi-dimensional input data enters the network, the convolutional neural network avoids the complexity of data reconstruction in feature extraction and regression or classification process.

Convolutions operate over 3D tensors, called feature maps, with two spatial axes (height and width) as well as a depth axis (also called the channels axis). For an RGB image, the dimension of the depth axis is 3, because the image has three color channels; red, green, and blue. For a black-and-white picture, the depth is 1 (levels of gray). The convolution operation extracts patches from its input feature map and applies the same transformation to all of these patches, producing an output feature map. This output feature map is still a 3D tensor: it has a width and a height. Its depth can be arbitrary, because the output depth is a parameter of the layer, and the different channels in that depth axis no longer stand for specific colors as in RGB input; rather, they stand for filters. Filters encode specific aspects of the input data: at a height level, a single filter could encode the concept "presence of a face in the input," for instance.

For example, the first convolution layer takes a feature map of size (28, 28, 1) and outputs a feature map of size (26, 26, 32): it computes 32 filters over its input. Each of these 32 output channels contains a 26×26 grid of values, which is a response map of the filter over the input, indicating the response of that filter pattern at different locations in the input. That is what the term feature map means: every dimension in the depth axis is a feature (or filter), and the 2D tensor output [:, n] is the 2D spatial map of the response of this filter over the input.

Convolutions are defined by two key parameters: (1) size of the patches extracted from the inputs—these are typically 1×1, 3×3 or 5×5 and (2) depth of the output feature map—the number of filters computed by the convolution. Often these start with a depth of 32, continue to a depth of 64, and terminate with a depth of 128 or 256.

Figure 10:
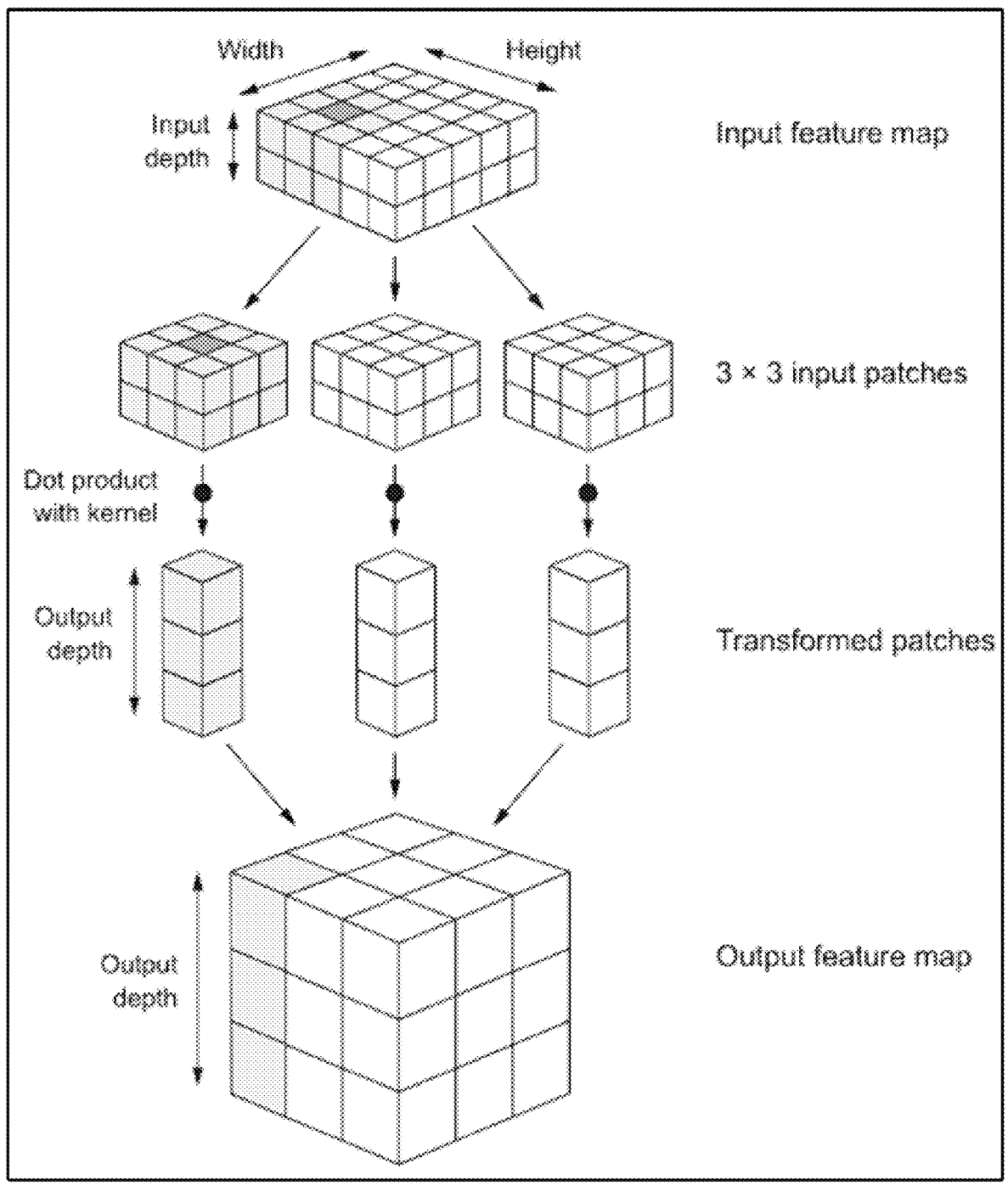
FIG. 10 illustrates an implementation of a convolutional neural network suitable for implementing the disclosed technology.

A convolution works by sliding these windows of size 3×3 or 5×5 over the 3D input feature map, stopping at every location, and extracting the 3D patch of surrounding features (shape (window_height, window_width, input_depth)). Each such 3D patch is ten transformed (via a tensor product with the same learned weight matrix, called the convolution kernel) into a 1D vector of shape (output_depth). All of these vectors are then spatially reassembled into a 3D output map of shape (height, width, output_depth). Every spatial location in the output feature map corresponds to the same location in the input feature map (for example, the lower-right corner of the output contains information about the lower-right corner of the input). For instance, with 3×3 windows, the vector output [i, j, :] comes from the 3D patch input [i−1: i+1, j−1:J+1, :]. The full process is detailed in FIG. 10, illustrating an implementation of a convolutional neural network suitable for implementing the disclosed technology.

The convolutional neural network comprises convolution layers which perform the convolution operation between the input values and convolution filters (matrix of weights) that are learned over many gradient update iterations during the training. Let (m, n) be the filter size and W be the matrix of weights, then a convolution layer performs a convolution of the W with the input X by calculating the dot product W·x+b, where x is an instance of X and b is the bias. The step size by which the convolution filters slide across the input is called the stride, and the filter area (m×n) is called the receptive field. A same convolution filter is applied across different positions of the input, which reduces the number of weights learned. It also allows location invariant learning, i.e., if an important pattern exists in the input, the convolution filters learn it no matter where it is in the sequence.

Training a Convolutional Neural Network

Figure 11:
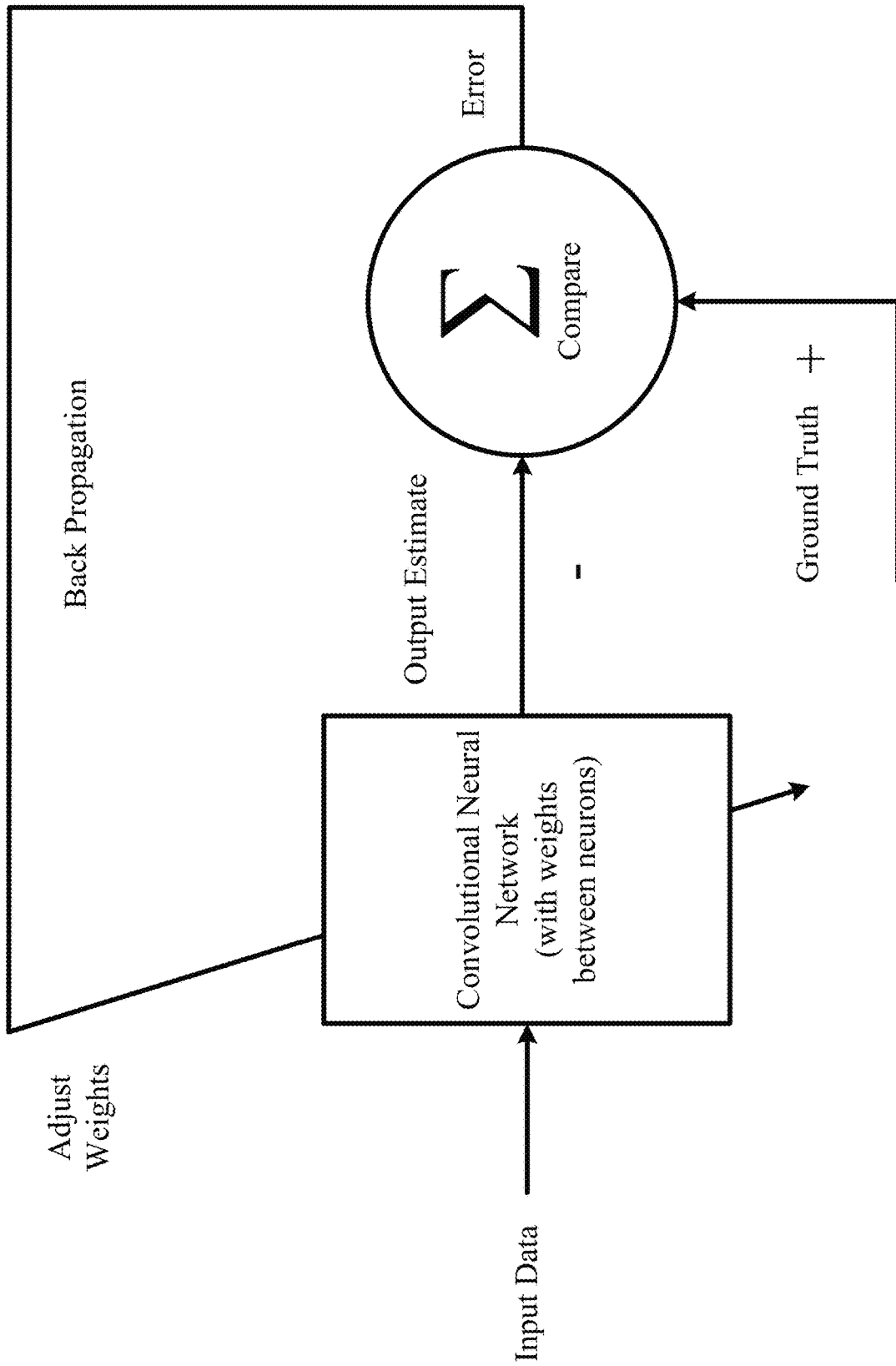
FIG. 11 depicts a block diagram of training a convolutional neural network in accordance with one implementation of the technology disclosed.

FIG. 11 depicts a block diagram of training a convolutional neural network in accordance with one implementation of the technology disclosed. The convolutional neural network is adjusted or trained so that the input data leads to a specific output estimate. The convolutional neural network is adjusted using back propagation based on a comparison of the output estimate and the ground truth until the output estimate progressively matches or approaches the ground truth.

The convolutional neural network is trained by adjusting the weights between the neurons based on the difference between the ground truth and the actual output. This is mathematically described as:

$$\Delta w_i = x_i \delta$$

where $\delta$ = (ground truth) − (actual output)

In one implementation, the training rule is defined as:

$$wnm \leftarrow w_{nm} + \alpha(t_m - \varphi_m)a_n$$

In the equation above: the arrow indicates an update of the value; to is the target value of neuron m; $\varphi_m$ is the computed current output of neuron m; $a_n$ is input n; and $\alpha$ is the learning rate.

The intermediary step in the training includes generating a feature vector from the input data using the convolution layers. The gradient with respect to the weights in each layer, starting at the output, is calculated. This is referred to as the backward pass, or going backwards. The weights in the network are updated using a combination of the negative gradient and previous weights.

In one implementation, the convolutional neural network uses a stochastic gradient update algorithm (such as ADAM) that performs backward propagation of errors by means of gradient descent. One example of a sigmoid function based back propagation algorithm is described below:

$$\varphi = f(h) = \frac{1}{1+e^{-h}}$$

In the sigmoid function above, h is the weighted sum computed by a neuron. The sigmoid function has the following derivative:

$$\frac{\partial \varphi}{\partial h} = \varphi(1-\varphi)$$

The algorithm includes computing the activation of all neurons in the network, yielding an output for the forward pass. The activation of neuron m in the hidden layers is described as:

$$\varphi_m = \frac{1}{1+e^{-h_m}}$$

$$h_m = \sum_{n=1}^{N} a_n w_{nm}$$

This is done for all the hidden layers to get the activation described as:

$$\varphi_k = \frac{1}{1+e^{h_k}}$$

$$h_k = \sum_{m=1}^{M} \varphi_m v_{mk}$$

Then, the error and the correct weights are calculated per layer. The error at the output is computed as:

$$\delta_{ok}=(t_k-\varphi_k)\varphi_k(1-\varphi_k)$$

The error in the hidden layers is calculated as:

$$\delta_{hm} = \varphi_m(1-\varphi_m)\sum_{k=1}^{K} v_{mk}\delta_{ok}$$

The weights of the output layer are updated as:

$$V_{mk} \leftarrow V_{mk} + \alpha\delta_{ok}\varphi_m$$

The weights of the hidden layers are updated using the learning rate α as:

$$v_{nm} \leftarrow w_{nm} + \alpha\delta_{hm}a_n$$

In one implementation, the convolutional neural network uses a gradient descent optimization to compute the error across all the layers. In such an optimization, for an input feature vector x and the predicted output ŷ, the loss function is defined as l for the cost of predicting ŷ when the target is y, i.e. l(ŷ, y). The predicted output l is transformed from the input feature vector x using function $f$. Function $f$ is parameterized by the weights of convolutional neural network, i.e. $\hat{y}=f_w(x)$. The loss function is described as $l(\hat{y}, y)=l(f_w(x), y)$, or $Q(z, w)=l(f_w(x), y)$ where z is an input and output data pair (x, y). The gradient descent optimization is performed by updating the weights according to:

$$v_{t+1} = \mu v_t - \alpha \frac{1}{n}\sum_{i=1}^{N} \nabla w_t Q(z_t, w_t)$$

$$w_{t+1} = w_t + v_{t+1}$$

In the equations above, α is the learning rate. Also, the loss is computed as the average over a set of n data pairs. The computation is terminated when the learning rate α is small enough upon linear convergence. In other implementations, the gradient is calculated using only selected data pairs fed to a Nesterov's accelerated gradient and an adaptive gradient to inject computation efficiency.

In one implementation, the convolutional neural network uses a stochastic gradient descent (SGD) to calculate the cost function. A SGD approximates the gradient with respect to the weights in the loss function by computing it from only one, randomized, data pair, $z_t$, described as:

$$v_{t+1}=\mu v-\alpha \nabla wQ(z_t,w_t)$$

$$w_{t+1}=w_t+v_{t+1}$$

In the equations above: α is the learning rate; μ is the momentum; and t is the current weight state before updating. The convergence speed of SGD is approximately O(1/t) when the learning rate α are reduced both fast and slow enough. In other implementations, the convolutional neural network uses different loss functions such as Euclidean loss and softmax loss. In a further implementation, an Adam stochastic optimizer is used by the convolutional neural network.

Convolution Layers

The convolution layers of the convolutional neural network serve as feature extractors. Convolution layers act as adaptive feature extractors capable of learning and decomposing the input data into hierarchical features. In one implementation, the convolution layers take two images as input and produce a third image as output. In such an implementation, convolution operates on two images in two-dimension (2D), with one image being the input image and the other image, called the "kernel", applied as a filter on the input image, producing an output image. Thus, for an input vector $f$ of length n and a kernel g of length m, the convolution $f*g$ of $f$ and g is defined as:

$$(f*g)(i) = \sum_{j=1}^{m} g(j) \cdot f(i-j+m/2)$$

The convolution operation includes sliding the kernel over the input image. For each position of the kernel, the overlapping values of the kernel and the input image are multiplied and the results are added. The sum of products is the value of the output image at the point in the input image where the kernel is centered. The resulting different outputs from many kernels are called feature maps.

Once the convolutional layers are trained, they are applied to perform recognition tasks on new inference data. Since the convolutional layers learn from the training data, they avoid explicit feature extraction and implicitly learn from the training data. Convolution layers use convolution filter kernel weights, which are determined and updated as part of the training process. The convolution layers extract different features of the input, which are combined at higher layers. The convolutional neural network uses a various number of convolution layers, each with different convolving parameters such as kernel size, strides, padding, number of feature maps and weights.

Learning Models

Implementation specifics will differ widely by application, however anomaly recognition and remediation generally include embodiments in which interface server(s) 102 implement via learning model(s) 134 a statistical learning based process (e.g., an "AI agent") that performs tracking a global state of events in an accessed block chain, identifying anomalies, and deciding to trigger gathering additional information and/or filing a report to another entity. Data points in the events of the accessed block chain are represented by a vector (more generally a tensor) for each data point. Data points in the events can include structured or unstructured data; each can be manipulated using different methods. Programming a mapping to map "structured data" to a vector representation will capture the relevant data of an object, e.g., what's gleaned from scanning a bar code can be mapped to fields in the vector. A pre-trained model can be applied to map unstructured data to a vector (or tensor) representation.

Implementations at the start of their deployment, experience a dearth of labeled data from which to make decisions. Over time, however, as the implementation processes data and takes actions, e.g., detecting events, classifying events as anomalies, and triggering reporting of the anomalies, the results of these actions will produce labelled data. The dynamics of this process mean that implementations starting with an unsupervised learning processes and transition to a semi-supervised learning processes over time with usage. Unsupervised learning processes take similar pieces of data and map them to mathematical objects that are just as similar. Semi-supervised learning processes are applied to instances where some labels are applied to the data, but there are far more unlabeled data than labelled ones.

Figure 12A:
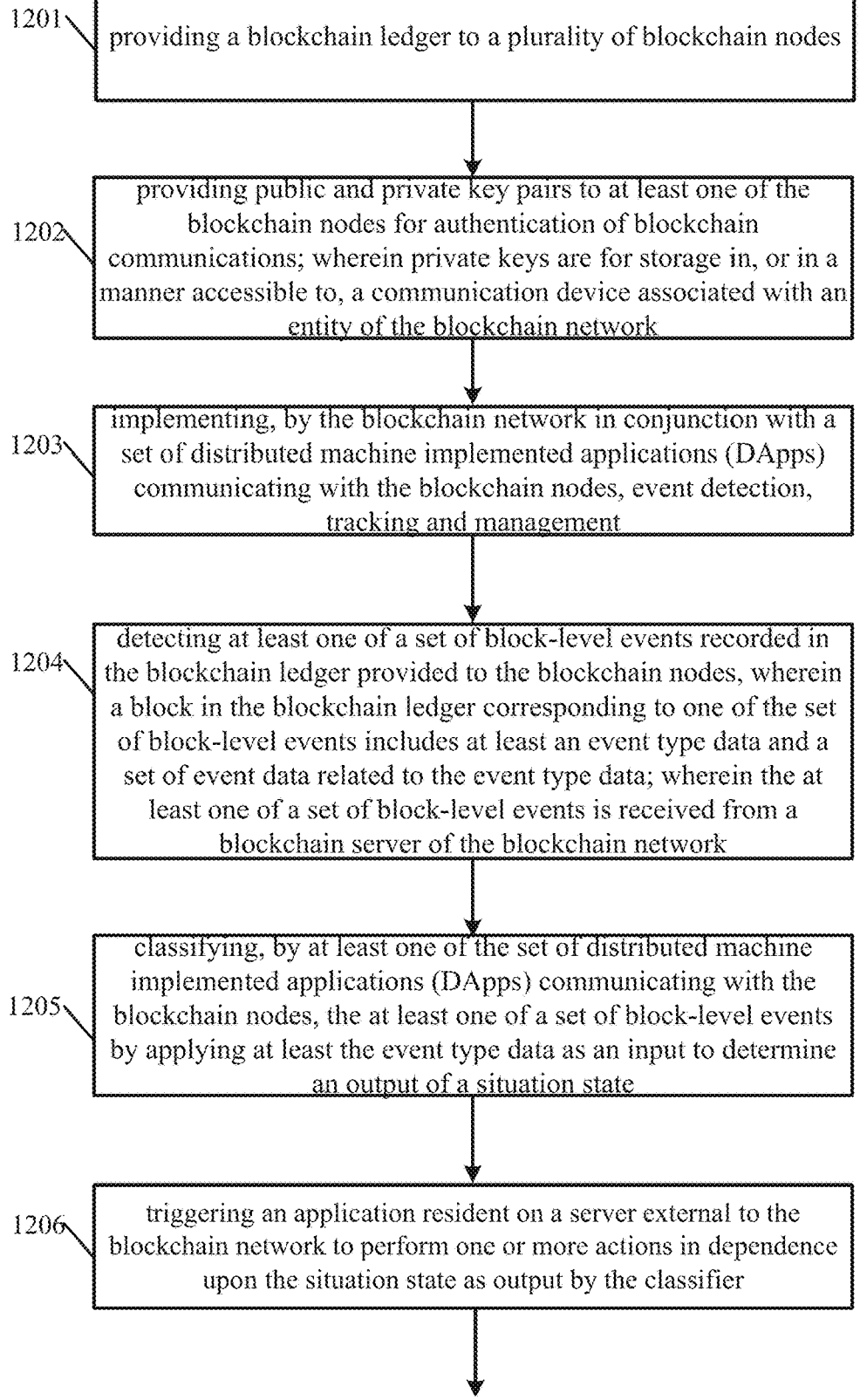
FIG. 12A is a flowchart illustrating a method for establishing a blockchain network implementing event detection, tracking and management for rule-based compliance, according to various embodiments.

FIG. 12A is a flowchart illustrating a method for establishing a blockchain network implementing event detection, tracking and management for rule-based compliance, according to various embodiments. Accordingly, in the flowchart 1200A, at block 1201, a blockchain ledger 106 of FIG. 1A, FIG. 1B is provided to a plurality of blockchain nodes (e.g., 102, 136 of FIG. 1A, FIG. 1B).

In block 1202, public and private key pairs are provided to at least one of the blockchain nodes 102 of FIG. 1A, FIG. 1B for authentication of blockchain communications. In various embodiments, private keys are for storage in, or in a manner accessible to, a communication device associated with an entity 102 of FIG. 1A, FIG. 1B.

In block 1203, the blockchain network in conjunction with a set of distributed machine implemented applications (DApps) (e.g., 112 of FIG. 1A, 114 of FIG. 1A, 115 of FIG. 1A) communicating with the blockchain nodes, implements event detection, tracking and management.

In block 1204, the event hub 115 of FIG. 1A detects at least one of a set of block-level events recorded in the blockchain ledger provided to the blockchain nodes. A block in the blockchain ledger corresponds to one of the set of block-level events includes at least an event type data and a set of event data related to the event type data. The at least one of a set of block-level events is received from a blockchain server (e.g., 102, 136 of FIG. 1A, FIG. 1B) of the blockchain network 106 of FIG. 1A, FIG. 1B.

In block 1205, at least one of the set of distributed machine implemented applications (DApps) (e.g., 112 of FIG. 1, 114 of FIG. 1, 115 of FIG. 1A) communicating with the blockchain nodes classifies the at least one of a set of block-level events by applying at least the event type data as an input to determine an output of a situation state.

In block 206, triggering an application resident on a server external to the blockchain network to perform one or more actions in dependence upon the situation state as output by the classifier (e.g., 112 of FIG. 1A, 114 of FIG. 1A, 115 of FIG. 1A).

Figure 12B:
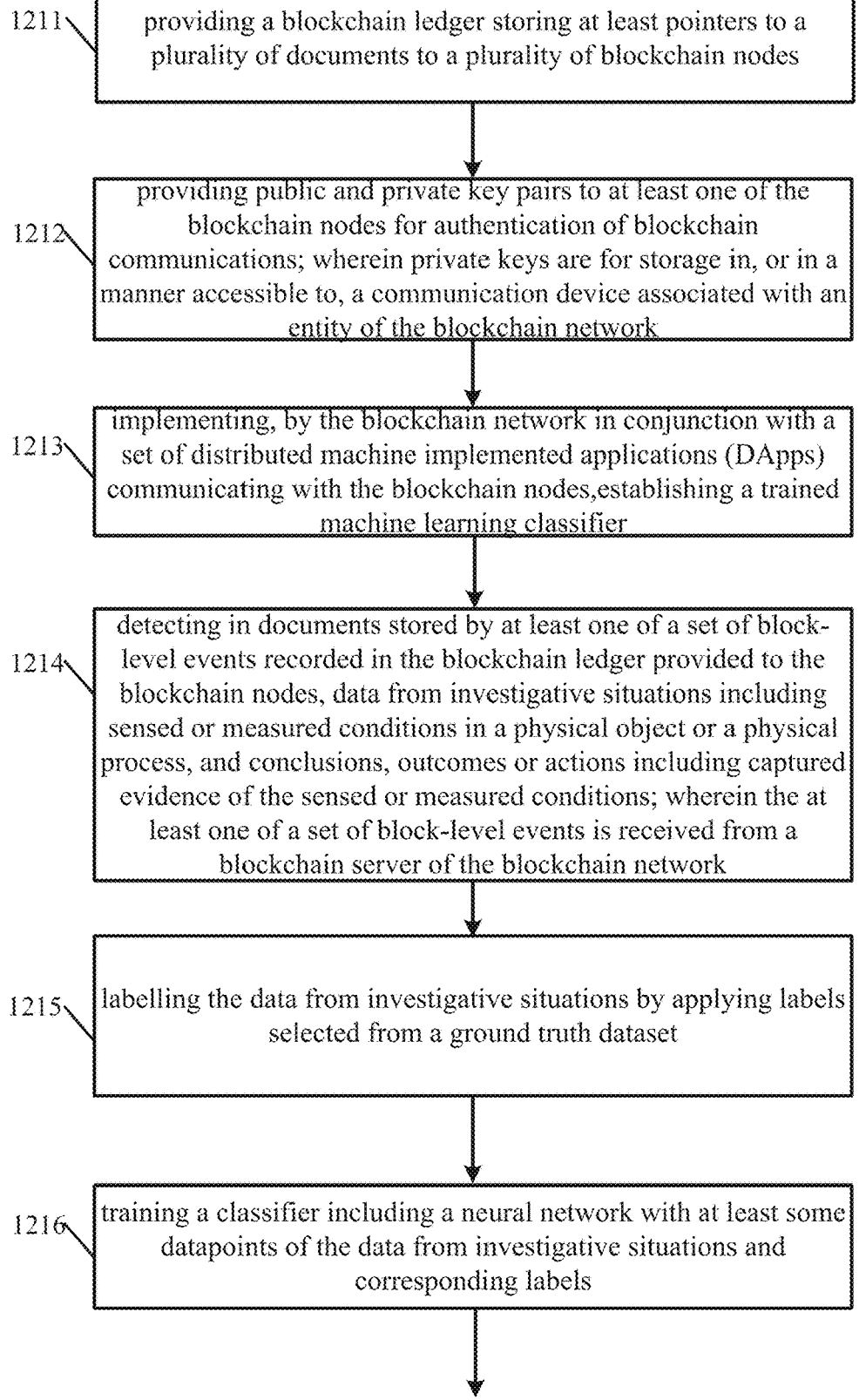
FIG. 12B is a flowchart illustrating a method for establishing a trained machine learning classifier using a blockchain network, according to various embodiments.

FIG. 12B is a flowchart illustrating a method for establishing a trained machine learning classifier using a blockchain network, according to various embodiments. Accordingly, in the flowchart 1200B, at block 1211, a blockchain ledger storing at least pointers to a plurality of documents 106 of FIG. 1A, FIG. 1B is provided to a plurality of blockchain nodes (e.g., 102, 136 of FIG. 1A, FIG. 1B).

In block 1212, public and private key pairs are provided to at least one of the blockchain nodes 102 of FIG. 1A, FIG. 1B for authentication of blockchain communications. In various embodiments, private keys are for storage in, or in a manner accessible to, a communication device associated with an entity 102 of FIG. 1A, FIG. 1B.

In block 1213, the blockchain network in conjunction with a set of distributed machine implemented applications (DApps) (e.g., 112 of FIG. 1A, 114 of FIG. 1A, 115 of FIG. 1A) communicating with the blockchain nodes, implements establishing a trained machine learning classifier.

In block 1214, the event hub 115 of FIG. 1A detects data from investigative situations including sensed or measured conditions in a physical object or a physical process, and conclusions, outcomes or actions in documents stored by at least one of a set of block-level events recorded in the blockchain ledger provided to the blockchain nodes. The data can include captured evidence of the sensed or measured conditions. The at least one of a set of block-level events is received from a blockchain server (e.g., 102, 136 of FIG. 1A, FIG. 1B) of the blockchain network 106 of FIG. 1A, FIG. 1B.

In block 1215, at least one of the set of distributed machine implemented applications (DApps) (e.g., 112 of FIG. 1, 114 of FIG. 1, 115 of FIG. 1A) communicating with the blockchain nodes labels the data from investigative situations by applying labels selected from a ground truth dataset.

In block 1216, a classifier including a neural network is trained with at least some datapoints of the data from investigative situations and corresponding labels (e.g., 112 of FIG. 1A, 114 of FIG. 1A, 115 of FIG. 1A).

Figure 12C:
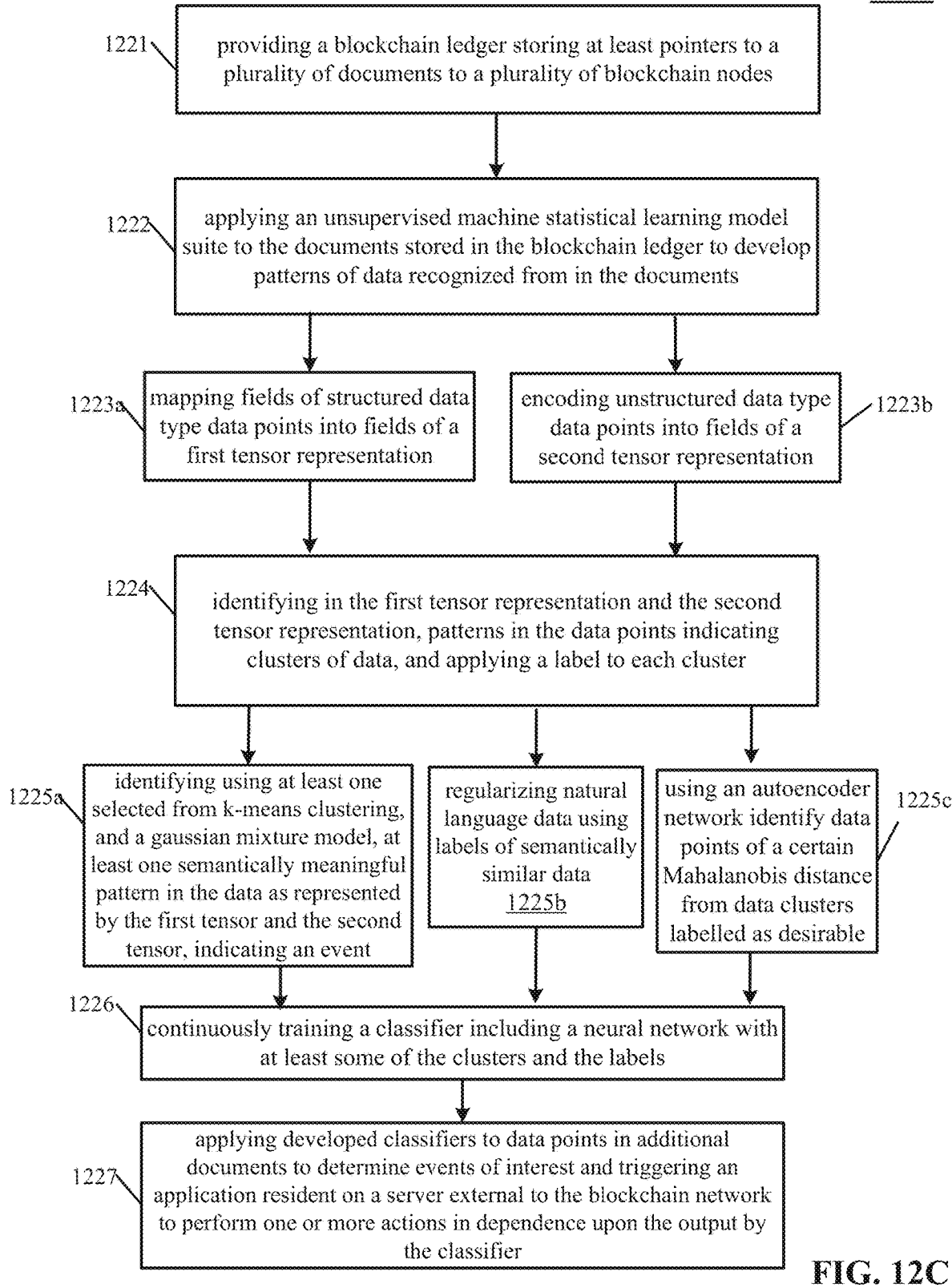
FIG. 12C is a flowchart illustrating a method for establishing a trained machine learning classifier using unsupervised machine learning in a blockchain network.

FIG. 12C is a flowchart illustrating a method for establishing a trained machine learning classifier using unsupervised machine learning in a blockchain network. The blockchain network can implement event detection, tracking and management for situation analysis. According to various embodiments, data from clinical trials can be developed into classifiers suited for semi-supervised and supervised machine learning applications by application of unsupervised machine learning techniques.

Accordingly, in the flowchart 1200C, at block 1221, a blockchain ledger 106 of FIG. 1A, FIG. 1B is provided to a plurality of blockchain nodes (e.g., 102, 136 of FIG. 1A, FIG. 1B). The blockchain ledger is preferably storing at least addressing information or pointers to a plurality of documents. Documents can include documents such as clinical trial documents, reports made by governmental agencies, papers published by universities, and so forth.

In block 1222, an unsupervised machine statistical learning model suite (e.g., 134 of FIG. 1A, FIG. 1B) is applied to the documents stored in the blockchain ledger to develop patterns of data recognized from in the documents. Data points in the documents can include structured or unstructured data; each can be manipulated using different methods.

In block 1223a, fields of structured data type data points are mapped into fields of a first tensor representation. Programming a mapping to map "structured data" to a vector representation will capture the relevant data of an object, e.g., what's gleaned from scanning a bar code can be mapped to fields in the vector.

In block 1223b, encoding unstructured data type data points into fields of a second tensor representation. A pre-trained model can be applied to map unstructured data to a vector (or tensor) representation. For example, for textual data, an 'encoder' model takes as input text and maps it to a relatively small vector. A 'decoder' model takes as input that vector and maps it back to text. By training both networks (e.g., encoder, decoder) to minimize the difference between the reconstructed text and the input text, results in an encoder that learns how to represent such text as a tiny vector. This resulting tiny vector can be appended to any other vector. This technique also is effective for images and other unstructured data. The general concept of taking data, mapping it to a small vector(s), and back to itself in order to learn how to represent it as vectors is called autoencoding.

In block 1224, patterns indicating clusters of data are identified in the data points associated with the first tensor representation and the second tensor representation, and a label is applied to each cluster. Numerous possible factors and patterns identified using a statistical model, such as a neural network, kernel method, or a Principal Component Analysis (PCA) to map block level data into a latent vector space. Patterns identified can be investigated by reading/writing from other nodes in the blockchain ledger of blockchain network (106 of FIG. 1A, FIG. 1B) to find like data and reveal previous labelling, and/or treatments of such like data. Meaning can be assigned to the patterns identified, based on the results of such investigations. Such conclusions can be written to a datastore that interface server(s) 102 has access.

In block 1225a, at least one selected from k-means clustering, and a gaussian mixture model, is used to identify at least one semantically meaningful pattern indicating an event in the data as represented by the first tensor and the second tensor.

In block 1225b, natural language data is regularized using labels assigned to clusters of semantically similar data.

In block 1225c, an autoencoder network is used to identify data points of a certain Mahalanobis distance from data clusters labelled as desirable. Autoencoders can be implemented by neural networks that take as input the data, map it to small vectors and back to itself in order to learn how to represent it as vectors. In one implementation and by way of example, in an autoencoder is trained to represent a clinical study summary as a small vector, the text encoder (e.g. implemented using an RNN or Transformer) creates a 50-dimensional vector representing the text of the study, and appends to it a one dimensional vector that represents the outcome score. The 51-dimensional vector that results, termed a latent vector, captures both components of information of the study, and can serve as input to another model.

Figure 12D:
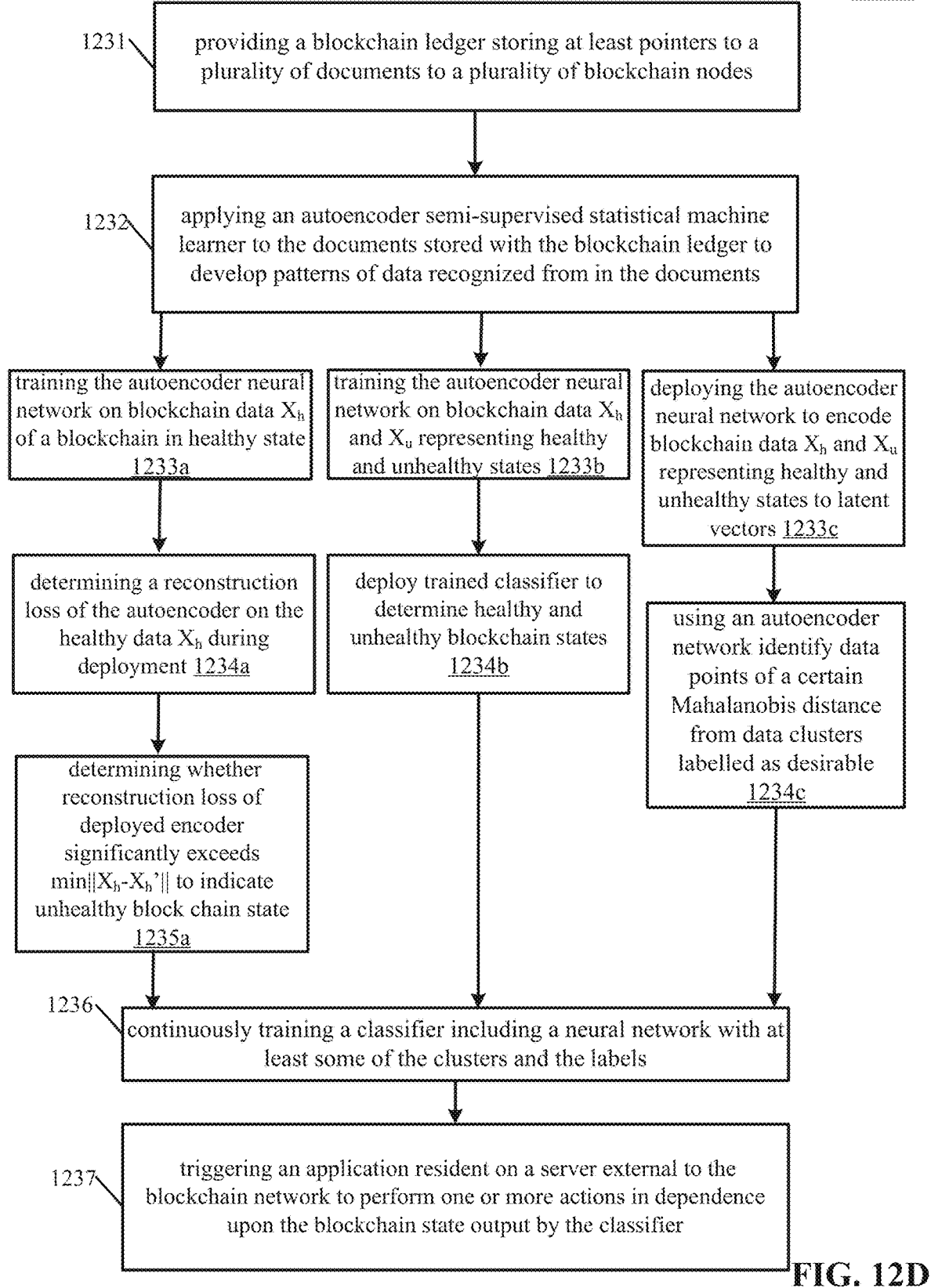
FIG. 12D is a flowchart illustrating a method for establishing a trained machine learning classifier using semi-supervised machine learning for classifying nodes in a blockchain network in a healthy blockchain network state(s) or an unhealthy blockchain network state(s).

An autoencoder implementation is described in further detail herein with reference to FIG. 12D.

In block 1226, a classifier is developed by continuously training a classifier including a neural network with at least some of the clusters and the labels. A classifier can now be trained (or retrained) on the labelled patterns identified, by accessing a privileged datastore. Training a classifier is described in further detail hereinbelow with reference to FIG. 12C.

In block 1227, the developed classifiers are applied to data points in additional documents to determine events of interest and triggering an application resident on a server external to the blockchain network to perform one or more actions in dependence upon the output by the classifier. For example, interface server(s) 102 can proactively act on identified events of interest discovered by reading/writing from the blockchain 106.

Cluster Identification.

Figure 13A:
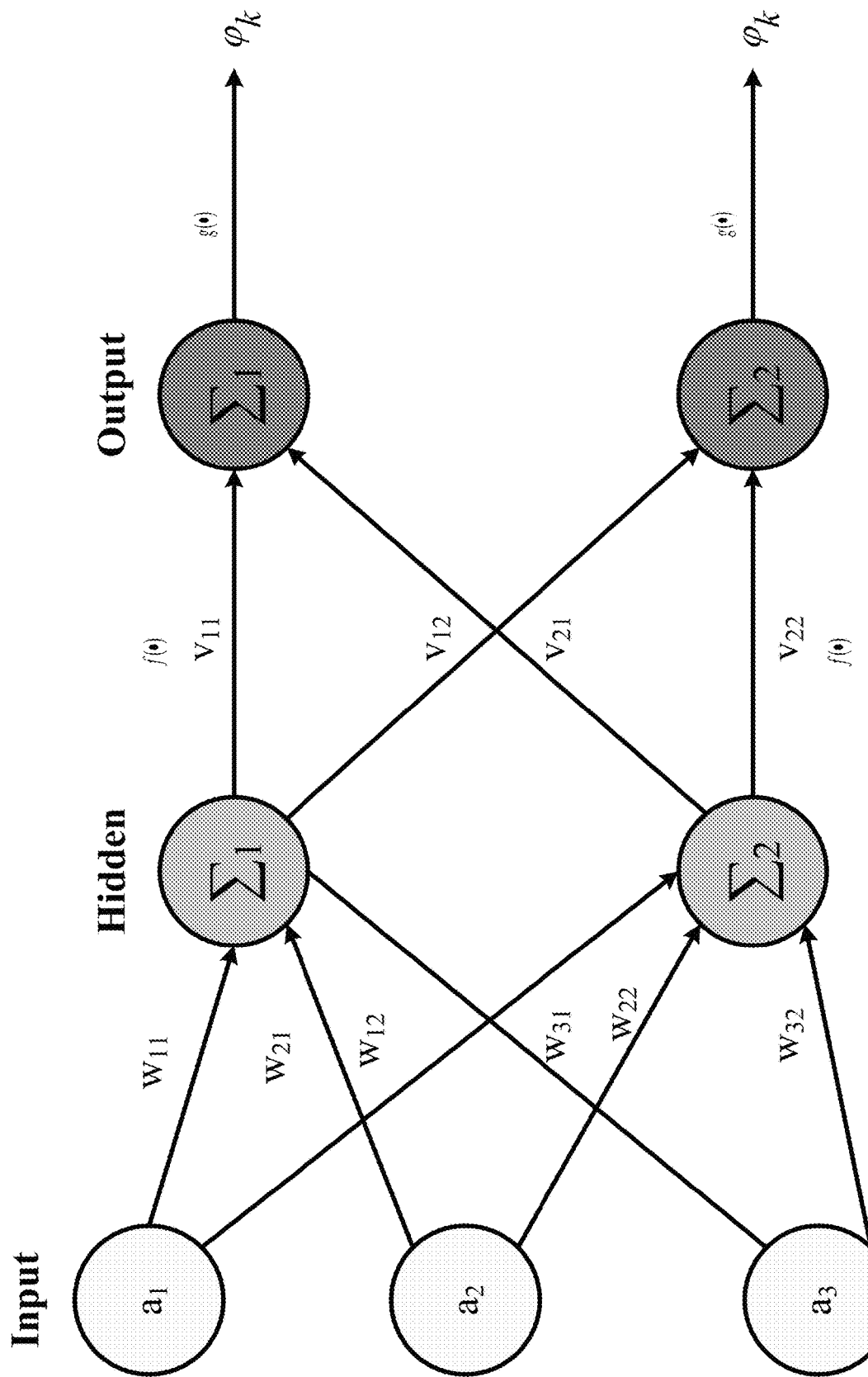
FIG. 13A illustrates a representative neural network suitable for implementing the disclosed technology.

In an implementation, block level events are detected in the blockchain ledger by clustering the blocks according to numerous possible factors and patterns identified using a statistical model, such as a neural network, kernel method, or a Principal Component Analysis (PCA) to map block level data into a latent vector space:

FIG. 13A illustrates a representative neural network suitable for implementing the disclosed technology. Neural network 1300A is a fully connected neural network with multiple layers. A neural network is a system of interconnected artificial neurons (e.g., $a_1$, $a_2$, $a_3$) that exchange messages between each other. Neural network 1300A has three inputs, two neurons in the hidden layer and two neurons in the output layer. The hidden layer has an activation function $f(\bullet)$ and the output layer has an activation function $g(\bullet)$. The connections have numeric weights (e.g., $w_{11}$, $w_{21}$, $w_{12}$, $w_{31}$, $w_{22}$, $w_{32}$, $v_{11}$, $v_{12}$, $v_{21}$, $v_{22}$) that are tuned during the training process, so that a properly trained network responds correctly when fed an image to recognize. The input layer processes the raw input, the hidden layer processes the output from the input layer based on the weights of the connections between the input layer and the hidden layer. The output layer takes the output from the hidden layer and processes it based on the weights of the connections between the hidden layer and the output layer. The network includes multiple layers of feature-detecting neurons. Each layer has many neurons that respond to different combinations of inputs from the previous layers. These layers are constructed so that the first layer detects a set of primitive patterns in the input image data, the second layer detects patterns of patterns and the third layer detects patterns of those patterns.

Kernel methods include the classifier begins with the i-th training example, $(x_i, y_i)$ learns for it a corresponding weight $w_i$. Prediction for unlabeled inputs, i.e., those not in the training set, is treated by the application of a similarity function k, called a kernel, between the unlabeled input x' and each of the training inputs $x_i$ An example kernel binary classifier computes a weighted sum of similarities:

$$\hat{y} = \text{sgn} \sum_{i=1}^{n} w_i y_i k(X_i X')$$

where: $\hat{y} \in \{-1, +1\}$ is the kernelized binary classifiers predicted label for the unlabeled input x', k: X×X→R is the kernel function that measures similarity between any pair of inputs x, x'∈ $X_i$; the sum ranges over the n labeled examples $\{(x_i, y_i)\}_{i=1}^n$ in the classifier's training set, with $y_i \in \{-1, +1\}$; the $w_i \in R$ are the weights for the training examples, as determined by the learning algorithm; the sign function sgn determines whether the predicted classification $\hat{y}$ comes out positive or negative. Reference may be had by persons skilled in the art to Wikipedia, en.wikipedia.org/wiki/Kernel_method, for further information concerning kernel method.

Principal Component Analysis (PCA) is mathematically defined as an orthogonal linear transformation that transforms the data to a new coordinate system such that the greatest variance by some scalar projection of the data comes to lie on the first coordinate (called the first principal component), the second greatest variance on the second coordinate, and so on. In one implementation, a p-dimensional ellipsoid is fit to the data, where each axis of the ellipsoid represents a principal component. If some axis of the ellipsoid is small, then the variance along that axis is also small, and by omitting that axis and its corresponding principal component from our representation of the dataset, we lose only an equally small amount of information. Reference may be had by persons skilled in the art to Wikipedia, en.wikipedia.org/wiki/Principal_component_analysis for further information concerning principle component analysis.

At this point, an unsupervised learning algorithm such as k-means clustering, or a gaussian mixture model is used to identify in the data semantically meaningful patterns indicating an event. For example, similarities identified in clusters indicate an event, e.g. a headache after taking pills could be clustered to a lot (i.e., bad production event), to a time (swapped pills event), or to a location (damaged while shipping event). Each field in the FDA 3911 report would be tagged in a block level data structure that can be shared on the blockchain. Implementations can enable easier sorting of events and issuing notifications. For example, a rash of seemingly unrelated events in the opiate category might point back to a specific problematic manufacturing lot, while other correspondences between reports could reveal fraudulent activity.

Regularizing Free-Form Typical Input Learning.

People have many different ways of describing the same thing, which can confound traditional reporting systems. The system could regularize input by suggesting typical responses and verifying hypothesized clusters by suggesting responses. One implementation can regularize data by mapping it into a semantically meaningful vector space, learned from a large corpus of data. In the case of "regularizing" natural language input, this may be a space learned from training a sequence to sequence model statistical model/ neural network to encode text to a vector and that vector back to the original text. The resultant vectors encode the 'meaning' of the input text. As such, similar text inputs can be easily grouped together. If those groups are labelled, the labels can be easily suggested. (For instance, a user may write "pills look weird," the system might suggest "damaged pills" or "pills look different than normal" as options. Using natural-language generation, the AI would then ask several follow-up questions to look for a match that builds out a cluster and provides context for its image-recognition efforts.)

Autoencoder Network for Bad Actor Identification

FIG. 12D is a flowchart illustrating a method for establishing a trained machine learning classifier using unsupervised machine learning for classifying nodes in a blockchain network in a healthy blockchain network state(s) or an unhealthy blockchain network state. The blockchain network can implement event detection, tracking and management for situation analysis or other purposes. According to various embodiments, data from compliance reporting, data from clinical trials, and/or data from manufacturing and distribution processes can be developed into classifiers suited for semi-supervised and supervised machine learning applications by application of unsupervised machine learning techniques.

Accordingly, in the flowchart 1200D, at block 1231, a blockchain ledger 106 of FIG. 1A, FIG. 1B is provided to a plurality of blockchain nodes (e.g., 102, 136 of FIG. 1A, FIG. 1B). The blockchain ledger is preferably storing at least addressing information or pointers to a plurality of documents. Documents can include documents such as clinical trial documents, reports made by governmental agencies, papers published by universities, reports created or managed by participants in the course of manufacturing and distribution processes, and so forth.

Figure 13B:
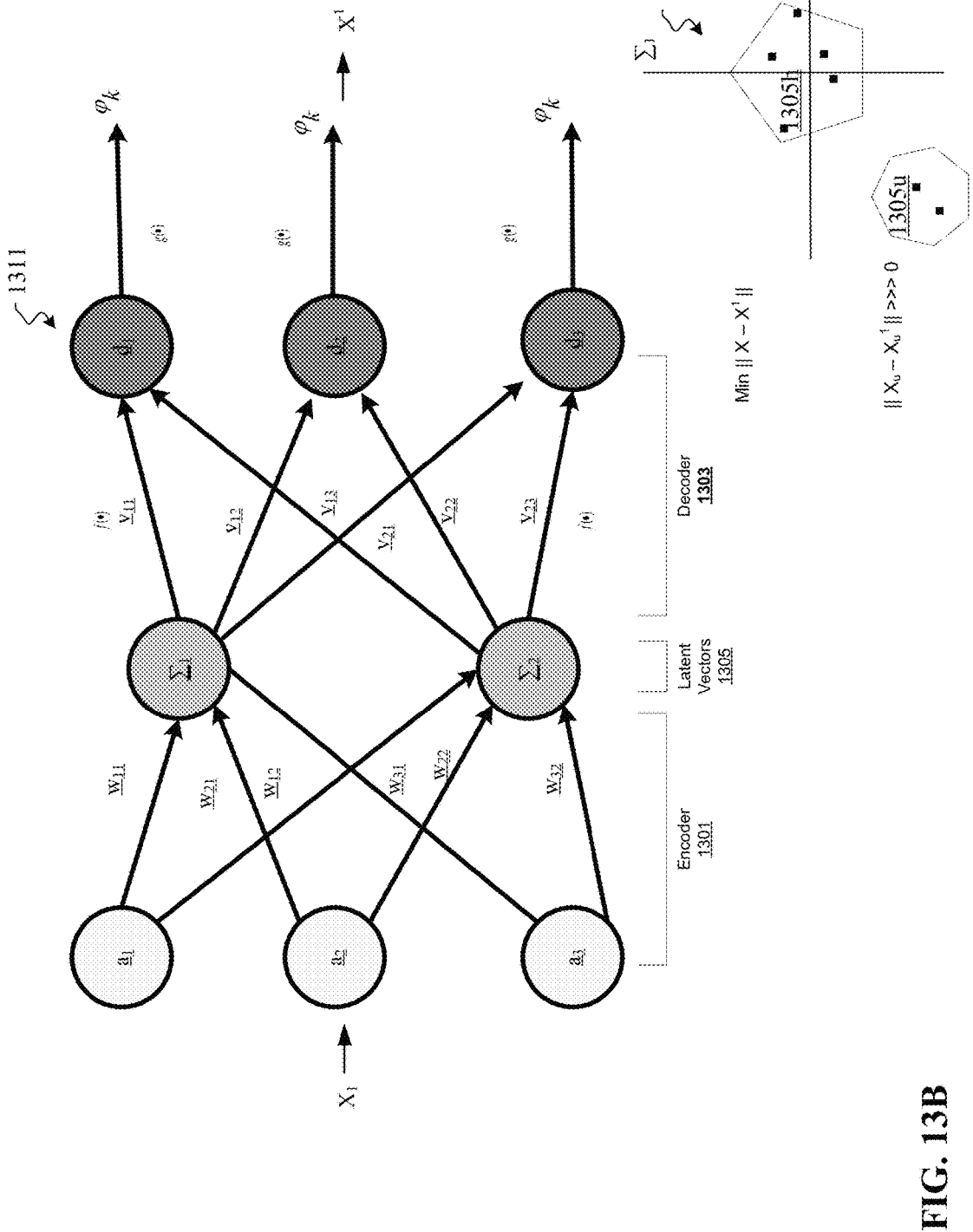
FIG. 13B illustrates using a neural network for implementing autoencoding to detect a blockchain network health state of a block chain.

In block 1232, an autoencoder semi-supervised statistical machine learner is applied to the documents stored in the blockchain ledger (e.g., pointed upon or stored in accordance with) to develop patterns of data recognized from in the documents. The autoencoder can be stand alone or a component of an unsupervised machine statistical learning model suite (e.g., 134 of FIG. 1A, FIG. 1B). One implementation of an autoencoder semi-supervised statistical machine learner is representative neural network 1311 illustrated by FIG. 13B, in which a neural network 1311 is used for implementing autoencoding to detect anomalous data, such as a spam, corrupt data, or data indicative of an anomaly in compliance reporting, data from clinical trials, and/or data from manufacturing and distribution processes or other bad data in the block chain.

In block 1233a, autoencoder neural network 1311 (e.g., based on an RNN or transformer) is trained on 'healthy' blockchain data $x_h$. Healthy blockchain data $x_h$, while application dependent, can include specific params such as transactions against the blockchain ledger per second, percentage of transactions recorded in the blockchain ledger that include transactions between pharmaceutical suppliers and wholesalers, percentage of transactions recorded in the blockchain ledger that include transactions between wholesaler and pharmacy, percentage of transactions recorded in the blockchain ledger that include transactions between pharmaceutical manufacturer and wholesalers. Number of transactions recorded in the blockchain ledger that include transactions occurring between industry participants and others. While neural network autoencoder 1311 is illustrated generally with 3 input nodes, 2 internal or hidden nodes and 3 output nodes, implementations will include different and varying configurations. For example, one implementation might receive data x comprising 1024-dimensional data, compress the data to latent vectors 1305, which may be as small as single dimensional data, and then re-inflate the data to output data $x^1$ of 1024 dimensions.

In block 1234a a 'reconstruction loss' $\|x_h - x_h^1\|$ of the autoencoder is measured on the healthy data $x_h$. The classifier, having been trained on 'healthy data'—e.g., data for a blockchain in normal state—only, will not reconstruct input for unhealthy data as well as healthy data at run time. In a block 1235a, when the autoencoder is deployed a blockchain in a normal or healthy blockchain state will exhibit a minimal reconstruction loss, i.e., min $\|x_h - x_h^1\|$. If the 'reconstruction loss' is substantially higher on data during deployment, e.g., against a threshold, and/or the blockchain is in an unhealthy blockchain state; in such case, the blockchain system is deemed to be 'unhealthy' or 'under attack'.

In block 1233b, alternatively when a set of historical training data is available, the encoder section 1301 of the autoencoder network 1311 is used to encode all data (e.g., healthy $x_h$ and unhealthy $x_u$) to a set of latent vectors 1305. A classifier is trained on the latent vectors, labelled with whether they represent a 'normal' or 'abnormal' blockchain state. In a block 1234b, the trained classifier can deployed to classify input data as either normal or abnormal.

In a block 1233c, alternatively the encoder 1301 is used to encode all data (e.g., healthy $x_h$ and unhealthy $x_u$) at deploy time to a latent space 1307. In latent space 1307, latent vectors 1305h will cluster about one another. In block 1234c, data points of a certain Mahalanobis (or other metric) distance from data clusters labelled as desirable are identified. Latent vectors 1305u that are, according to some distance metric (e.g. L2 or Mahalanobis distance) far from 'healthy' data points are deemed to be 'unhealthy' or as 'resulting from an attack'.

In block 1236, a classifier is developed by continuously training a classifier including a neural network with at least some of the clusters and the labels. A classifier can now be trained (or retrained) on the labelled patterns identified, by accessing a privileged datastore. Training a classifier is described in further detail hereinbelow with reference to FIG. 13C.

In block 1237, the developed classifiers are applied to data points in additional documents to determine events of interest and triggering an application resident on a server external to the blockchain network to perform one or more actions in dependence upon the output by the classifier. For example, interface server(s) 102 can proactively act on identified events of interest discovered by reading/writing from the blockchain 106.

Accordingly, implementations employing the foregoing disclosed technology can identify spam transactions on the blockchain ledger, employ learned data stored with user identity to verify claimed identity, compute confidence scores to score transactions, and automatically trigger mitigating actions to be taken by downstream applications (e.g. forced slowing of transaction rate or flagging a suspicious user for review). Atypical transactions can be flagged for possible review to catch malicious activity. In other usage scenarios, one implementation of an encoder neural network enabled interface server(s) 102 can identify improper behavior such as forced shortages and front-running.

Convolutional Neural Network (CNN)

One implementation of a neural network enabled interface server triggers prompts asking for the submitting parties to take photos and use image recognition to identify classes of problems and highly probable matches. A convolutional neural network is trained on a curated database of pill photos, labelled with defects. If defects are rare, examples of defective pills may be oversampled to provide the network with adequate inputs during training. The neural network may be given unsupervised pre-training on a dataset of unlabeled photos in order to learn latent representations of different kinds of pills and their defects, hence reducing the amount of labelled data needed to learn. One range of solutions involves comparing an image of a suspicious pill to visual databases of pills and identifying potential substitutions that may have occurred in the supply chain. Another range would include assessments of the state of the medication (e.g. color and cloudiness of a liquid medication). As a deep learning methodology designed for two-dimensional image data and requires little initial pre-processing, CNN is well-suited for this purpose.

Classifier Inputs and Outputs

An exemplary deep neural network implementation selects an appropriate classification of the illegitimate product or product with a high risk of illegitimacy using a set of inputs to the neural network. Inputs whether structured or unstructured data type data points, can be encoded into fields of a vector (or tensor) representation. Implementations will employ various levels of abstraction in configuring, classification and anomaly detection tasks, e.g., in a pharmaceutical application, data can be selected to describe pharmaceutical manufacturing lots, shipment lots, nodes in a distribution network, entities, geographies and so forth.

In one example, a neural network ensemble can implement a classifiers that are trained to classify situation states according to input data useful in regulatory compliance reporting, such as without limitation: A type of report (e.g., initial notification, follow-up notification, or request for termination), an incident number (provided by FDA) for follow-up and request for termination, a date of initial notification to FDA (MM/DD/YYYY), a date company determined product was illegitimate (MM/DD/YYYY), a name of product as it appears on the label, primary ingredients, drug use (human, other), a drug description (e.g., finished prescription drug, vaccine, plasma derivative (e.g., coagulation factors, immunoglobulins, albumin), allergenic (e.g., standardized and non-standardized), or multiple), a strength of drug (e.g., 500 mg. 1 g/10 mL), a dosage form (e.g., tablet, capsule, aerosol, oral liquid, sublingual, injectable, topical, suppository, other, or multiple), a quantity of drug (Number and Unit), an NDC (Nat'l Drug Code) number, a serial number, lot number(s), expiration date(s), (for notification) a description of event/issue, (for request for termination of notification) description of why notification is no longer necessary, other reports submitted to the FDA (e.g., FAR—Field Alert Report, BPDR—Biological Product Deviation Report, Medwatch 3500, Medwatch 3500A, none, other), company name and address, company category, manufacturer, wholesale distributer, dispenser (Pharmacy), repackager, Unique Facility Number (D-U-N-S), and contact information.

The classifier(s) once trained on a training dataset can determine a Classification of Notification (Counterfeit, Diverted, Stolen, Intentional adulteration, Unfit for distribution, Fraudulent transaction) for a particular situation state. The exemplary deep neural network implementation selects an appropriate classification of the illegitimate product or product with a high risk of illegitimacy from a set of outputs.

| Output | Determined Conditions |
| --- | --- |
| Counterfeit | A product is determined to be counterfeit, or has a high risk of being counterfeit. |
| Diverted | A product is determined to be a diverted product, or has a high risk of being a diverted product. |
| Stolen | A product is determined to be a stolen product, or has a high risk of being a stolen product. |
| Intentional adulteration | A product is determined to be intentionally adulterated such that use of the product would result in serious adverse health consequences or death to humans, or has a high risk of it. |
| Unfit for distribution | A product appears otherwise unfit for distribution such that use of the product would be reasonably likely to result in serious adverse |

-continued

| Output | Determined Conditions |
|---|---|
| | health consequences or death to humans, or has a high risk of it. |
| Fraudulent transaction | A product in your possession or control is determined to be the subject of a fraudulent transaction, or has a high risk of it. |

In one exemplary implementation, some neural networks implementing learning model(s) 134 are implemented as an ensemble of subnetworks trained using datasets widely chosen from approved transactions and flagged transactions, with outputs including classifications of anomalies based upon the input sensed data, and/or remedial actions to be triggered by invoking downstream applications such as preparing and submitting reports to blockchain implemented regulatory compliance information, as well as the capability to both cluster information and to escalate problems.

Having described neural network implementations, the discussion now turns to deep learning approaches.

Figure 13C:
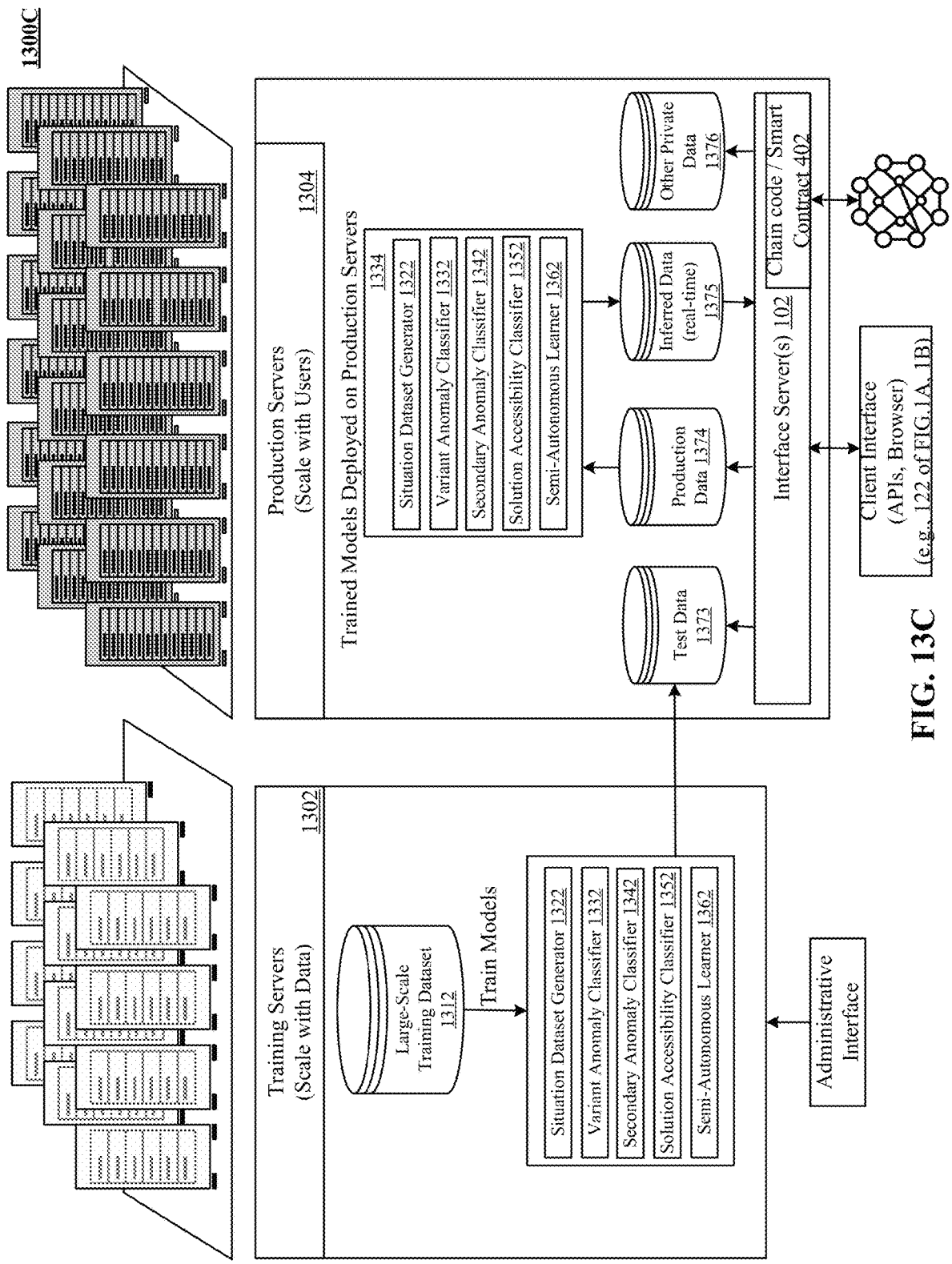
FIG. 13C illustrates a deep learning system in a supervised or semi-supervised implementation.

FIG. 13C illustrates a deep learning system in a supervised or semi-supervised implementation. As shown, deep learning system 1300C includes training servers 1302 and production servers 1304. Large scale training dataset 1312 is accessible to training servers 1302 for training the deep convolutional neural network 1334. In an implementation, deep neural network 1334 includes a first anomaly subnetwork, and a second solution accessibility subnetwork that are trained on one or more training servers 1302. The trained deep neural network ensemble including the first trained anomaly subnetwork, and the trained second solution accessibility subnetwork are deployed on one or more production servers 1304 that receive input anomaly information from requesting client devices 122. The production servers 1304 process the input anomaly information through at least one of the deep neural network 1334, the first anomaly subnetwork, and the second solution accessibility subnetwork to produce outputs that are transmitted to the client devices 122.

Training servers 1302 conduct training using models and comprise a situation dataset generator 1322 includes a deep convolutional neural network based variant anomaly classifier, running on numerous processors coupled to memory that prepares training sets comprising data chosen from large scale training dataset 1312 to reflect one or more scenarios being trained, a variant anomaly classifier 1332 includes a deep convolutional neural network based variant anomaly classifier, running on numerous processors coupled to memory that is trained to recognize anomalous situations from sensed data using the scenarios prepared, an optional secondary classifier 1342 includes a deep convolutional neural network based secondary anomaly classifier, running on numerous processors coupled to memory that is trained to recognize special situation anomalies (e.g., radioactive spill, biohazard, etc.), a solution accessibility classifier 1352 includes a deep convolutional neural network based secondary anomaly classifier, running on numerous processors coupled to memory that is trained to recognize anomalies and output identifiers identifying remedial applications that are invoked to trigger remedial actions. A semi-autonomous learner 1362 includes a deep convolutional neural network based variant anomaly classifier, running on numerous processors coupled to memory that progressively augments a set size of the anomaly training set based on the trained ensemble's evaluation of a synthetic set or in implementations, input of live data from a real world scenario.

In one implementation, the neural networks such as situation dataset generator, variant anomaly classifier, secondary anomaly classifier, solution accessibility classifier, and semi-autonomous learner are communicably linked to the storage subsystem comprised of test data database 1373, production data database 1374, inferred data database 1375 and other private data database 1376 and user interface input devices.

In one implementation, data used in one or more of large scale training dataset 1312, test data database 1373, production data database 1374, inferred data database 1375 and other private data database 1376 is selectively obtained from multiple sources of data: (i) various drug databases (e.g., the FDA Product-Specific Guidance database, which enables searching and clustering by active ingredient(s)) and communications including machine reading of emails on recalls minimizes the need to change notification protocols that can be related to machine-readable data and image recognition (e.g. images of pills) and (ii) user responses to deep learning driven follow-up questions selected by the solution accessibility classifier 1352 and semi-autonomous learner 1362 (allowing for live training and refinement).

Definitions

As used herein, the term "module" refers to a processor that receives information characterizing input data and generates an alternative representation and/or characterization of the input data. A neural network is an example of a module. Other examples of a module include a multilayer perceptron (MLP), a feed-forward neural network, a recursive neural network, a recurrent neural network, a deep neural network, a shallow neural network, a fully-connected neural network, a sparsely-connected neural network, a convolutional neural network that comprises a fully-connected neural network, a fully convolutional network without a fully-connected neural network, a deep stacking neural network, a deep belief network, a residual network, echo state network, liquid state machine, highway network, maxout network, long short-term memory (LSTM) network, recursive neural network grammar (RNNG), gated recurrent unit (GRU), pre-trained and frozen neural networks, and so on. Yet other examples of a module include individual components of a convolutional neural network, such as a one-dimensional (1D) convolution module, a two-dimensional (2D) convolution module, a three-dimensional (3D) convolution module, a feature extraction module, a dimensionality reduction module, a pooling module, a subsampling module, a batch normalization module, a concatenation module, a classification module, a regularization module, and so on. In implementations, a module comprises learnable submodules, parameters, and hyperparameters that can be trained by back-propagating the errors using an optimization algorithm. The optimization algorithm can be based on stochastic gradient descent (or other variations of gradient descent like batch gradient descent and mini-batch gradient descent). Some examples of optimization algorithms used by the technology disclosed include Momentum, Nesterov accelerated gradient, Adagrad, Adadelta, RMSprop, and Adam. In implementations, a module is an activation module that applies a non-linearity function. Some examples of non-linearity functions used by the technology disclosed include a sigmoid function, rectified linear units (ReLUs), hyperbolic tangent function, absolute of hyperbolic tangent function, leaky ReLUs (LReLUs), and parametrized ReLUs (PReLUs). In implementations, a module is a classification module. Some examples of classifiers used by the technology disclosed include a multi-class support vector machine (SVM), a Softmax classifier, and a multinomial logistic regressor. Other examples of classifiers used by the technology disclosed include a rule-based classifier. In implementations, a module is a pre-processing module, such as an input module, a normalization module, a patch-extraction module, and a noise-addition module. In implementations, a module is a post-processing module, such as an output module, an estimation module, and a modelling module. Two modules differ in "type" if they differ in at least one submodule, parameter, or hyperparameter. In some implementations, certain modules are fixed topology modules in which a certain set of submodules are not evolved/modified and/or only evolved/modified in certain generations, and only the interconnections and interconnection weights between the submodules are evolved.

Any other conventional or future-developed neural networks or components thereof or used therein, are considered to be modules. Such implementations will be readily apparent to those skilled in the art without departing from the spirit and scope of the technology disclosed.

As used herein, the term "submodule" refers to a processing element of a module. For example, in the case of a fully-connected neural network, a submodule is a neuron of the neural network. In another example, a layer of neurons, i.e., a neuron layer, is considered a submodule of the fully-connected neural network module. In other examples, in the case of a convolutional neural network, a kernel, a filter, a feature extractor, an activation function, a pooling operation, a subsampling operation, and a regularization operation, are each considered submodules of the convolutional neural network module. In some implementations, the submodules are considered as modules, and vice-versa.

A reporting application includes executable machine instructions that when executed by a processor perform at least initiating one or more reporting action(s). Some types of reporting actions are a regulatory reporting process, filling out part of a regulatory report, concluding at least instructing closing an existing regulatory reporting process, modifying a parameter of metadata stored in association with a regulatory reporting process, submitting a full regulatory report, reporting notice of an anomaly to a market actor, other reporting, and combinations thereof.

A remedial application includes executable machine instructions that when executed by a processor perform at least initiating one or more remedial action(s). Some types of remedial actions are changing the regulatory status of a pharmacy, initiating a freeze on a lot or production run of medications in the event of consistent and verifiable adverse reports, notifying an interested third party, and order more substance, signal that a set of transactions is no longer permitted, change regulatory status of a pharmacy, blocking or disallowing transacting on the blockchain of either potentially counterfeit lot(s), other remedial actions, and combinations thereof.

An input data collecting application includes executable machine instructions that when executed by a processor perform at least initiating one or more data collection. Some types of data collection actions are displaying a prompt to a client to scan a barcode with the camera of a device, other types of sensed data collection, and combinations thereof.

An event type data is at least one selected from a set of a missing pill bottle(s), a mis-delivery of a therapeutic(s) stored on a blockchain, a mis-delivery of a medical service(s) delivered, a mis-coding of a therapeutic(s) or a service(s) properly delivered, an adulterated substance(s), a delivery(ies) not made, and a patient(s) sick or dead, or an adverse event(s) or product problem(s), other types of events identifiable from data, and combinations thereof.

Sensed information about a situation at a site includes detecting a presence of an adulterating substance, such as metallic or glass filings, medication color, a marking on a pill, foul or repugnant odors, an empty vial, a discolored contents, a cracked vial, a damaged packaging, a precipitated medicine inside, a mislabeled vial, other types of sensed information, and combinations thereof.

A system implementation of the technology disclosed includes one or more processors coupled to the memory. The memory is loaded with computer instructions which, when executed on the processors, cause evolution of a deep neural network structure.

The deep neural network structure disclosed herein includes a plurality of modules and interconnections among the modules. Examples of deep neural network structures include without limitation AlexNet, ResNet, Inception, WaveNet, PixelCNN, GoogLeNet, ENet, U-Net, BN-NIN, VGG, LeNet, DeepSEA, DeepChem, DeepBind, DeepMotif, FIDDLE, DeepLNC, DeepCpG, DeepCyTOF, and SPINDLE.

Particular Implementations

In one implementation, we disclose a system for cross-authenticating non-credentialed devices and trusted blockchain enabled applications and gathering information for a blockchain network. The system comprises an interface to a trusted source system for publishing to a server of the trusted source system a mobile application being provided to the non-credentialed devices and a trusted server of a plurality of blockchain nodes having access to a blockchain ledger storing at least pointers to a plurality of documents. The trusted server includes a processor and software that implement generating a request for information uniquely identified by a first randomized token and a link to the mobile application published to the trusted source system authenticating the trusted server as trusted and sending using a first communications modality to at least one recipient non-credentialed device. The processor and software also implement requesting secondary verification information of the non-credentialed device via a copy of the mobile application retrieved by the non-credentialed device from the trusted source system and authenticating the non-credentialed device as an authenticated recipient. An indication of receipt of the request for information from the mobile application as installed by the non-credentialed device as an authenticated recipient is received. The processor and software also implement generating a web page for receiving the information as requested, the web page uniquely identified by a second randomized token mapped to the first randomized token and receiving from the non-credentialed device as an authenticated recipient the information as requested via the web page.

In one implementation, the system further includes sharing public keys by the trusted server with the non-credentialed device as an authenticated recipient.

In one implementation, the first communication modality comprising email.

In one implementation, the first communication modality comprising a push notification.

In one implementation, the system further includes the trusted server storing in a persistent storage a mapping of the first randomized token to the second randomized token.

In one implementation, the system further includes the trusted server resending the request for information to the non-credentialed device as an authorized recipient upon expiry of a time limit to respond.

In one implementation, the system further includes terminating by the trusted server, authentication of the non-credentialed device as an authorized recipient upon expiry of a time limit to respond.

In one implementation, the system further includes terminating by the trusted server, authentication of the non-credentialed device as an authorized recipient upon receiving the requested information.

In one implementation, the secondary verification information further includes the trusted server receiving at least one of a one-time code sent to an email address, a one-time code sent to a phone number via push notification, a one-time code sent encrypted to an email address, and a time-based code with shared secret.

In one implementation, we disclose a computer-implemented method of efficiently implementing a blockchain pharmaceutical regulatory compliance system using a trained exception handling classifier on a data processor with a target architecture. The method includes detecting block-level events stored on a block chain, the events selected from a set of a missing pill bottle, an adulterated substance, a delivery not made, and a patient sick or dead. The method also includes triggering an application to perform one or more actions selected using an ensemble of neural network classifier(s) from a set of submit a regulatory report, notify an interested third party, and order more substance.

In one implementation, the method further includes selecting the action using an exception handling classifier trained using a training data set comprising a plurality of ground truth correspondences of drug identifications, exception events, and remedial actions.

In one alternative implementation, a first neural subnetwork is trained to classify input from a client sensed information into a block level exception event and a second neural subnetwork is trained to provide a remedial action.

In one implementation, the classifier is trained with a ground truth dataset comprising pairings of drug identifications with exception events including sensed discrepancies in the drug or its packaging, and remedial actions including prompts and instructions. In this implementation, the method further includes using the classifier, identifying a drug as an injectable drug in a vial, and triggering an action including prompting the user to specify sensed discrepancies selected for the drug identified.

In one implementation, the sensed discrepancies include one or more selected from an empty vial, a discolored contents, a cracked vial, a damaged packaging, a precipitated medicine inside, and a mislabeled vial.

In one implementation, the classifier is trained with a ground truth dataset comprising pairings of investigative situations with exception events including sensed discrepancies in the drug or its packaging, and remedial actions including capturing evidence of the discrepancies in the drug or its packaging. In this implementation, the method further includes using the classifier, identifying a drug or its packaging as exhibiting a discrepancy, and triggering an action including prompting the user to capture an image, record a sound or scan a bar code.

In one implementation, the classifier is trained with a ground truth dataset comprising pairings of drug identifications with exception events including sensed discrepancies in the drug or its packaging, and remedial actions include prompts and instructions; the method further comprising: using the classifier, identifying a drug as a radioactive drug in "wet packaging", and triggering an action including prompting a user to step away from the drug and to notify a safety officer. In one implementation, the method further includes the classifier identifying a different drug as a non-radioactive injectable drug, and triggering an action including prompting to use caution to avoid getting cut by glass, but if possible, remove vial from outer carton.

In one implementation, the classifier is trained with a ground truth dataset comprising pairings of investigative situations with exception events including sensed discrepancies in the drug or its packaging, and remedial actions include capturing evidence of the discrepancies in the drug or its packaging. In this implementation, the method further comprises using the classifier, identifying two or more discrepancies of a drug shipped to different pharmacies by different wholesalers and each exhibiting evidence of a same discrepancy, and triggering an action including generating reporting escalating the discrepancy to the manufacturer as a cluster.

In one implementation, the method further includes the classifier identifying a common lot or other manufacturing characteristic in problematic vials, and triggering an action including generating a warning to the manufacturer that the common lot potentially has more problems.

In one implementation, the method further includes the classifier assigning weights and likelihoods to a recall and generating a report including the weights and likelihoods to the manufacturer.

In one implementation, the method further includes the classifier sharing the report including the weights and likelihoods to a regulatory authority; thereby enabling the regulatory authority lacking visibility into a supply chain to identify potential recalls.

In one implementation, the classifier is trained with a ground truth dataset comprising pairings of investigative situations with exception events including sensed discrepancies in the drug or its packaging, and remedial actions including capturing evidence of the discrepancies in the drug or its packaging. In this implementation, the method further comprises using the classifier, identifying a duplicate 2D barcode identifier in a first city identical to one in a second city as indicating a potentially counterfeit lot(s), and triggering an action of blocking or disallowing transacting on the blockchain of either potentially counterfeit lot(s).

In one implementation, the method further includes the classifier detecting whether barcode scans were separated by a specific period of time or threshold, and assigning a higher weight to a first temporally occurring scan as original and probably safe to administer, otherwise, the classifier assigning a like weight to the first and second temporally occurring scans; thereby indicating that each is counterfeit.

In one implementation, the classifier is trained with a ground truth dataset comprising pairings of investigative situations with exception events including sensed discrepancies in the drug or its packaging, and remedial actions including capturing evidence of the discrepancies in the drug or its packaging. In this implementation, the method using the classifier, identifying an aggregate number of orders added to the blockchain over a unit time period indicating a shortage, and triggering an action of generating a report to suppliers indicating the shortage; thereby enabling suppliers to pull forward the scheduled manufacturing runs.

In one implementation, the method further includes retrieving data from block-level events storing data from exception reports made to a regulatory body from a blockchain.

In one implementation, the method further includes retrieving data from block-level events storing data from databases in a supply chain.

In another implementation, we disclose a computer-implemented method of preparing a plurality of neural network systems to recognize exception events and drug identifications and to trigger applications that take remedial actions on a data processor with a target architecture. The method includes generating at a time t0, a training data set comprising 50,000 to 1 billion exception events, each exception event labelled with sensed discrepancy information and with drug identifications, and corresponding ground truth remedial actions. The method also includes subdividing the drug identifications into one or more overlapping drug categories. Training a first set of drug classifier neural networks with the drug identifications and the drug categories is also part of the method. The method also includes training a first set of exception classifier neural networks with the sensed information, drug identification information, drug category information, and the corresponding ground truth remedial actions. The method further includes saving parameters from training the recurrent neural networks in tangible machine readable memory for use in reporting or responding to exceptions in pharmaceuticals handling.

In one implementation, the method further includes generating a second training data set at a time t1, later in time than t0, including additional exception events reported after time t0; and using the second training data set, performing the subdividing, training and saving steps to retrain the classifier neural networks and the training recurrent neural networks, thereby enabling the classifiers to learn from subsequent remedial actions.

In one implementation, the generating further includes retrieving the exception events and sensed discrepancy information from block-events stored in a pharmaceutical blockchain.

In one implementation, the generating further including retrieving the drug identifications from a commercial supplier database.

In one implementation, the sensed discrepancies include one or more selected from an empty vial, a discolored contents, a cracked vial, a damaged packaging, a precipitated medicine inside, and a mislabeled vial.

In one implementation, the exception events are select from a set of missing pill bottle, an adulterated substance, allergic reaction, a delivery not made, and a patient sick or dead.

In one implementation, the remedial actions are selected from a set of instruct user to capture an image, record a sound or scan a bar code, prompt user with instructions, submit a regulatory report, notify an interested third party, and order more substance.

In one implementation, the drug categories are selected from a set of opioids, injectable, OTC, prescription, antibiotic, steroid, antihistamine, capsule, tablet, vaccine, and nuclear.

In one implementation, the drug classifier neural networks and the exception classifier neural networks are recursive neural networks (RNN) based on long short term memory (LSTM).

In one implementation, the drug classifier neural networks and the exception classifier neural networks are trained using a combination of current exception events and additional noise data.

In one implementation, the method also includes generating in the training data set, images of the drugs in unadulterated and adulterated form; applying a multilayer convolution and pooling processor and producing reduced dimensionality images from the images of the drugs; training a first set of convolutional neural networks using the reduced dimensionality images and ground truth data indicating whether the images correspond to adulterated drugs or unadulterated drugs.

In another alternative implementation, we disclose a method of recognizing discrepancies in drug images in adulterated and unadulterated states and to trigger applications that take remedial actions on a data processor with a target architecture. The method includes applying a multilayer convolution to a plurality of images of drugs and pooling processor and producing reduced dimensionality images, including first and second reduced dimensionality images, from the plurality of drug images including a drug image of the drug in an adulterated state and a drug image of the drug in an unadulterated state. The method can also include processing a pair of first and second reduced dimensionality images using a first neural network to produce estimated classification parameters, using pairs of first and second reduced dimensionality images, estimated classification parameters for the first and second reduced dimensionality images, image data for presentation, and labeled ground truth conclusions indicating whether the classification parameters correspond to a drug in an adulterated state or a drug in an unadulterated state. The method also includes saving the parameters in a tangible machine readable memory for use in drug image recognition.

In one implementation, the parameters are selected from a set of color, shape, size, markings, texture.

In one implementation, the method further includes capturing drug images of drugs in an adulterated state and in an unadulterated state.

In a further alternative implementation, we disclose a method of preparing sample pharmaceutical regulatory compliance for training of neural network systems on a data processor with a target architecture. The method includes accessing in regulatory agency reporting system a plurality of reports with parameters that specify: type of report; incident number provided by a regulatory authority; date of initial notification to the regulatory authority; date company determined product was illegitimate; classification of notification; name of product as it appears on the label; primary ingredients; drug use selected from a set of human, and other; drug description; strength of drug; dosage form; quantity; national drug code number; serial number; lot number; expiration date; for notification, description of event/issue; other reports submitted; company name and address; company category; unique facility number; and contact information. The method can also include generating between 50,000 and 1 billion exception event simulations, each simulation labeled with 5 to 15 selected parameters, including a drug identification. Saving the simulated exception events with labelled ground truth parameters indicating at least remedial events to be triggered for use in training a neural network in a pharmaceutical regulatory compliance system is also part of the method.

In one implementation, the type of report is selected from a set of initial notification, follow-up notification, and request for termination.

In one implementation, classification of notification is selected from a set of counterfeit, diverted, stolen, intentional adulteration, unfit for distribution, and fraudulent transaction.

In one implementation, the drug description is selected from a set of finished prescription drug, vaccine, plasma derivative, including one of coagulation factors, immunoglobulins, albumin, allergenic, including standardized and non-standardized, and multiple.

In one implementation, dosage form is selected from a set of tablet, capsule, aerosol, oral liquid, sublingual, injectable, topical, suppository, other, and multiple.

In one implementation, other reports is selected from a set of filed alert report, a biological product deviation report, a medical-watch report, none, and other.

In one implementation, category is selected from a set of manufacturer, wholesale distributor, dispenser, and repackager.

In one implementation, the method further includes accessing additional parameters stored in a commercial supplier database; and using the additional parameters to generate the simulations.

In another alternative implementation, we disclose a method of securing clinical trial data on a data processor with a target architecture. The method includes receiving a request to manipulate clinical trial information in block-level clinical trial structures stored to a blockchain. Determining whether the request is made by a participant in a clinical trial or a scientist conducting a clinical trial can also be part of the method. The method also includes permitting access to the participant of a subset of the clinical trial information suitable for the participant, otherwise permitting access to the scientist of a different subset of the clinical trial information suitable for the scientist.

In one implementation, the request is a request to enter patient data. The method also includes locating a block on the chain in which the patient data relates; determining whether the request is authorized under a smart contract governing the use of the clinical trial blockchain; and adding the patient to the clinical trial whenever the request is authorized.

In one implementation, the request is a request to delete patient data. The method also includes locating a block on the chain in which the patient data relates; determining whether the request is authorized under a smart contract governing the use of the clinical trial blockchain; and deleting the patient from the clinical trial whenever the request is authorized.

In one implementation, the request is a request to order a specific substance for a patient in a clinical trial. The method further includes determining which group a patient is in and delivering correct amount of substance.

In one implementation, the method also includes detecting a set of patient parameters after substance administration and gathering it back on the chain.

In one implementation, the method also includes mixing artificially generated patient data with real patient data in the block chain.

In one implementation, the method also includes detecting and adding longitudinal patient outcomes.

In one implementation, the method also includes mixing multiple studies on a single block chain to perform meta-analysis.

In yet further alternative implementation, we disclose a method of finding additional instances of like events from a reported first event involving a first physical object. The method includes receiving by a trusted server having access permissions to a permissioned blockchain network, a report by an unverified source, the report identifying the first physical object. Establishing by the trusted server, a trusted interactive conversation with the unverified source, the trusted interactive conversation identified by a unique random token, wherein physical parameters of the first physical object are prompted for, and values for the physical parameters are returned can also be part of the method. The method can also include determining by the trusted server from the values for the physical parameters received, values for one or more associated block chain parameters using a machine intelligence process; and creating by the trusted server, using the values for one or more associated block chain parameters, a new block chain block. Further the method can include sending the new block chain block populated with at least some of the values for one or more associated block chain parameters in connection with the unique random token to be added to the permissioned blockchain network; thereby enabling other trusted servers with access to the permissioned blockchain network to provide indication of additional instances of like events based upon the values for one or more associated block chain parameters.

In one implementation, the machine intelligence process further includes determining associated block chain parameters using a trained neural network classifier trained using a training set of example physical parameter values and example associated block chain parameters.

In one implementation, the machine intelligence process further includes applying a semi-supervised statistical machine learner to documents linked to blocks stored with the permissioned blockchain network to develop patterns of data recognized from in the documents; using the semi-supervised statistical machine learner to encode blockchain data representing healthy states (Xh) and unhealthy states (Xu) to latent vectors representing block level data mapped into a latent vector space; and using the semi-supervised statistical machine learner to identify data points corresponding to blocks of a certain Mahalanobis distance from data clusters labelled as desirable.

In one implementation, the method further includes identifying patterns in the data points indicating clusters of data, and applying a label to each cluster; and continuously training a classifier including a neural network with at least some of the clusters and the labels.

In one implementation, the values for one or more associated block chain parameters are determined by aggregating information obtained from multiple blocks in the blockchain network selected by the machine intelligence process using the physical parameters.

In one implementation, the values for one or more associated block chain parameters are determined from a set including at least a plurality of Counterfeit, Diverted, Stolen, Intentional adulteration, Unfit for distribution, and Fraudulent transaction.

In one implementation, the values for physical parameters are detected from a set including at least a plurality of a presence of an adulterating substance, such as metallic or glass filings, medication color, a marking on a pill, foul or repugnant odors, an empty vial, a discolored contents, a cracked vial, a damaged packaging, a precipitated medicine inside, and a mislabeled vial.

In one implementation, the first event involving a first physical object is selected from a set of a missing pill bottle(s), a mis-delivery of a therapeutic(s) stored on a blockchain, a mis-delivery of a medical service(s) delivered, a mis-coding of a therapeutic(s) or a service(s) properly delivered, an adulterated substance(s), a delivery(ies) not made, and a patient(s) sick or dead in connection with a product, or an adverse reaction event(s) in connection with a product problem(s).

In one implementation, the method further includes the trusted server generating and providing the unique random token to the unverified source, accompanied by a link to a trusted application for making interactive requests for information of the unverified source.

In one implementation, the method further includes the link linking to a copy of the trusted application stored at an application store for download, the trusted application verifying the trusted server to the unverified source.

In one implementation, the method further includes providing by the trusted application an offer to the unverified source to login to the trusted server and receiving from the unverified source a login into the trusted server.

In one implementation, the method further includes completing two-factor identification verifying the unverified source to the trusted server.

In a still yet further alternative implementation, we disclose a method of finding additional instances of problem shipments from a problem report of a first damaged shipment, that includes receiving by a trusted server having access permissions to a permissioned blockchain network, a report by an unverified source, the report indicating one or more problems with the first damaged shipment. Establishing by the trusted server, a trusted interactive conversation having a unique random token, with the unverified source, wherein physical parameters of the first damaged shipment are prompted for, and values for the physical parameters are returned is also part of the method. The method further includes determining by the trusted server from the values for the physical parameters received, values for one or more associated block chain parameters; and creating by the trusted server, using the values for one or more associated block chain parameters, a new block chain block. The method finally includes sending the new block chain block populated with at least some of the values for one or more associated block chain parameters in connection with the unique random token to be added to the permissioned blockchain network.

In one implementation, the method further includes whereby the sending the new block chain block enables other trusted servers with access to the permissioned blockchain network to provide indication of additional instances of problem shipments based upon the values for one or more associated block chain parameters.

In one implementation, the method further includes the trusted server using a machine intelligence process to determine values for one or more associated block chain parameters from the values for the physical parameters received.

In one implementation of the method, the first damage shipment includes damaged packaging to a medication, further including determining using the neural network based trained classifier, other shipments of products of an increased probability of experiencing damage consistent with damage experience by the first damaged shipment.

In one implementation, the method further includes the trusted server using a smart contract implementing a classifier to determine values for one or more associated block chain parameters from the values for the physical parameters received.

In one implementation of the method, values for one or more associated block chain parameters are determined from a set including at least a plurality of Counterfeit, Diverted, Stolen, Intentional adulteration, Unfit for distribution, and Fraudulent transaction.

In one implementation of the method values for physical parameters are detected from a set including at least a plurality of a presence of an adulterating substance, such as metallic or glass filings, medication color, a marking on a pill, foul or repugnant odors, an empty vial, a discolored contents, a cracked vial, a damaged packaging, a precipitated medicine inside, and a mislabeled vial.

In one implementation of the method a problem shipment has experienced an event selected from a set of a missing pill bottle(s), a mis-delivery of a therapeutic(s) stored on a blockchain, a mis-delivery of a medical service(s) delivered, a mis-coding of a therapeutic(s) or a service(s) properly delivered, an adulterated substance(s), a delivery(ies) not made, and a patient(s) sick or dead in connection with a product, or an adverse reaction event(s) in connection with a product problem(s).

In one implementation, the method further includes the trusted server initiating the trusted interactive conversation by generating the unique random token and providing to the unverified source the unique random token accompanied by a link to an application making interactive requests for information of the unverified source.

In one implementation, the method further includes the link linking to a copy of the application stored at an application store for download, the application verifying the trusted server to the unverified source.

In one implementation, the method further includes providing by the application an offer to the unverified source to login to the trusted server and receiving from the unverified source a login into the trusted server.

In one implementation, the method further includes completing two-factor identification verifying the unverified source to the trusted server.

In a still yet further alternative implementation, we disclose a method of initiating commanded actions responsive to reported events in which intervention is desired that includes receiving by a trusted server having access permissions to a permissioned blockchain network, an indication by an unverified source, the indication identifying an occurrence or a probability of occurrence of one or more events in which intervention is desired. The method further includes establishing by the trusted server, a trusted interactive conversation having a unique random token, with the unverified source, wherein physical parameters of the one or more events are prompted for, and values for the physical parameters are returned. Further, the method can include detecting using a machine learning algorithm a first state and a probability of the state based upon the values for the physical parameters; wherein the first state further prompts a first notification to take an action. Also part of the method is capturing by the trusted server an indication that the action prompted has occurred; and creating by the trusted server, using the first state, the first notification to take an action, and the values for the physical parameters, a new block chain block. The method finally includes sending the new block chain block populated with at least some of the values for one or more the first state, the first notification to take an action, and the values for the physical parameters in connection with the unique random token to be added to the permissioned blockchain network; thereby enabling other trusted servers with access to the permissioned blockchain network to provide indication of actions taken in connection with additional instances of like events.

In one implementation, the method further includes detecting a second state indicating an incorrect response to the first state has occurred, and using the machine learning algorithm to select a further action based upon a the detected existence of the second state.

In one implementation, the method further includes the trusted server receiving additional information including values for the physical parameters, using the machine learning algorithm to select a further action based upon a detected existence of a second state; and prompting second notification according to the second state.

In one implementation of the method, the second state corresponds to the first notification is in error, the method further including the second notification cancels the first notification.

In one implementation of the method the second state corresponds to the first notification is in error, the method further including second notification amends the first notification.

In one implementation of the method the trusted server generating the new block further includes the new block indicating a Request generated, indicating that the first notification is created and sent to one or more recipients.

In one implementation of the method the trusted server generating the new block further includes the new block indicating Response recorded, indicating that at least one recipient has responded to the first notification.

In one implementation of the method the trusted server generating the new block further includes the new block indicating Request expiration approaching, indicating a reminder event.

In one implementation of the method the trusted server generating the new block further includes the new block indicating Request expired, indicating the request expired and can no longer be directly responded to without a fresh request being generated.

In one implementation of the method the trusted server generating the new block further includes the new block indicating Request invalidated, indicating that a request that has not been responded to can be invalidated, or that no response to it may be recorded.

Use Case

Under the US statutes associated with Drug Supply Chain Security Act (DSCSA)/Drug Quality and Security Act (DQSA), wholesalers and dispensers of drugs are required to submit Form FDA 3911 to the FDA, as well as separately notify immediate trading partners, when illegitimate products are discovered. Separate channels are specified for reporting by prescribers and patients, such as MedWatch, the FDA's safety information and adverse event reporting program. One implementation of a neural network enabled interface server as a blockchain proxy user facilitates mandated reporting, improving speed, ease of use, reliability, and security. As a broader concept, this is an exception handling and root cause analysis system driven by a neural network enabled interface server and blockchain, with significant implications for federal safety and compliance reporting. For example within the drug and healthcare reporting field, this approach could address reporting among both professionals and consumers: FDA: Field Alert Report (FAR), FDA: Biological Product Deviation Report (BPDR), FDA: Form 3500 (Medwatch, voluntary reporting by healthcare professionals, consumers, and patients), FDA: Form 3500A (Medwatch, mandatory reporting by IND reporters, manufacturers, distributors, importers, and user facilities personnel), FDA: Form 3500B (Medwatch, voluntary reporting by consumers), FDA: Reportable Food Registry, FDA: Vaccine Adverse Event Reporting System (VAERS), FDA: Investigative Drug/Gene Research Study Adverse Event Reports, FDA: Potential Tobacco Product Violations Reporting (Form FDA 3779), USDA *APHIS* Center for Veterinary Biologics Reports, USDA Animal and Plant Health Inspection Service: Adverse Event Reporting, USDA FSIS Electronic Consumer Complaints, DEA Tips, Animal Drug Safety Reporting, Consumer Product Safety Commission Reports, State/local reports: Health Department, Board of Pharmacy, and others.

Implementations incorporating machine/barcode reading for faster initiation and better data integrity, neural networks implementing categorization and linking to historical challenges, and blockchain including timestamping, tracking, thereby driving a near-real-time resolution system. Certain implementations enable achieving identification of suspect products and, products with a high risk of illegitimacy. Certain implementations enable achieving notification of illegitimate products and products with a high risk of illegitimacy.

Implementations can provide stakeholders the most likely paths to resolve the issue at the micro and macro levels—determining the proper course of action for the specific challenge, while intelligently and selectively broadcasting notifications of events (such as recalls) to relevant subsets of subscribers. Using blockchain, system implementations can generate notifications to parties upstream and downstream via text and/or email and can enable counterparties to both resolve exceptions and link them to related exceptions (thus identifying larger event patterns).

One implementation of a neural network enabled interface server works with a mobile device and eliminates the need to transcribe data from the bottle. A neural network enabled interface server implementation will be trained to readily determine whether or not the medicine in question is in a pill form and suggest responses like "missing pills" or "crushed or broken pills" that are germane to that medicine, whereas a liquid medicine will present different choices.

Trading partners are not given visibility into all relevant transactions; instead, one implementation employs differential privacy to send reports of similar events. Along with fulfilling the minimum information requirements of FDA Form 3911, one implementation enables the functionality for trading partners to ask extemporaneous questions; one deep learning implementation can employ those questions to ask similar questions in similar situations.

One implementation of a neural network enabled interface server is able to gather additional data, flag out-of-spec assets, identify ecosystem-level patterns, and engage in root-cause analysis. Such implementations employ cluster identification, free-form typical input learning, convolutional neural network (CNN), and bad actor identification and others.

One implementation can receive photos of barcodes taken by a third party, optical character recognition of the human-readable label, and XML or other machine files with the same information. One implementation provides pill recognition based on publicly available image recognition frameworks. One implementation provides the reporting party with a series of deep learning driven modal screens, enabling participants to accurately and rapidly regulators and counterparties ("trading partners") of problems.

Other Use Cases

Implementations of a block chain trained classifier include drug manufacturers, drug wholesalers, hospitals, and pharmacies doing business in the United States and other countries. Implementations incorporating cluster analysis, root cause, block chain and convolutional neural network as a trained classifier can provide prompt contemporaneous notification, compliance reporting, epidemiology, surveillance, and exception handling. Additional use cases include implementations used for food safety, medical devices, and vaccines.

The terms and expressions employed herein are used as terms and expressions of description and not of limitation, and there is no intention, in the use of such terms and expressions, of excluding any equivalents of the features shown and described or portions thereof. In addition, having described certain implementations of the technology disclosed, it will be apparent to those of ordinary skill in the art that other implementations incorporating the concepts disclosed herein can be used without departing from the spirit and scope of the technology disclosed. Accordingly, the described implementations are to be considered in all respects as only illustrative and not restrictive.

Legal documents. Lawyers rely heavily on burdensome paper trails and myriad third-party services to track legal filings and handle disclosures. One neural network enabled interface server implementation clusters discrepancies or potential conflicts of interest among various parties, and send notifications to relevant parties. (For example, applying natural language processing [NLP] and clustering analysis to identify business records filed in two separate cases that substantially overlap, or clustering names of interested parties would reveal a scenario where a law firm may be acting for more than one client in separate but related matters. In these cases, the neural network enabled interface server would send notifications to court officials.)

Patent filings and lawsuits. Patent trolling has increasingly been used as a means to stifle rather than encourage innovation; over the last several years, Vermont, Nebraska, Minnesota, Wisconsin, and Idaho have all implemented legislation or taken other steps to punish bad faith assertions of patent infringement. By analyzing all patent filings over time, as well as accepting reports of bad faith infringement threats (either submitted by individuals through a web or mobile client, or via machine-to-machine [M2M] reports from court IT systems), one neural network enabled interface server implementation would notify the U.S. Patent Office and other stakeholders of questionable patent filings by bad actors (identified through clustering reports of frivolous lawsuits and performing NLP to identify overly broad or non-specific filings).

Financial documents and investments. By analyzing the filings sent to one or more regulators such as the SEC, one neural network enabled interface server implementation identifies and sends notifications regarding discrepancies or unusual correlations among filings—not just to the regulator, but also to a submitter of multiple filings where the discrepancy may be unintended.

Anti-money laundering. Under the Bank Secrecy Act of 1970, financial institutions in the United States are obligated to keep records of (and in some cases file reports of) cash purchases of negotiable instruments, as well as report suspicious activity. By performing NLP on Financial Crimes Enforcement Network (FinCEN) submissions and related media, one neural network enabled interface server implementation identifies partial name and account matches, match multi-step transactions, and identifies unusual bursts of activity across a variety of factors, including institution and geography.

Import/export and customs. From perishable goods to electronic components, imported and exported goods are covered by a wide range of regulatory and disclosure requirements, with stakeholders including trading partners, customs officials, shipping companies, and state and federal regulators for specific industries. One neural network enabled interface server implementation generates notifications on potential faulty, illegitimate, or illegal products being moved across borders.

Food safety. In the United States, food safety is covered by a wide range of agencies, including the USDA (meat and poultry products), FDA (all other foods marketed in interstate commerce), EPA (pesticide products), the National Marine Fisheries Service (seafood inspection and grading), and myriad other agencies as well as state and local regulatory systems. Reporting systems include the aforementioned Medwatch, the Reportable Food Registry, and many other ad hoc approaches such as call centers. By funneling these reports (including geographies, food consumed, and medical symptoms) into the blockchain, either directly or through machine-to-machine (M2M) connections, one neural network enabled interface server implementation identifies clusters across various reports arising from potentially related instances, and sends notifications to appropriate authorities. By leveraging user-submitted images (e.g. of food labels and spoilage) and convoluted neural networks, one neural network enabled interface server implementation generates conclusions and deploy notifications to the relevant health authorities.

Diamonds. The prevalence of blood diamonds—diamonds mined in war zones and sold to further illegal activities or atrocities—has resulted in the need for various companies throughout the global diamond supply chain to document the provenance of their gems. By clustering variables such as weight and provenance, one neural network enabled interface server implementation identifies suspicious transactions and notify customs officials and industry groups where blood diamonds might be making their way into the legitimate supply chain.

Radioactive materials. The global tracking of fissile materials poses a unique challenge to world governments. On a blockchain with smart contracts that adhere to national policies as well as the Treaty on the Non-Proliferation of Nuclear Weapons, this inventory could be tracked in a way that would prevent bad actors from altering records after they have been created. A neural network enabled interface server implementation generates notifications related to unusual activity or suspicious clustering to a predefined national or international overseeing body, such as the Nuclear Regulatory Commission or the International Atomic Energy Agency.

Specific ideas of networks and actions further includes: (A) Supply chain management systems, e.g., (i) Transaction of a good from one party to another; (ii) Request for information about a supply chain participant, an item in the supply chain, or a transaction/event in the supply chain, i.e., RFI dispatched to appropriate individual, who adds in the appropriate missing information, and (iii) Exception handling for errors that occur in the supply chain (e.g. a delivery was late, what does the person in charge at the delivering company say caused it); (B) Cyber security systems, e.g., (i) Anomalous event detected in a network, a human enters, (a) Threat assessment of the anomalous event (b) Actions taken to mitigate the threat; (C) 2FA systems, e.g., (i) Log-in to device, dispatch notification to a second semi-trusted channel; (D) System for monitoring "critical infrastructure" (think power plants, networks infrastructure) (a) Anomalous event detected in infrastructure, a human enters (i) Threat assessment of the anomalous event (ii) Actions taken to mitigate the threat; (E) Systems for monitoring or logging patient's health, e.g., Patient's implanted EKG reports the patient's heart has flatlined. System sends notification to patient's phone asking if they are still alive. "No response" transaction is logged after 10 minutes if they don't respond. If they do respond, "false positive" transaction is logged; (F) Banking systems, e.g., (a) Anomalous event detected in account activity, a human enters, (i) Threat assessment of the anomalous event, (ii) Actions taken to mitigate the threat; (b) Unlabeled transaction appears in an account, e.g., (i) Message dispatched to account administrator to capture additional information about the transaction, (G) Insurance systems of record, (a) Blockchain system detects that an event that was covered by insurance has occurred (e.g. hospitalization), (i) Sends an oraculus request to a patient and/or their care team to gather more information about what exactly happened; (H) Social media networks, (I) Approval of actions, e.g., (i) A user in a blockchain network carries out a transaction X, an oraculus request is sent to a party authorized to approve the transaction (e.g. FDA), and they can approve/deny; (J) General abstractions of the info gathering concept, (K) Critical system/asset monitoring (networks, power plants, people), (i) Alert/filter out anomalies, e.g., (a) Gathers training data for machine learning, (L) Exception handling, (i) A transaction is attempted between two parties and fails, additional information is needed for how to proceed following the failed transaction, (ii) Networks, e.g., (a) Supply chain; (M) Approval of transaction, (i) Transaction of material or data is proposed by party A and B, out-of-network party C needs to approve transaction, e.g., (a) Party C can be an AI, (b) Gathers training data for an AI that's a digital regulator; (ii) Networks, e.g., (a) Information systems e.g. social networks, (b) Trade/supply chain, (c) Log in/2FA, (N) Event-driven information gathering, (i) Blockchain system detects that an event has occurred (e.g. hospitalization), (a) Sends an oraculus request to a patient and/or their care team to gather more information about what exactly happened, (ii) Networks, e.g., (a) Banking transactions, (b) Insurance claims, (c) Supply chain, and others.

This system implementation and other systems disclosed optionally include one or more of the foregoing features. System can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

Other implementations may include a non-transitory computer readable storage medium storing instructions executable by a processor to perform actions of the system described above. Each of the features discussed in the particular implementation section for other implementations apply equally to this implementation. As indicated above, all the other features are not repeated here and should be considered repeated by reference.

The preceding description is presented to enable the making and use of the technology disclosed. Various modifications to the disclosed implementations will be apparent, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein. The scope of the technology disclosed is defined by the appended claims.

We claim as follows:

1. A method of finding reportable adverse events to be reported from an input data set including parameters describing a first event involving a first physical object, including:

receiving by a trusted server having access permissions to a server network, a request by an unverified source to report an adverse event, the report identifying the first physical object;

establishing by the trusted server, a trusted interactive conversation with the unverified source, the trusted interactive conversation identified by a unique token, wherein physical parameters of the first physical object are prompted for, and values for the physical parameters are returned;

using a machine intelligence process, determining by the trusted server from the values for the physical parameters received, values for one or more associated event parameters;

creating by the trusted server, using the values for one or more associated event parameters, a new report identifying the first physical object and populated with event parameters determined by the machine intelligence process to be associated with the adverse event; and notifying other trusted servers with access to the server network, of the new report as populated.

2. The method of claim 1, wherein the machine intelligence process further includes determining values for one or more associated event parameters using a trained neural network classifier trained using a training set of example physical parameter values and example associated event parameters.

3. The method of claim 1, wherein the machine intelligence process further includes:

applying a semi-supervised statistical machine learner to documents stored with the server network to develop patterns of data recognized from within the documents;

using the semi-supervised statistical machine learner to encode data representing healthy states (Xh) and unhealthy states (Xu) to latent vectors representing event level data mapped into a latent vector space; and using the semi-supervised statistical machine learner to identify data points, corresponding to events of a certain Mahalanobis distance from data clusters labelled as desirable.

4. The method of claim 3, further including identifying patterns in the data points identified, the patterns indicating clusters of data, and applying a label to each cluster; and continuously training a classifier including a neural network with at least some of the clusters and the labels.

5. The method of claim 1, wherein values for one or more associated event parameters are determined by aggregating information obtained from multiple reports of events in the server network selected by the machine intelligence process using the physical parameters.

6. The method of claim 1, wherein values for one or more associated event parameters are determined from a set including at least a plurality of counterfeit, diverted, stolen, intentional adulteration, unfit for distribution, and fraudulent activity.

7. The method of claim 1, wherein values for physical parameters are detected from a set including at least a plurality of a presence of an adulterating substance, such as metallic or glass filings, medication color, a marking on a pill, foul or repugnant odors, an empty vial, a discolored contents, a cracked vial, a damaged packaging, a precipitated medicine inside, and a mislabeled vial.

8. The method of claim 1, wherein first event involving a first physical object is selected from a set of a missing pill bottle, a mis-delivery of a therapeutic, a mis-delivery of a medical service delivered, a mis-coding of a therapeutic or a service properly delivered, an adulterated substance, a delivery not made, and a patient sick or dead in connection with a product, or an adverse reaction event in connection with a product problem.

9. The method of claim 1, further including the trusted server generating and providing a unique random token to the unverified source, accompanied by a link to a trusted application for making interactive requests for information of the unverified source, the link linking to a copy of the trusted application stored at an application store for download, the trusted application verifying the trusted server to the unverified source.

10. The method of claim 1, further including obtaining from other trusted servers with access to the server network, indication of additional instances of like events based upon the values for one or more associated event parameters in the new report as populated.

11. A non-transitory computer readable medium storing instructions for finding reportable events to be reported from an input data set including parameters describing a first event involving a first physical object, which instructions when executed by one or more processors perform a method comprising:
receiving by a trusted server having access permissions to a server network, a request by an unverified source to report an adverse event, the report identifying the first physical object;
establishing by the trusted server, a trusted interactive conversation with the unverified source, the trusted interactive conversation identified by a unique token, wherein physical parameters of the first physical object are prompted for, and values for the physical parameters are returned;
using a machine intelligence process, determining by the trusted server from the values for the physical parameters received, values for one or more associated event parameters;
creating by the trusted server, using the values for one or more associated event parameters, a new report identifying the first physical object and populated with event parameters determined by the machine intelligence process to be associated with the adverse event; and
notifying other trusted servers with access to the network, of the new report as populated.

12. The non-transitory computer readable medium of claim 11, wherein the machine intelligence process further includes determining associated event parameters using a trained neural network classifier trained using a training set of example physical parameter values and example associated event parameters.

13. The non-transitory computer readable medium of claim 11, wherein the machine intelligence process further includes:
applying a semi-supervised statistical machine learner to documents stored with the server network to develop patterns of data recognized from within the documents;
using the semi-supervised statistical machine learner to encode data representing healthy states (Xh) and unhealthy states (Xu) to latent vectors representing event level data mapped into a latent vector space; and
using the semi-supervised statistical machine learner to identify data points corresponding to events of a certain Mahalanobis distance from data clusters labelled as desirable.

14. The non-transitory computer readable medium of claim 13, further including identifying patterns in the data points indicating clusters of data, and applying a label to each cluster; and continuously training a classifier including a neural network with at least some of the clusters and the labels.

15. The non-transitory computer readable medium of claim 11, wherein values for one or more associated event parameters are determined by aggregating information obtained from multiple reports of events in the server network selected by the machine intelligence process using the physical parameters.

16. The non-transitory computer readable medium of claim 11, wherein values for one or more associated event parameters are determined from a set including at least a plurality of counterfeit, diverted, stolen, intentional adulteration, unfit for distribution, and fraudulent activity.

17. The non-transitory computer readable medium of claim 11, wherein values for physical parameters are detected from a set including at least a plurality of a presence of an adulterating substance, such as metallic or glass filings, medication color, a marking on a pill, foul or repugnant odors, an empty vial, a discolored contents, a cracked vial, a damaged packaging, a precipitated medicine inside, and a mislabeled vial.

18. The non-transitory computer readable medium of claim 11, wherein first event involving a first physical object is selected from a set of a missing pill bottle, a mis-delivery of a therapeutic, a mis-delivery of a medical service delivered, a mis-coding of a therapeutic or a service properly delivered, an adulterated substance, a delivery not made, and a patient sick or dead in connection with a product, or an adverse reaction event in connection with a product problem.

19. The non-transitory computer readable medium of claim 11, further including the trusted server generating and providing a unique random token to the unverified source, accompanied by a link to a trusted application for making interactive requests for information of the unverified source; wherein the link links to a copy of the trusted application stored at an application store for download, the trusted application verifying the trusted server to the unverified source.

20. The non-transitory computer readable medium of claim 11, further including obtaining from other trusted servers with access to the server network, indication of additional instances of like events based upon the values for one or more associated event parameters in the new report as populated.

21. A system for finding reportable events to be reported from an input data set including parameters describing a first event involving a first physical object, the system comprising:
an interface to a trusted source system for publishing to a server of the trusted source system a mobile application being provided to one or more non-credentialed devices;
a trusted server having access to a plurality of trusted server nodes storing at least pointers to a plurality of documents, the trusted server including a processor and software that implement:
receiving by a trusted server having access permissions to a server network, a request by an unverified source to report an adverse event, the report identifying the first physical object;
establishing by the trusted server using the interface to a trusted source system for publishing to a server of the trusted source system a mobile application being provided to the non-credentialed devices, a trusted interactive conversation with the unverified source, the trusted interactive conversation identified by a unique token, wherein physical parameters of the first physical object are prompted for, and values for the physical parameters are returned;

using a machine intelligence process, determining by the trusted server from the values for the physical parameters received, values for one or more associated event parameters;

creating by the trusted server, using the values for one or more associated event parameters, a new report identifying the first physical object and populated with event parameters determined by the machine intelligence process to be associated with the adverse event; and notifying other trusted servers with access to the server network, of the new report as populated.

* * * * *